US010329346B2

(12) United States Patent
Auer et al.

(10) Patent No.: US 10,329,346 B2
(45) Date of Patent: Jun. 25, 2019

(54) TNFA-IL-17 BISPECIFIC ANTIBODIES

(71) Applicant: Hoffmann-La Roche Inc., Nutley, NJ (US)

(72) Inventors: Johannes Auer, Schwaigen (DE); Martin Bader, Penzberg (DE); Jens Fischer, Weilheim in Oberbayern (DE); Stefan Lorenz, Penzberg (DE); Joerg Moelleken, Munich (DE); Stefan Seeber, Sindelsdorf (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 181 days.

(21) Appl. No.: 15/012,499

(22) Filed: Feb. 1, 2016

(65) Prior Publication Data

US 2016/0326241 A1 Nov. 10, 2016

Related U.S. Application Data

(63) Continuation of application No. PCT/EP2014/066581, filed on Aug. 1, 2014.

(30) Foreign Application Priority Data

Aug. 1, 2013 (EP) .................................. 13178969

(51) Int. Cl.
*C07K 16/24* (2006.01)
*C07K 16/46* (2006.01)
*A61K 39/395* (2006.01)

(52) U.S. Cl.
CPC .......... *C07K 16/244* (2013.01); *C07K 16/241* (2013.01); *C07K 16/468* (2013.01); *C07K 2317/31* (2013.01); *C07K 2317/35* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| 5,202,238 | A | 4/1993 | Fell, Jr. et al. |
| 5,204,244 | A | 4/1993 | Fell et al. |
| 6,171,586 | B1 | 1/2001 | Lam et al. |
| 6,267,958 | B1 | 7/2001 | Andya et al. |
| 9,676,845 | B2 | 6/2017 | Imhof-Jung et al. |
| 2010/0266531 | A1* | 10/2010 | Hsieh .................. C07K 16/241 424/85.2 |

FOREIGN PATENT DOCUMENTS

| WO | WO 94/029350 A2 | 12/1994 |
| WO | WO 94/029350 A3 | 12/1994 |
| WO | WO-2006/044908 A2 | 4/2006 |
| WO | WO-2006/044908 A3 | 4/2006 |
| WO | WO 2009/080253 A1 | 7/2009 |
| WO | WO2010/028797 | * 3/2010 |
| WO | WO-2010/102251 A2 | 9/2010 |
| WO | WO-2010/102251 A3 | 9/2010 |
| WO | WO-2011/117330 A1 | 9/2011 |
| WO | WO-2012/018790 A2 | 2/2012 |
| WO | WO-2015/014979 A1 | 2/2015 |

OTHER PUBLICATIONS

Brummell et al, Biochemistry; 1993; vol. 32, pp. 1180-1187.*
Kobayashi et al. Protein Engineering; 1999; vol. 12, pp. 879-844.*
Brorson et al. J. Immunol; 1999; vol. 163, pp. 6694-6701.*
Coleman Research in Immunol; 1994; vol. 145; pp. 33-36.*
Ash et al. "The Role of Tocilizumab in the Management of Rheumatoid Arthritis," *Expert Opin. Biol. Ther.* 12(9):1277-1289, (2012, e-pub. Jul. 31, 2012).
Atzeni et al. "Anti-Cytokine Antibodies for Rheumatic Diseases," *Curr. Opin. Investigational Drugs* 10(11):1204-1211, (Nov. 2009).
Barnes et al. "Advances in Animal Cell Recombinant Protein Production: GS-NS0 Expression System," *Cytotechnology* 32:109-123, (2000).
Barnes et al. "Characterization of the Stability of Recombinant Protein Production in the GS-NS0 Expression System," *Biotech. Bioeng.* 73(4):261-270, (May 20, 2001).
Bossaller et al. "Monoclonal Antibody Treatments for Rheumatoid Arthritis," *Expert Opinion on Biological Therapy* 13(9):1257-1272, (2013, e-pub. Jun. 21, 2013).
Brennan et al. "Inhibitory Effect of TNFα Antibodies on Synovial Cell Interleukin-1 Production in Rheumatoid Arthritis," *Lancet* 2:244-247, (Jul. 29, 1989).
Cañete et al. "Biological Therapy in Rheumatoid Arthritis," *Current Topics in Medicinal Chemistry* 6:752-75, (2013).
Carter et al. "Humanization of an Anti-185$^{HER2}$ Antibody for Human Cancer Therapy," *Proc. Natl. Acad. Sci. USA* 89:4285-4289, (May 1992).
Church et al. "Rheumatoid Synovial Fluid Interleukin-17-Producing CD4 T Cells Have Abundant Tumor Necrosis Factor-Alpha Co-Expression, but Little Interleukin-22 and Interleukin-23R Expression," *Arthritis Research and Therapy* 12(5)(R184):1-13, (Oct. 7, 2010).
Diarra et al. "Dickkopf-1 is a Master Regulation of Joint Remodeling," *Nat. Med.* 13(2):156-163, (Feb. 2007, e-pub. Jan. 21, 2007).
Durocher et al. "High-Level and High-Throughput Recombinant Protein Production by Transient Transfecton of Suspension-Growing Human 293-EBNA1 Cells," *Nucl. Acids. Res.* 30(2)(E9):1-9, 2002.
Geisse et al. "Eukaryotic Expression Systems: A Comparison," *Protein Expression and Purification* 8:271-282, (1996).
Genovese et al. "Combination therapy With Etanercept and Anakinra in the Treatment of Patients With Rheumatoid Arthritis Who Have Been Treated Unsuccessfully With Methotrexate," *Arthritis & Rheumatism* 50(5): 1412-1419, (May 2004).

(Continued)

*Primary Examiner* — Bridget E Bunner
*Assistant Examiner* — Fozia Hamud
(74) *Attorney, Agent, or Firm* — Morrison & Foerster LLP

(57) ABSTRACT

Bispecific tetravalent antibodies against IL-17 and TNFa, useful in therapy, e.g. the treatment of rheumatoid arthritis and other autoimmune diseases and/or to reduce pathological inflammatory conditions.

23 Claims, 30 Drawing Sheets
Specification includes a Sequence Listing.

(56) References Cited

OTHER PUBLICATIONS

Hellings et al. "Interleukin-17 Orchestrates the Granulocyte Influx into Airways After Allergen Inhalation in a Mouse Model of Allergic Asthma," *Am. J. Resp. Cell Mol. Biol.* 2003; 28:42-50, (2003).
Hueber et al. "Cutting Edge: Mast Cells Express IL-17A in Rheumatoid Arthritis Synovium," *J. Immunol.* 184(7):3336-3340, (2010, e-pub. Mar. 3, 2010).
Husby et al. "Synovial Localization of Tumor Necrosis Factor in Patients With Rheumatoid Arthritis," *J. Autoimmun.* 1(4):363-371, (Aug. 1988).
Kaufman. "Overview of Vector Design for Mammalian Gene Expression," *Mol. Biotechnol.* 16:151-160, (2000).
Keffer et al. "Transgenic Mice Expressing Human Tumour Ncrosis Factor: A Predictive Genetic Model of Arthritis," *EMBO J.* 10(13):4025-4031, (1991).
Kehlen et al. "Expression, Modulation and Signalling of IL-17 Receptor in Fibroblast-Like Synoviocytes of Patients With Rheumatoid Arthritis," *Clin. Exp. Immunol* 127:539-546, (2002).
Kobayashi et al. "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Koenders et al. "Tumor Necrosis Factor—Interleukin-17 Interplay Induces S100A8, Interleukin-1β, and Matrix Metalloproteinases, and Drives Irreversible Cartilage Destruction In Murine Arthritis," *Arthritis & Rheumatism* 63(8): 2329-2339, (Aug. 2011).
Kotake et al. "IL-17 in Synovial Fluids From Patients With Rheumatoid Arthritis is a Potent Stimulator of Osteoclastogenesis," *Clin. Invest.* 103( 9):1345-1352, (May 1999).
Li et al. "The Role of Interleukin-17 in Mediating Joint Destruction in Rheumatoid Arthritis," *Biochem. Biophys. Res. Comm.* 297:313-135, (Jun. 1, 2010).
Lu et al. "Di-Diabody: A Novel Tetravalent Bispecific Antibody Molecule by Design," *Journal of Immunological Methods* 279(1-2):219-232, (Aug. 1, 2003).
Makrides. "Components of Vectors for Gene Transfer and Expression in Mammalian Cells," *Protein Expr. Purif.* 17:183-202, (1999).
McInness et al. "The Pathogenesis of Rheumatiod Arthritis," *New England Journal of Medicine* 365(23):2205-2219, (Dec. 8, 2011).
Mitoma et al. "Infliximab Induces Potent Anti-inflammatory Responses by Outside-to-Inside Signals Through Transmembrane TNF-α," *Gastroenterology* 128(2): 376-392, (2005).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Nesbitt et al. "Mechanism of Action of Certolizumab Pegol (CDP870), In Vitro Comparison with Other Anti-tumor Necrosis Factor α Agents," *Inflamm. Bowel Dis.* 13(11): 1323-1332, (Nov. 2007).
Neuberger et al. "A Hapten-Specific chimaeric IgE Antibody With Human Physiological Effector Function," *Nature* 314:268-270, Mar. 1985).
Norderhaug et al. "Versatile Vectors for Transient and Stable Expression of Recombinant Antibody Molecules in Mammalian Cells," *J. Immunol. Methods* 204:77-87, (1997).
Orlandi et al. "Cloning Immunoglobulin Variable Domains for Expression by the Polymerase Chain Reaction," *Proc. Natl. Acad. Sci. USA* 86:3833-3837, May 1989).
Pace et. al. "How to Measure and Predict the Molar Absorption Coefficient of a Protein," *Protein Science* 4:2411-1423, (1995).
Pieringer et al. "Will Antirheumatic Treatment Improve Cardiovascular Outcomes in Patients with Rheumatoid Arthritis?," *Current Pharmaceutical Design* 20:486-495 , (2014).
Qi et al. "A Bispecific Antibody Against IL-1β and IL-17A is Beneficial for Experimental Rheumatoid Arthritis," *Int. Immunopharmacol.* 14(4):770-778, (2012, e-pub. Oct. 22, 2012).
Rajagopal et al. "A form of Anti-Tac(Fv) Which is Both Single-Chain and Disulfide Stabilized: Comparison With its Single-Chain and Disulfide-Stabilized Homologs ," *Prot. Engin.* 10(12):1453-1459, (1997).
Riechmann et al. "Reshaping Human Antibodies for Therapy," *Nature* 332:323-327, (Mar. 24, 1988).
Sadik et al. "IL-17RA Signaling Amplifies Antibody-Induced Arthritis," *PLoS One* 6(10)(326342):1-8, (Oct. 20, 2011).
Saxne et al. "Detection of Tumor Necrosis Factor α but not Tumor Necrosis Factor β in Rheumatiod Arthritis Synovial Fluid and Serum," *Arthritis & Rheumatism* 31(8):1041-1045, (Aug. 8, 1988).
Schaefer et al. "Immunoglobulin Domain Crossover as a Generic Approach for the Production of Bispecific IgG Antibodies," *Proc. Natl. Acad. Sci. USA* 108(27):11187-11192, (Jul. 5, 2011).
Schlaeger. "The Protein Hydrolysate, Primatone RL, is a Cost-Effective Multiple Growth Promoter of Mammalian Cell Culture in Serum-Containing and Serum-Free Media and Displays Anti-Apoptosis Properties," *J. Immunol. Methods* 194:191-199, (1996).
Schlaeger et al. "Transient Gene Expression in Mammalian Cells Grown in Serium-Free Suspension Culture," *Cytotechnology* 30:71-83, (1999).
Schmidt et al. "Supression of Metastasis Formation by a Recombinant Single Chain Antibody-Toxin Targeted to Full-Length and Oncogneic Variant EGF Receptors," *Oncogene* 18:1711-1721, (1999).
Shen et al. "Adalimumab Induces Apoptosis of Human Monocytes: A Comparative Study With Infliximab and Etanercept," *Aliment Pharmacol. Ther.* 21(3):251-258, (2005).
Ten Hove et al. "Infliximab Treatment Induces Apoptosis of Lamina Propria T Lymphocytes in Crohn's Disease," *Gut* 50:206-211, (2002).
Van Den Berg et al. "IL-17 as a Future Therapeutic Target for Rheumatoid Arthritis," *Nat. Rev. Rheumatol.* 5:549-553, (Oct. 2009).
Vijayalakshmi. "Antibody Purification Methods," *Appl. Biochem. Biotech.* 75:93-102, (1998).
Weinblatt et al. "Selective Costimulation Modulation Using Abatacept in Patients With Active Rheumatoid Arthritis While Receiving Etanercept: A Randomised Clinical Trial," *Ann.Rheum.Dis.* 66:228-234, (2007, e-pub. Aug. 25, 2006).
Werner et al. "Appropriate Mammalian Expression Systems for Bipharmaceuticals," *Arzeim. Drug Res.* 48(8):870-880, (1998).
Woodrick et al. "Anti-Interleukin-6 Therapy in Rheumatoid Arthritis," *Bulletin of the NYU Hospital for Joint Disease* 68(3):211-217, (2010).
Zhang et al. "Synergistic Effects of Interleukin-1β and Interleukin-17A Antibodies on Collagen-Induced Arthritis Mouse Model," *Int. Immunopharmacol.* 15(2):199-205, (2013, epub. Dec. 29, 2012).
Ziolkowska et al. "High Levels of IL-17 in Rheumatiod Arthritis Patients: IL-15 Triggers in Vitro IL-17 Production via Cyclosporin A-Sensitive Mechanism," *Journal of Immunology* 164(5):2832-2838, (2000).
International Search Report dated Nov. 3, 2014, for PCT Application No. PCT/EP2014/066581, filed on Aug. 1, 2014, 5 pages.
Written Opinion dated Nov. 3, 2014, for PCT Application No. PCT/EP2014/066581, filed on Aug. 1, 2014, 5 pages.
European Examination Report, Communication Pursuant to Article 94(3) EPC, dated Aug. 14, 2018, for European Patent Application No. 14747363.1, 6 pages.
Jang, Y.-J. et al. (Dec. 1998). "The Structural Basis for DNA Binding by an Anti-DNA Autoantibody," *Mol. Immunol.* 35(18):1207-1217.

* cited by examiner

FIG. 1B(1)
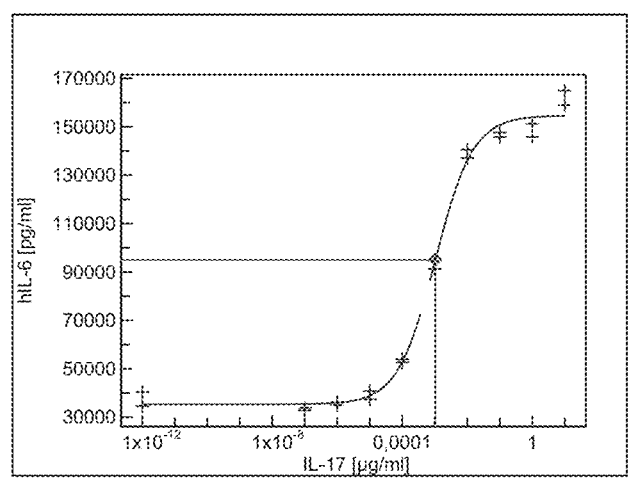
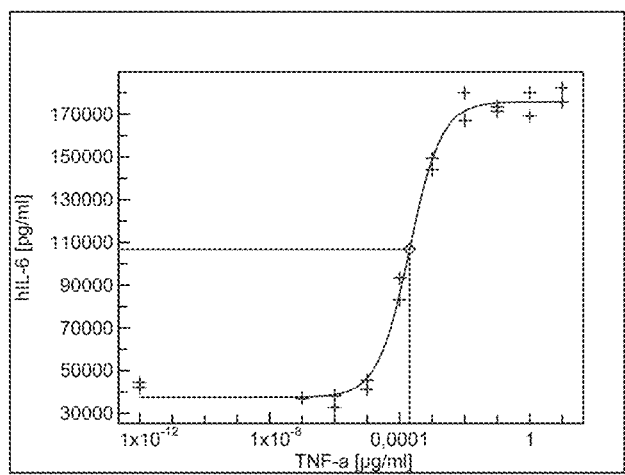

FIG. 1B(2)
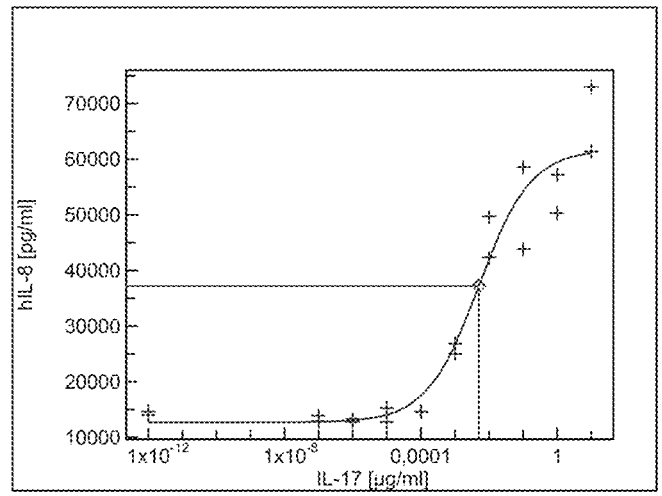
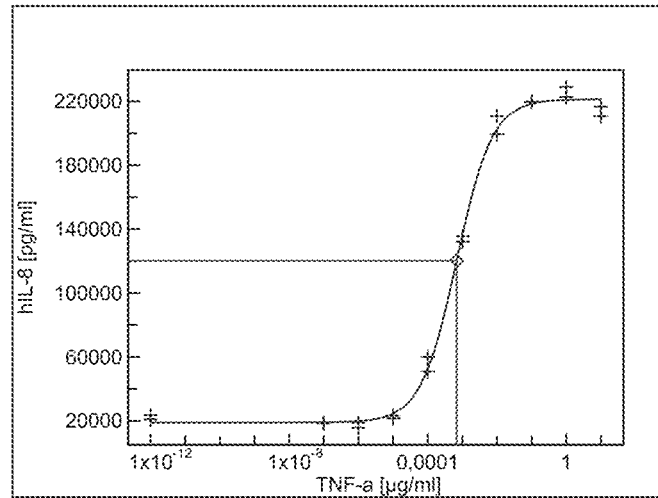

FIG. 1B(3)
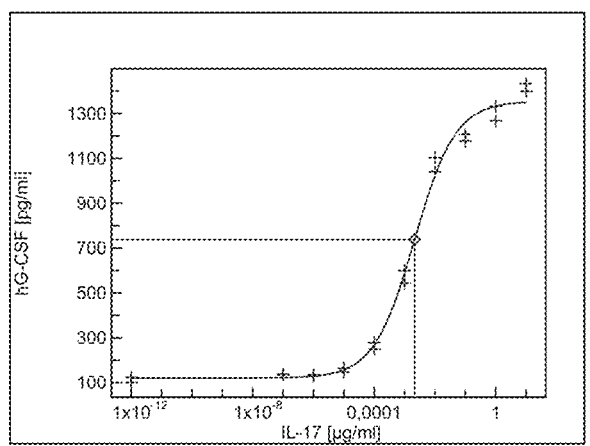
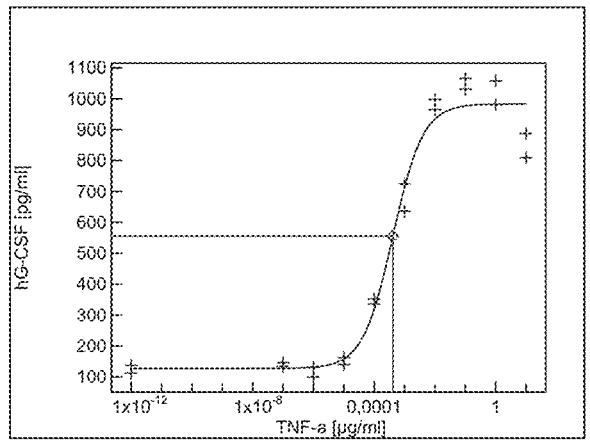

FIG. 1B(4)
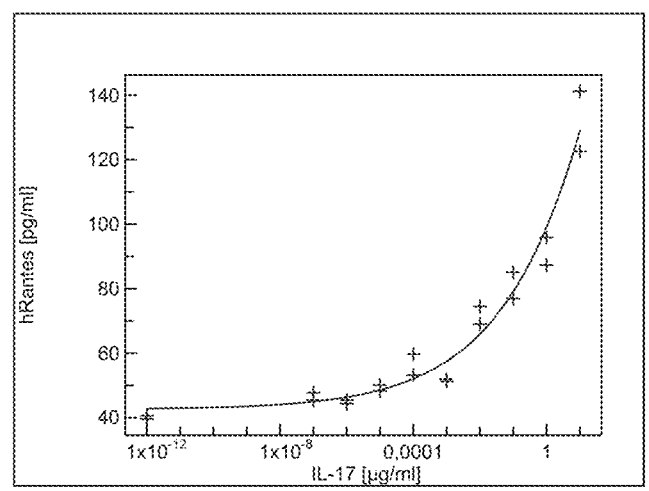
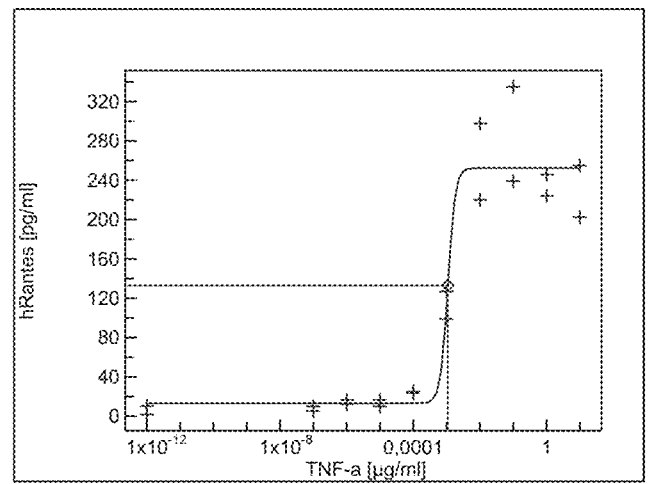

FIG. 1C(1)
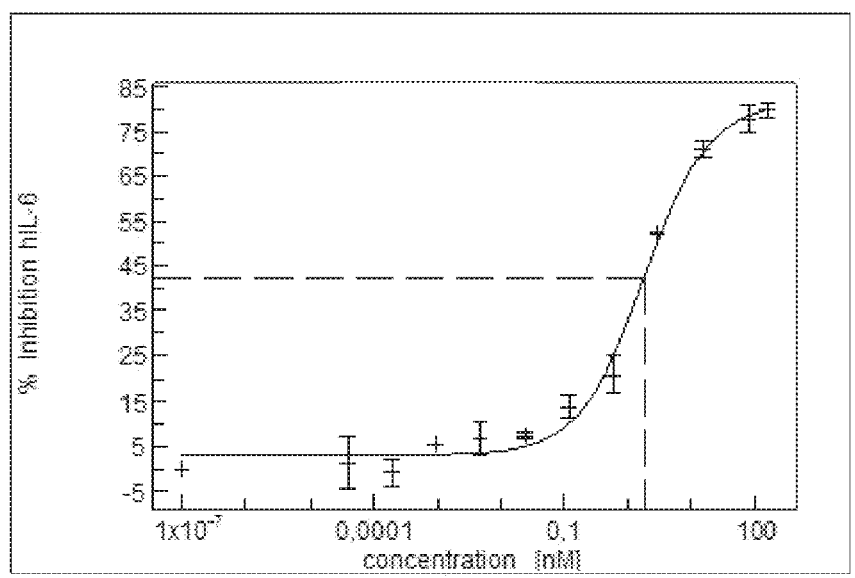
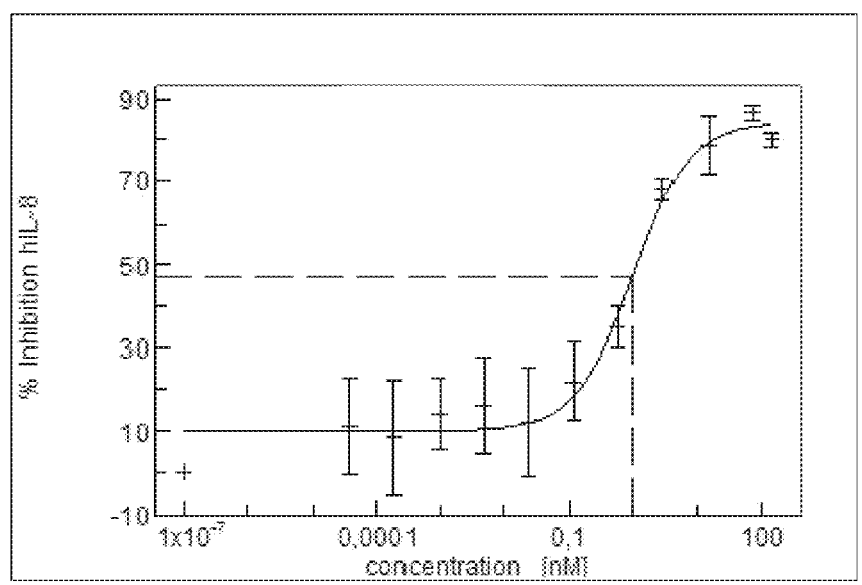

FIG. 1C(2)
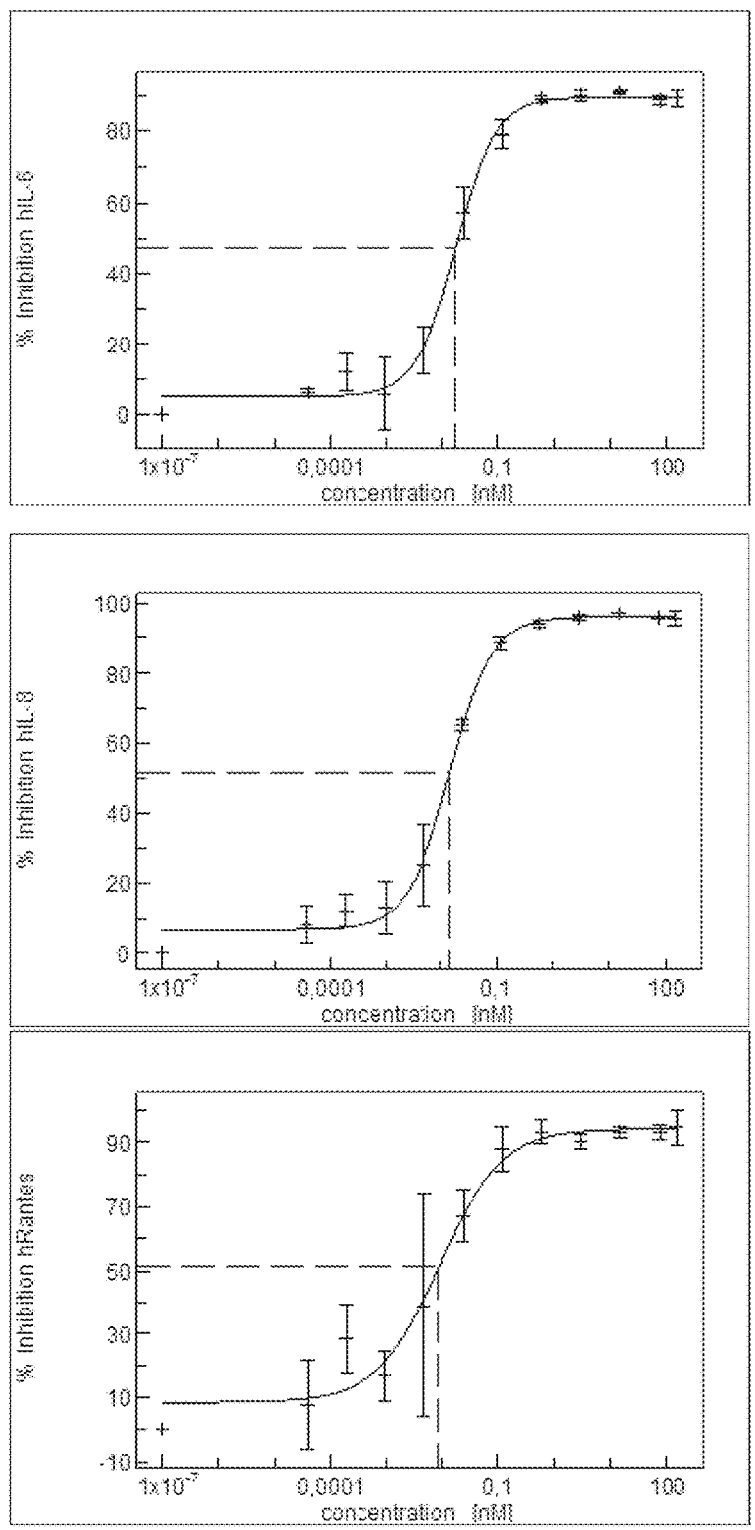

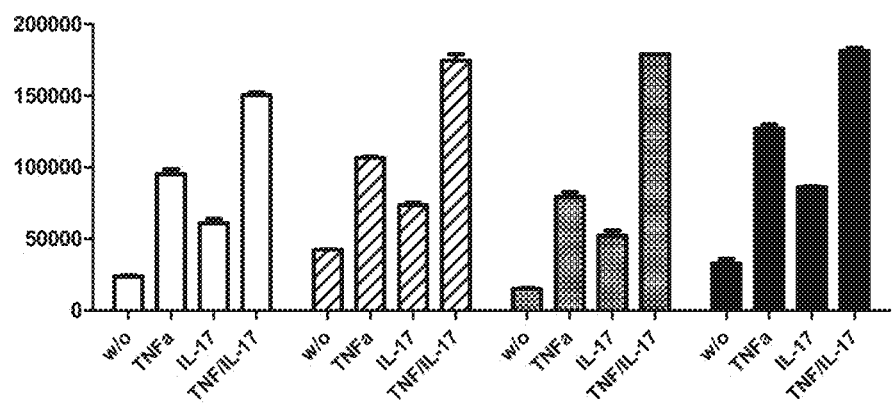
FIG. 2A(1)

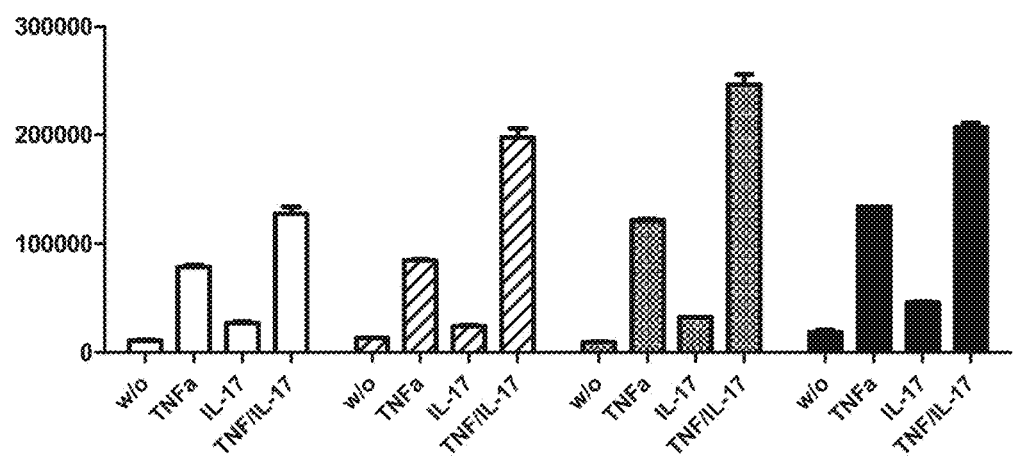
FIG. 2A(2)

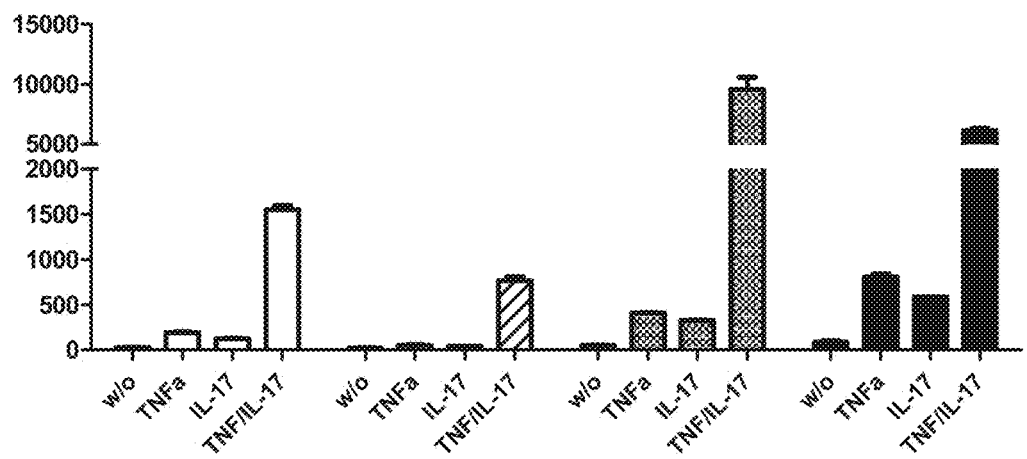
FIG. 2A(3)

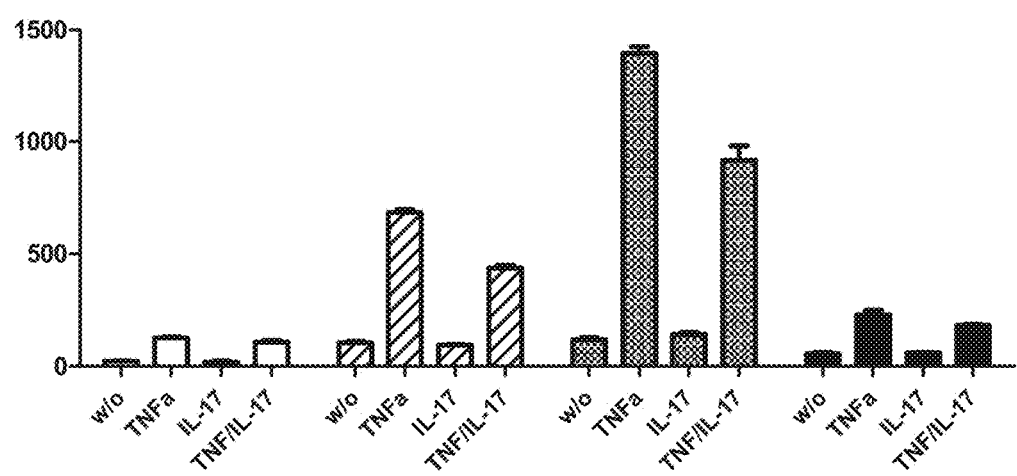
FIG. 2A(4)

FIG. 2B(1)
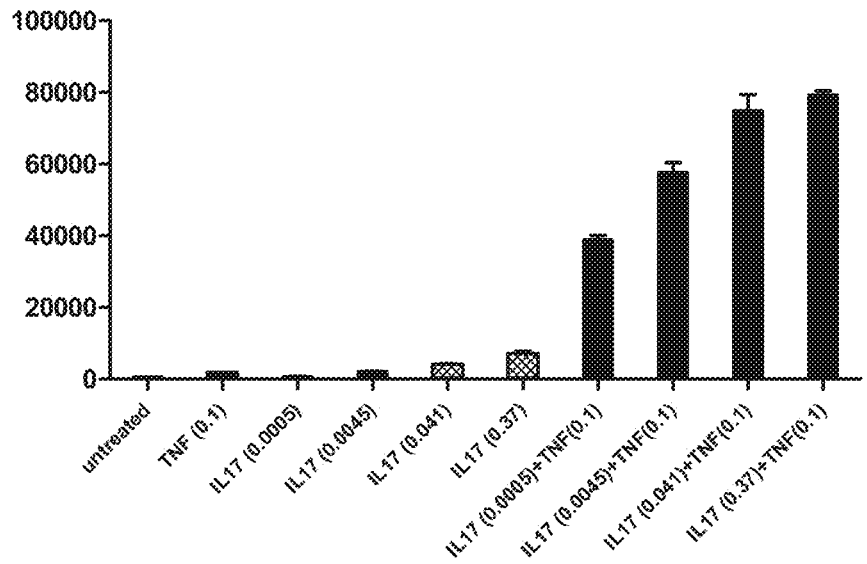
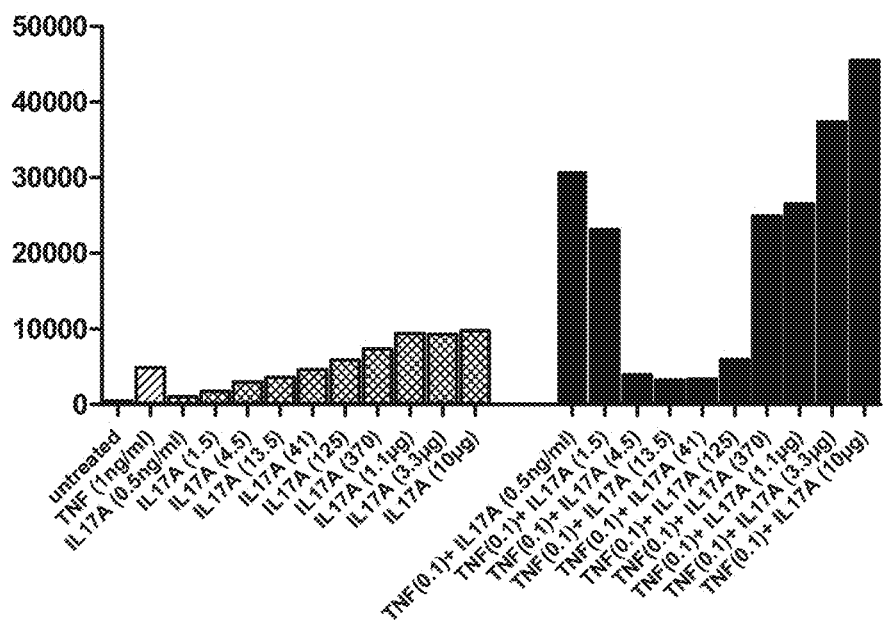

FIG. 2B(2)
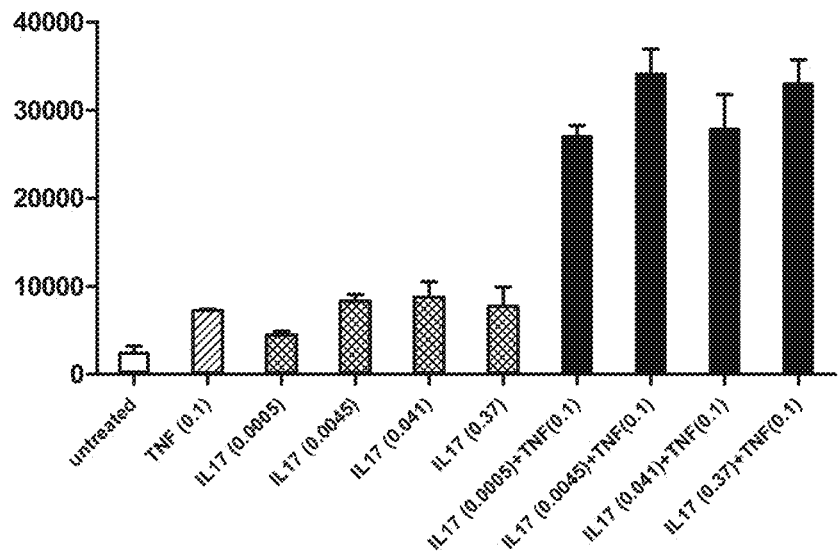
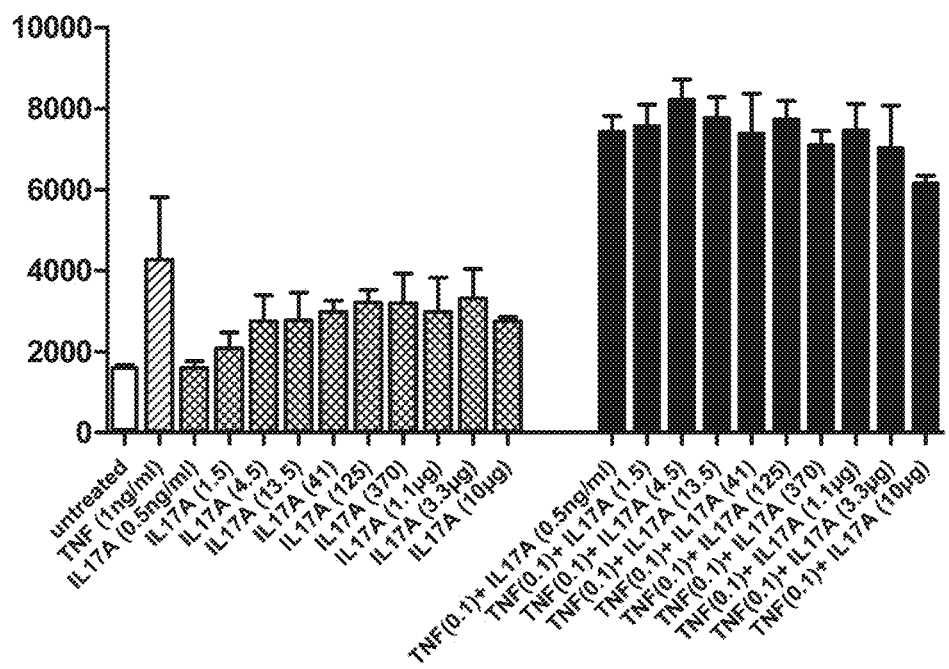

FIG. 2B(3)
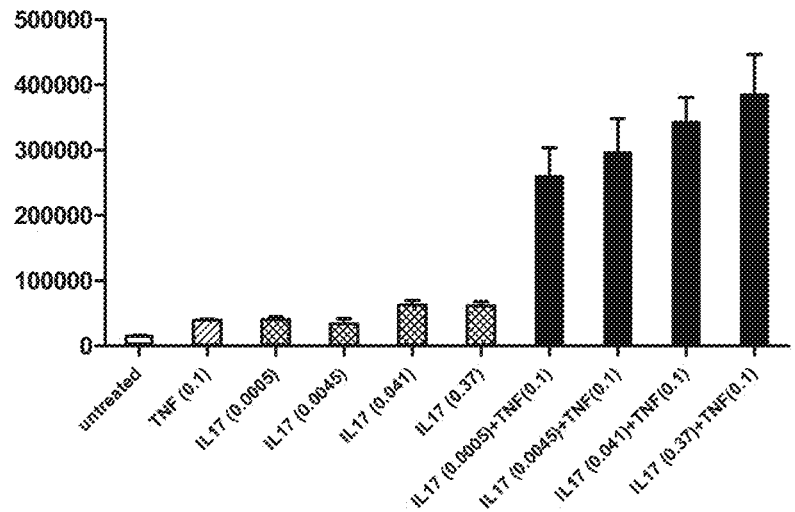
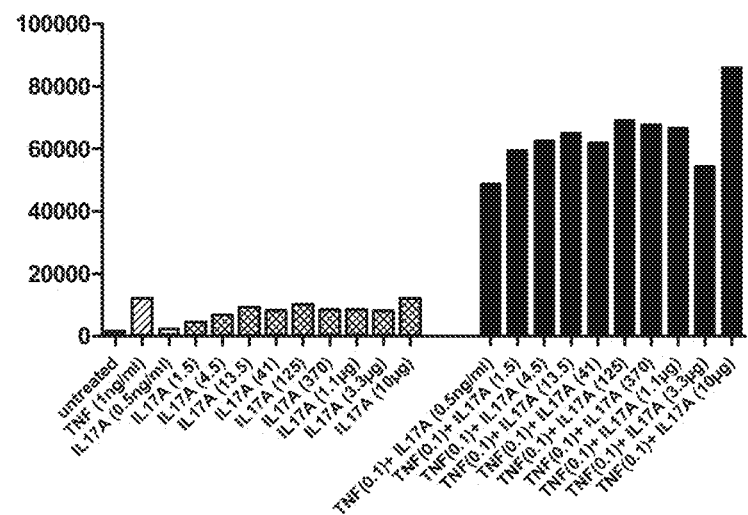

FIG. 2B(4)
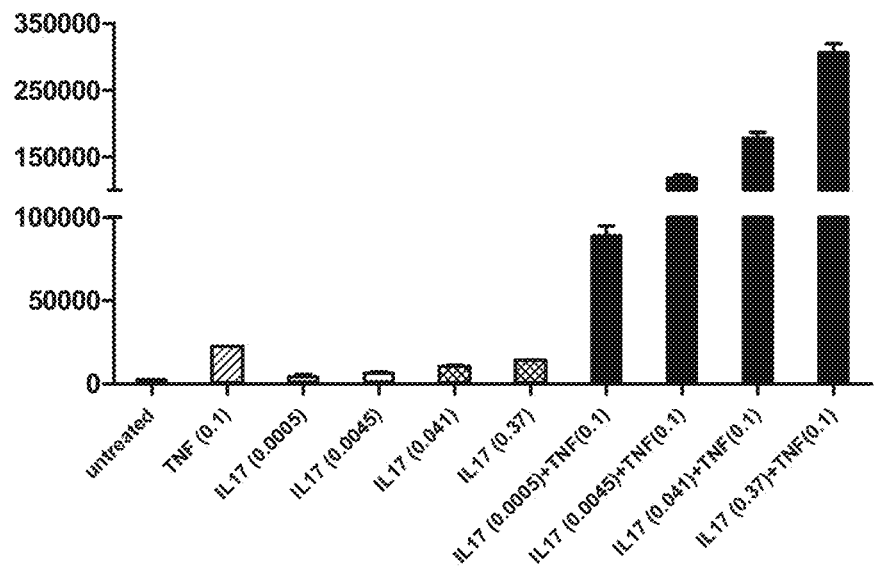
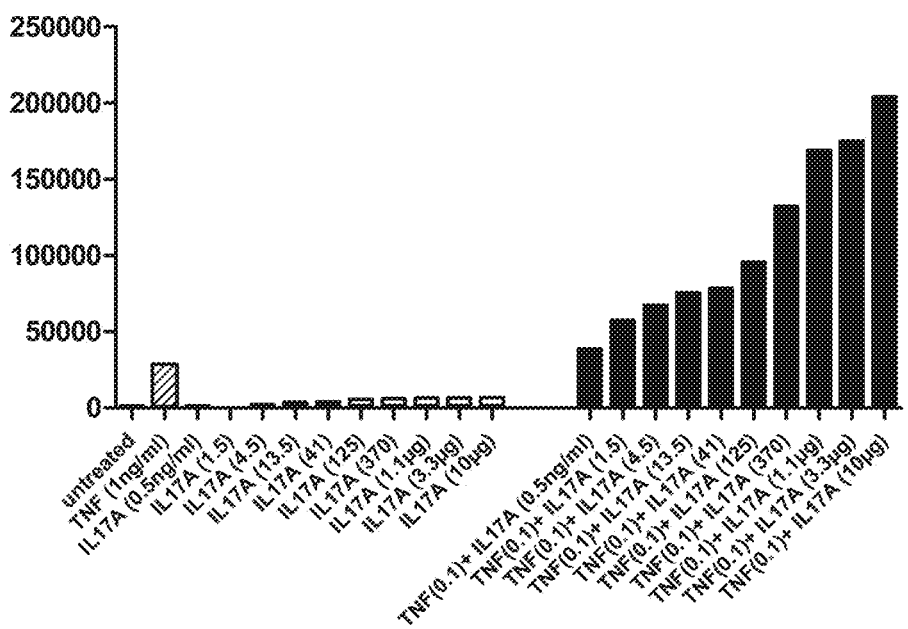

FIG. 2B(5)
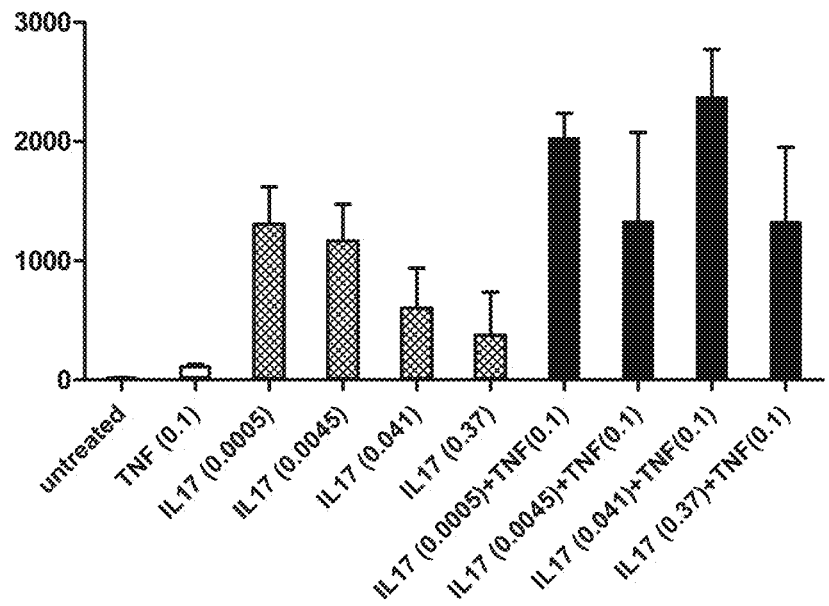
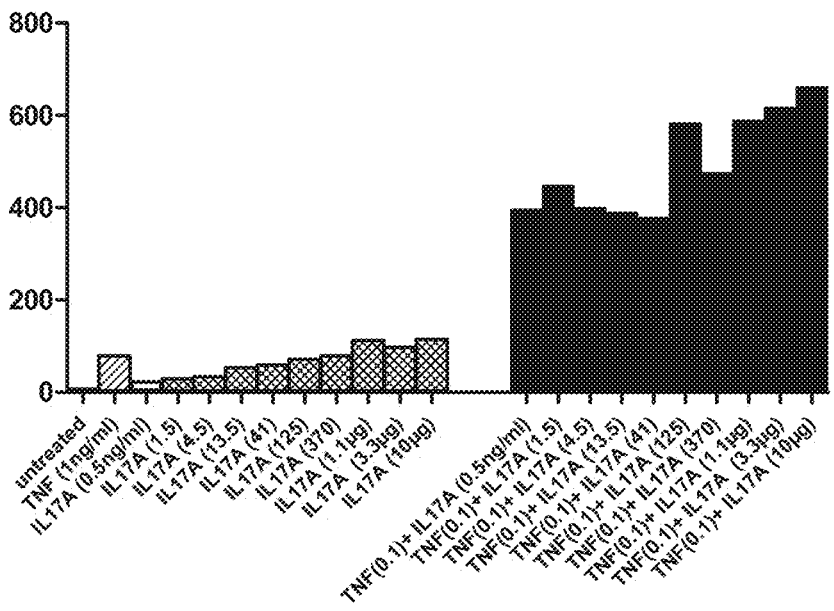

FIG. 2B(6)
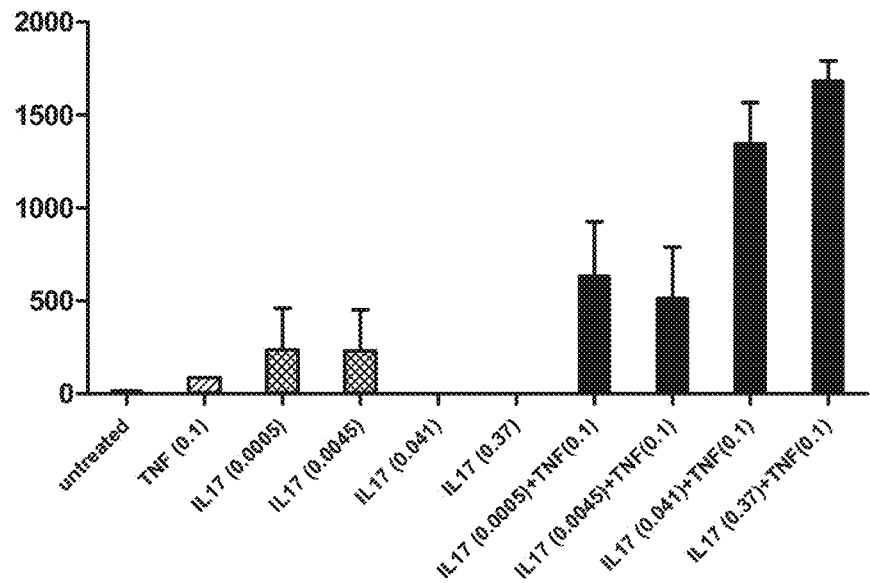
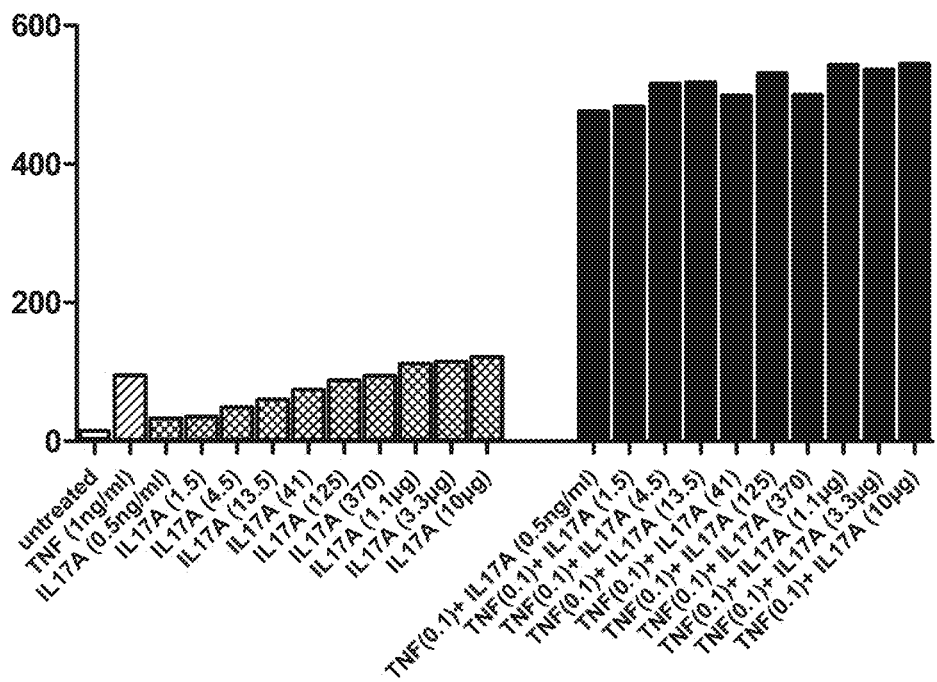

FIG. 2B(7)
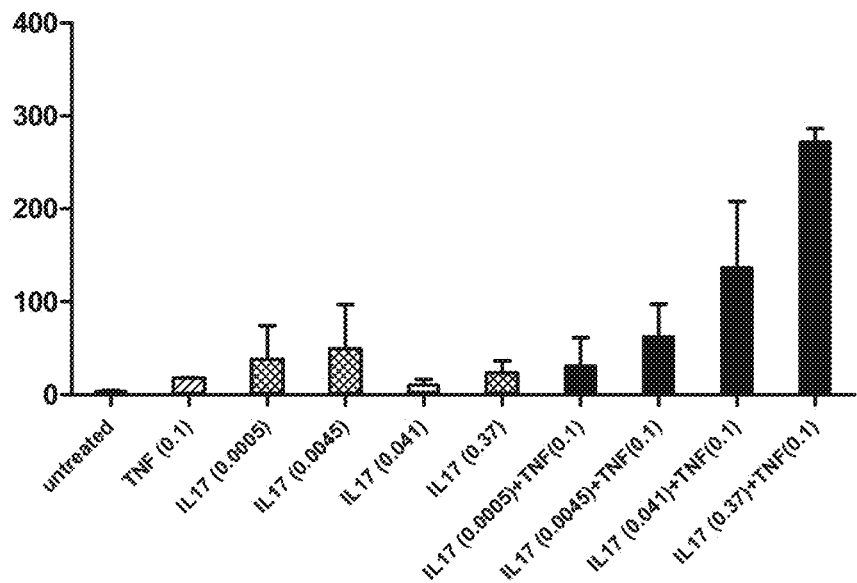
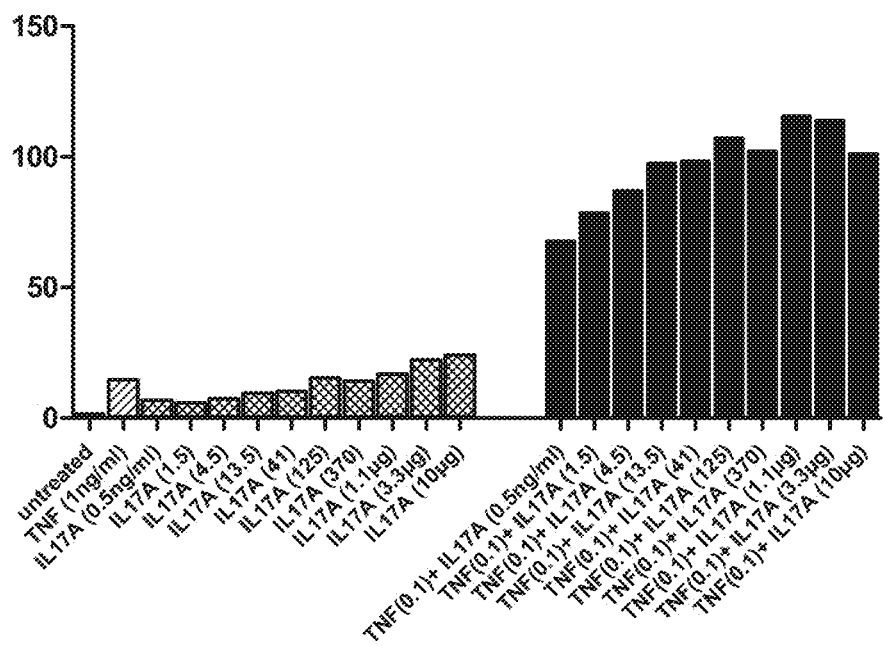

FIG. 2B(8)
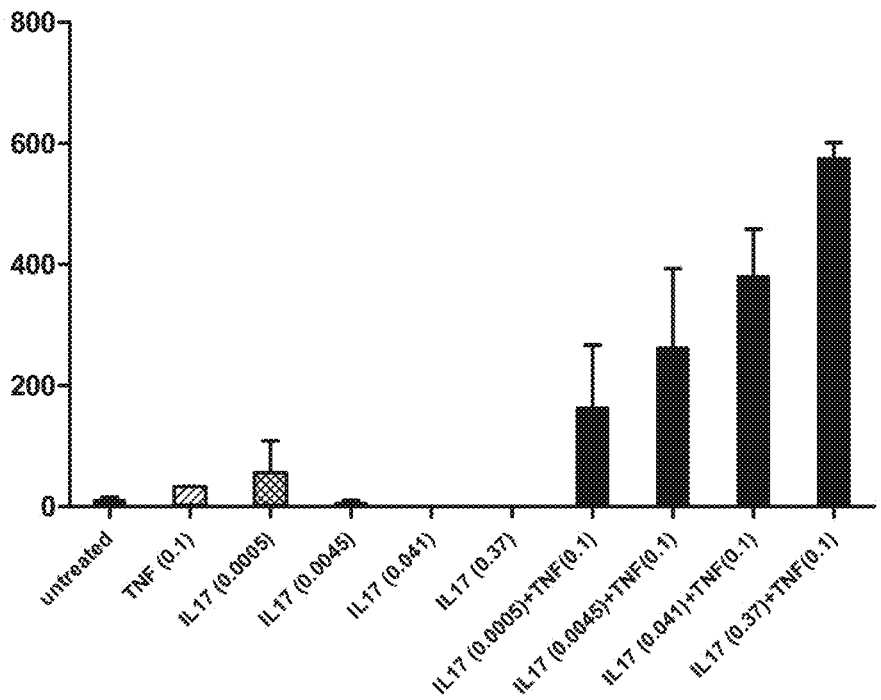
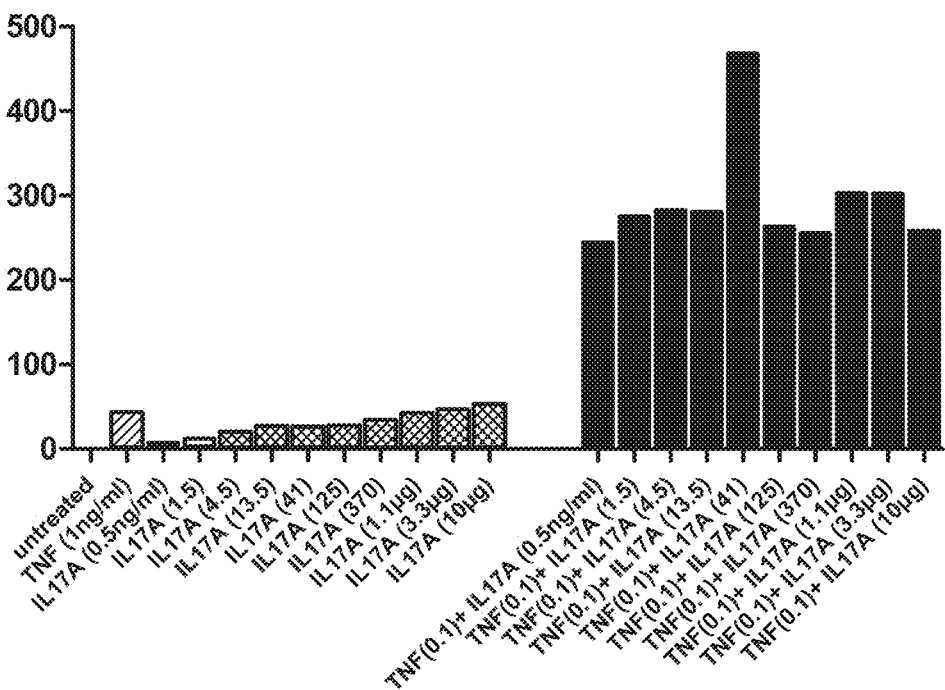

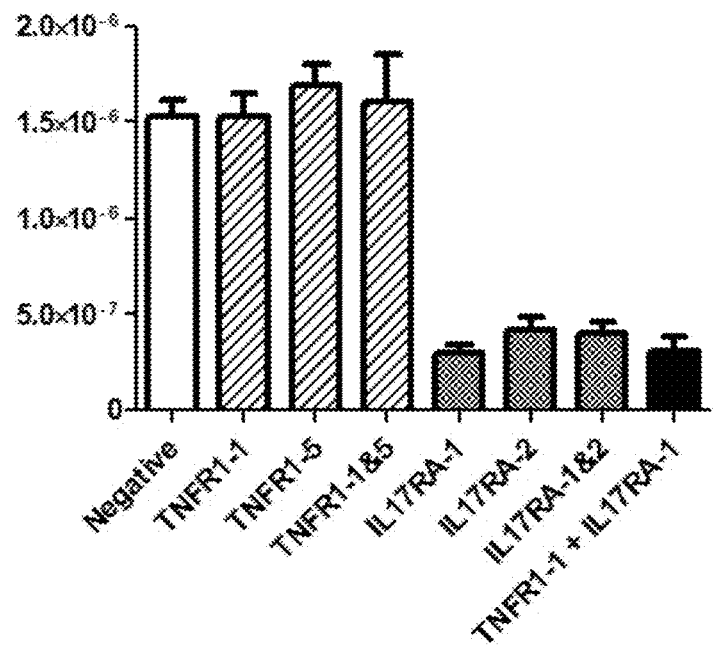
FIG. 3A(1)
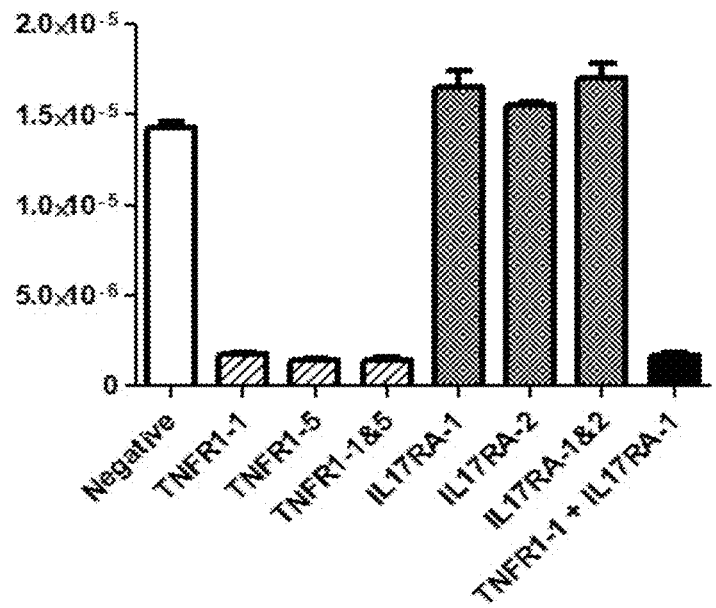
FIG. 3A(2)

FIG. 3B(1)
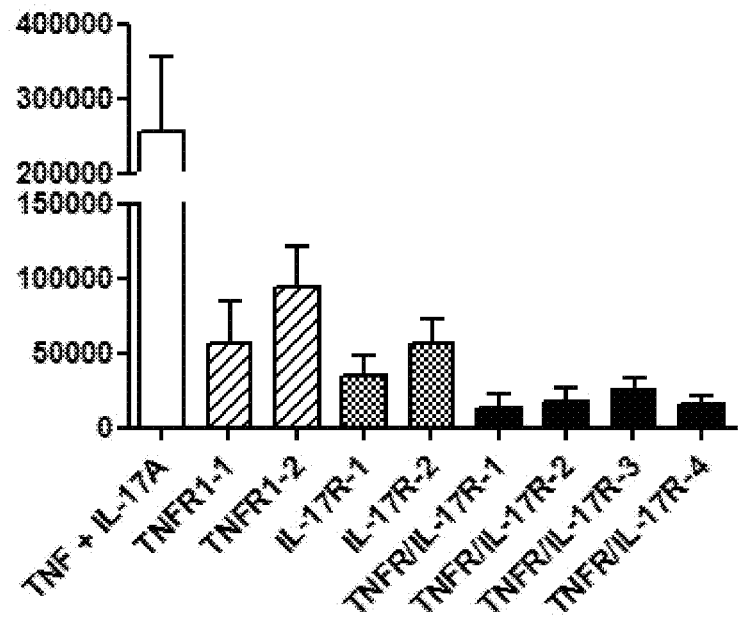
FIG. 3B(2)
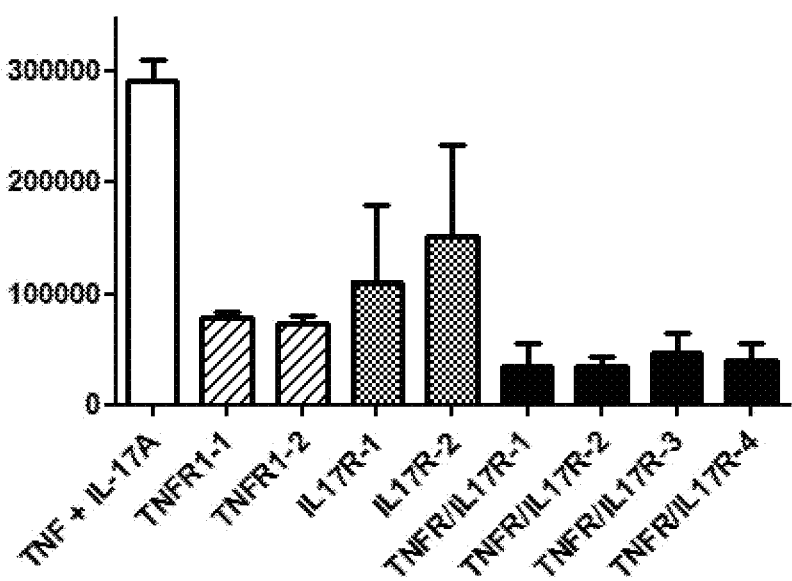

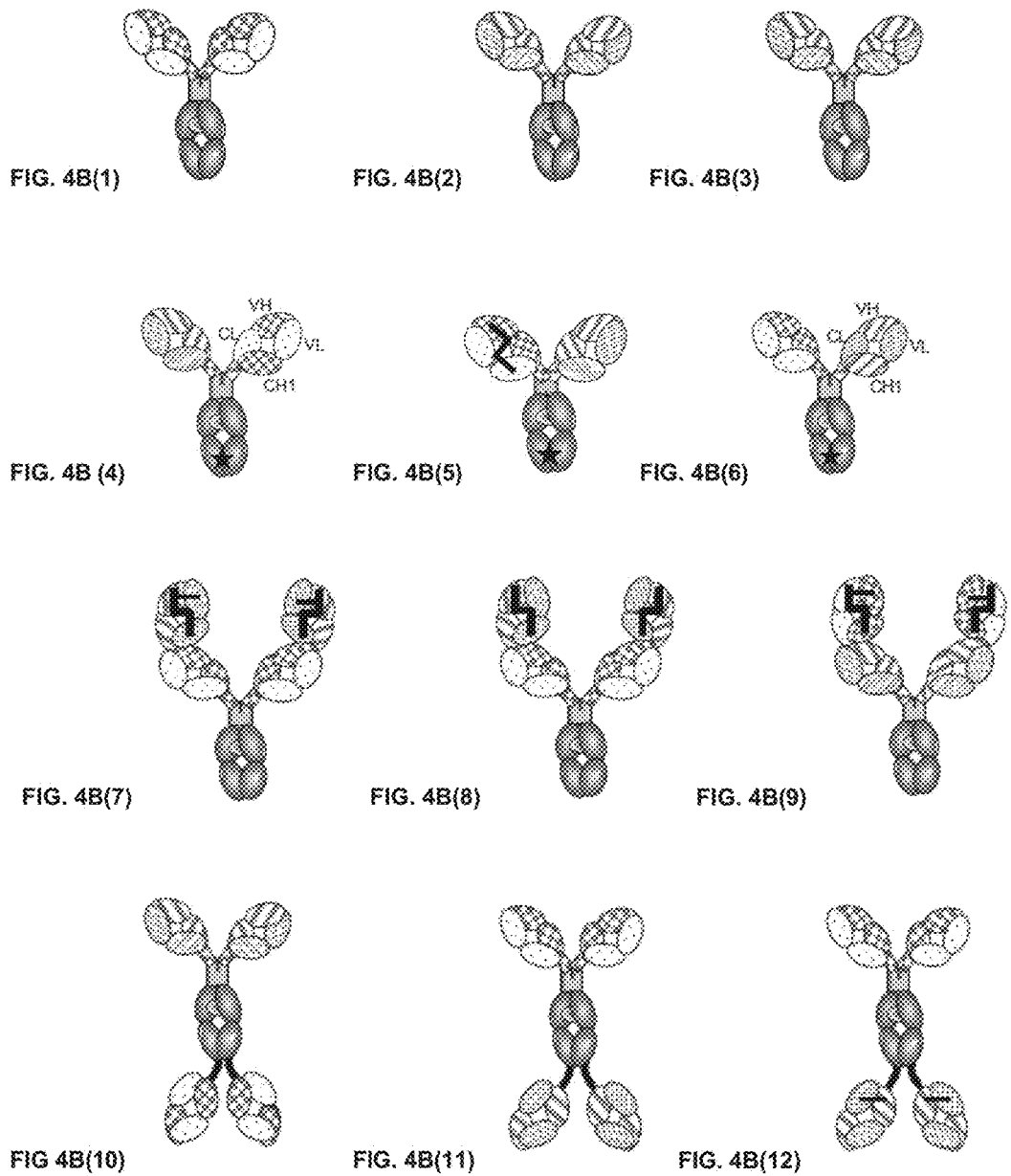

TNFA-IL-17 BISPECIFIC ANTIBODIES

CROSS REFERENCE TO RELATED APPLICATIONS

This application is a continuation of International Application No. PCT/EP2014/066581 having an international filing date of Aug. 1, 2014, the entire contents of which are incorporated herein by reference, and which claims benefit under 35 U.S.C. § 119 to European Patent Application No. 13178969.5 filed Aug. 1, 2013.

SEQUENCE LISTING

The instant application contains a Sequence Listing submitted via EFS-Web and hereby incorporated by reference in its entirety. Said ASCII copy, created on Jan. 26, 2016, is named P31597USSeqList.txt, and is 209,310 bytes in size.

FIELD OF THE INVENTION

The present invention relates to bispecific antibodies against human IL-17 and TNFa, and therapeutic uses thereof.

BACKGROUND TO THE INVENTION

Rheumatoid arthritis (RA), a disease of unknown etiology, is characterized by auto-immunity and autoantibodies, synovial inflammation and hyperplasia, cartilage and bone destruction, as well as systemic disorders, in particular impact on the cardiovascular system (McInness & Schett, NEJM 2011; Pieringer H et al., 2011). Multiple pathogenic mechanisms involving both innate and adaptive immunity are at play and contribute differentially in various phases of the disease, and conceivably in different patient subsets. However, no biomarker predicting progression is available yet.

Cytokines play a critical role in progression and control of the disease, as has been exemplified by successful therapy inhibiting key cytokines involved in the disease, such as TNFa and IL-6 or its receptor (Woodrick R et al., 2010). Their effects are pleiotropic and impact nearly all cell types involved in disease.

Tumour Necrosis Factor (TNF, also known as TNFa or TNFa) is a pro-inflammatory cytokine. TNFa plays a role in the induction of other inflammatory cytokines. Anti-TNFa therapy has a remarkable track record at improving RA and the safety of the therapy is well characterized (Canete & Pablos, 2013).

However, anti-cytokine therapies have limitations, for example upon anti-TNFa treatment approximately 40% of patients never respond, and only 20% of patients experience a major reduction in disease activity. Furthermore, many patients do not achieve remission and most lose their response to anti-TNFa therapies within two to three years. IL-6R inhibition bears the promise to show incremental activity and provide additional benefit (Ash et al., 2012).

In view of the above, there is a large unmet clinical need for treatments regarding a more effective suppression of inflammation and halting, or even reversing, disease progression and joint destruction. The ultimate goal is sustained remission for a greater number of patients in RA.

Given the heterogeneity and dynamic nature of the human autoimmune diseases, including redundancy of molecular pathways, it is likely that one will need to perturb multiple redundant and distinct mechanisms to achieve greater and/or broader therapeutic efficacy. Current therapies inhibiting cytokines (Atzeni & Sarzi-Puttini, 2009) or T cell activation are already by themselves immunosuppressive, and combination of the same may lead to unacceptable increase of infection related side effects. This has been shown for e.g. a combination of CTLA-4-Ig and anti-TNFa (Weinblatt, 2007), or anti-TNFa and IL-1RA (Genovese et al., 2004). It is therefore important to identify treatment combinations susceptible to have a major effect on disease, without significantly increasing the risk of side effects.

Interleukin-17 (IL-17, also known as IL-17A) is, like TNFa, a pro-inflammatory cytokine. IL-17 plays a role in the induction of other inflammatory cytokines and chemokines. IL-17 has emerged as a cytokine involved in multiple auto-immune diseases, thought to amplify inflammation and to contribute to chronic tissue destruction and remodelling. IL-17 is produced not only by the Th17 T-helper cell subset, but also among others such as mast cells, which may play a crucial role in RA (Hueber A J, J Immunol 2010). In contrast, the IL-17A receptor (IL-17R) is ubiquitously expressed and signalling via IL-17R drives cytokine, chemokine and prostaglandin secretion from fibroblasts, endothelial and epithelial cells as well as increasing expression of cell adhesion molecules. IL-17 also induces TNFa and IL-1 secretion from macrophages, amplifying inflammation and tissue destruction. Finally, by inducing RANKL, IL-17 is thought to have a major impact on osteoclastogenesis and hence bone destruction (Kehlen et al., 2002; Li et al., 2010; Sadik et al, 2011; van den Berg & Miossec, 2009).

IL-17 neutralizing antibodies reduce severity and incidence of mouse RA model of collagen induced arthritis, and high levels of IL-17A can be detected in the synovial fluid of inflamed joints from RA patients (Ziolkowska et al.; Kotake et al.; Hellings et al.). Current clinical experience with anti-IL-17 antibodies suggests that the level of immunosuppression may be manageable, which make it attractive for combinations with other therapies (Koenders et al).

SUMMARY OF THE INVENTION

The inventors assessed the role of TNFa and IL-17 in combination on two major cell types involved in RA, measuring their impact on inflammation (shown by cytokine secretion in vitro in RA-fibroblast like synoviocytes) and on the potential for tissue destruction (as measured by matrix metallo-protease secretion in vitro by chondrocytes) and showed that these cytokines in combination can exert a synergistic effect on inflammation.

The present invention relates to bispecific tetravalent antibodies against human IL-17 and TNFa, methods of producing such antibodies and therapeutic uses of such antibodies.

The bispecific tetravalent antibodies of the invention have four antigen binding sites: two binding sites for IL-17 and two binding sites for TNFa. The antibodies are therefore bivalent for IL-17 and bivalent for TNFa. Antibodies having two binding sites for IL-17 and two binding sites for TNFa are be referred to herein as having a "2+2" format.

The antibodies of the invention may have a "2+2 Cross-Mab" format (for example, see FIGS. 4A and 4D). Alternatively, the antibodies of the invention may have a "2+2 scFab" format (for example, see FIGS. 4A and 4C).

The antibodies of the invention may have high stability, meaning that they are relatively resistant to aggregation. This high stability means that the antibodies of the invention are suitable for formulation at high concentrations. Since high concentration antibody formulations are useful for subcutaneous administration, the antibodies of the invention are particularly useful for formulations for subcutaneous administration.

The antibodies of the invention may be inhibitors of inflammatory cytokine production. In particular, the antibodies may be inhibitors of inflammatory cytokine production and/or matrix metalloproteinase (MMP) production induced by simulation with IL-17, induced by simulation with TNFa, or induced by stimulation with IL-17 and TNFa in combination. The antibodies may be inhibitors of the production of inflammatory cytokines such as IL-6, IL-8, G-CSF and RANTES by cells such as fibroblast-like synoviocytes (FLS) as well as cytokines and MMPs by chondrocytes.

The antibodies of the invention are useful for treating or preventing rheumatoid arthritis or other inflammatory disorders such as Psoriasis, Lupus (systemic lupus erythematodes, SLE, or lupus nephritis), ankylosing spondylitis, Crohn's disease, ulcerative colitis and juvenile idiopathic arthritis, and general inflammatory diseases (e.g. conjunctivitis). The antibodies may be particularly useful in treating or preventing rheumatoid arthritis in patients exhibiting elevated TNFa and/or IL-17. The antibodies may be useful in treating or preventing rheumatoid arthritis in patients who are non-responsive to anti-TNFa treatment.

The invention provides uses of the antibodies described herein for treating or preventing rheumatoid arthritis. The invention provides use of the antibodies described herein for the treatment or prevention of rheumatoid arthritis in patients exhibiting elevated TNFa and/or IL-17 or in patients who have been determined to have elevated TNFa and/or IL-17. The invention also provides use of the antibodies described herein for treating or preventing rheumatoid arthritis in patients who are non-responsive to anti-TNFa treatment.

The invention further provides use of the antibodies described herein for preventing or reducing rheumatoid arthritis. The invention further provides use of the antibodies described herein for preventing or reducing an inflammatory disorder such as Psoriasis, Lupus (systemic lupus erythematodes, SLE, or lupus nephritis), ankylosing spondylitis, Crohn's disease, ulcerative colitis and juvenile idiopathic arthritis, and general inflammatory diseases (e.g. conjunctivitis).

The invention provides antibodies as described herein for use in a method of treatment. The invention also provides antibodies as described herein for use in a method of treating or preventing rheumatoid arthritis in a patient. The patient may have elevated TNFa and/or IL-17. The invention further provides antibodies as described herein for use in a method or treating a patient to prevent or reduce inflammatory disorders such as Psoriasis, Lupus (systemic lupus erythematodes, SLE, or lupus nephritis), ankylosing spondylitis, Crohn's disease, ulcerative colitis and juvenile idiopathic arthritis, and general inflammatory diseases (e.g. conjunctivitis).

Fibroblast-like synoviocytes (FLS), obtained from both normal donors and RA patients (Cell Applications Inc.) were cultured under subconfluent conditions ($5\times10^5$ cells/w). On the next day, cells were detached (Accutase) and stained with antibodies against human TNFRI (BD Biosciences; cat. no. #550900), human CD217 (BioLegend; cat. no. #340903) (open histograms) or appropriate isotype controls (filled histograms). Top panels show expression of CD120a (TRNFRI) on FLS in normal donors (left panel) and RA patients (right panel). Lower panels show expression of CD217 (IL-17A-R) on FLS in normal donors (left panel) and RA patients (right panel). Shown is one representative example of two independent experiments using FLS from up to five different donors. (BD Biosciences; cat. no. #550900) IL-17 (BioLegend; cat. no. #340903).

FIG. 1B(1), FIG. 1B(2), FIG. 1B(3), and FIG. 1B(4)—Cytokine profile of RA-FLS in response to IL-17 or TNFa stimulation in vitro (agonist response curves).

$2\times10^4$ RA-FLS/well (96-flat bottom) were pre-cultured for two days in Synoviocyte Growth Medium (Cell Applications; 5% $CO_2$) before indicated amounts of TNFa or IL-17 were added in fresh medium. After 72 hours, supernatant was analyzed for production of various cytokines (see details below) by CBA technology (BD Biosciences). Shown is the mean of duplicates per each concentration and stimulus. Curves reflect a typical result of at least five representative experiments reproduced with different RA-FLS donors. In parallel experiments, FLS obtained from healthy donors were used (data not shown).

FIG. 1B(1) shows results for the cytokine IL-6 on addition of IL-17A (top panel–EC50=1.0 ng/ml) or TNFa (lower panel–EC50=0.2 ng/ml).

FIG. 1B(2) shows results for the cytokine IL-8 on addition of IL-17A (top panel–EC50=5.0 ng/ml) or TNFa (lower panel –0.68 ng/ml)

FIG. 1B(3) shows results for the cytokine G-CSF on addition of IL-17A (top panel–EC50=2.1 ng/ml) or TNFa (lower panel –0.4 ng/ml).

FIG. 1B(4) shows results for the cytokine RANTES on addition of IL-17A (top panel) or TNFa (lower panel–EC50=1.1 ng/ml).

FIG. 1C(1) and FIG. 1C(2)—Inhibition curves of IL-17 or TNFa induced cytokine production in RA-FLS by titration of specific antibodies in vitro.

Figure 1A:
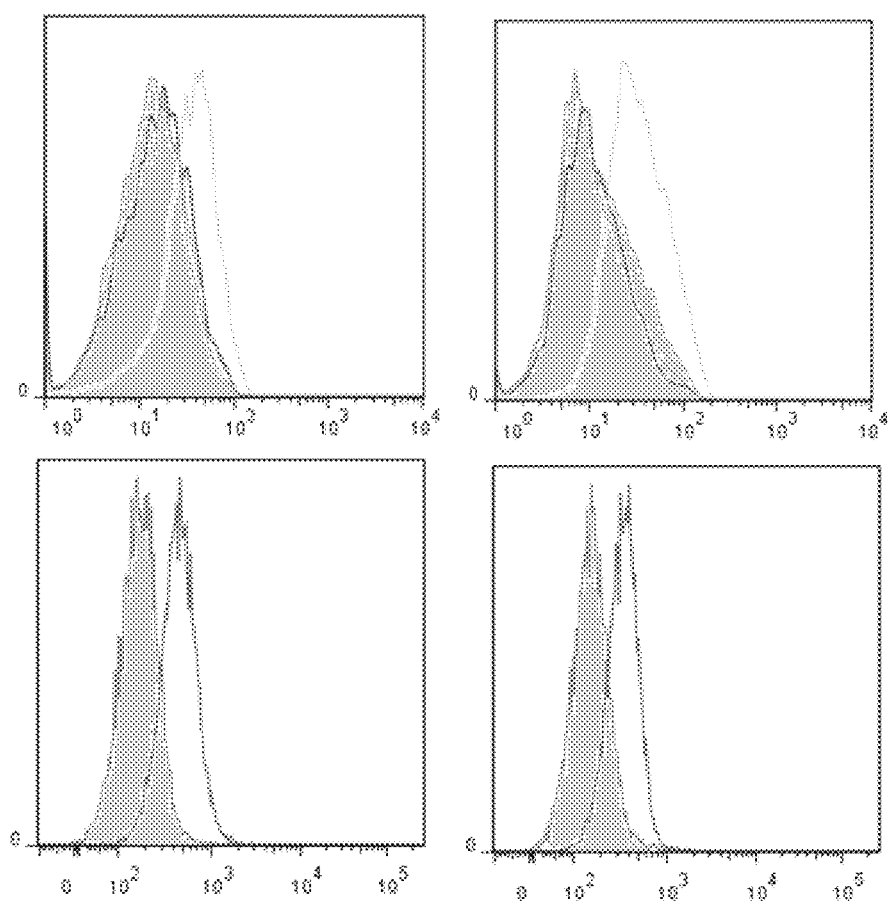
FIG. 1A—Expression of human TNFa receptor type I (TNFRI, CD120a) and IL-17 receptor (CD217) on normal and RA fibroblast-like synoviocytes.

RA-FLS were cultured as described in FIG. 1A. Shown is the inhibition of IL-6 (top panel of FIG. 1C(1) (IC50=1.830 nM) and top panel of 1C(2) (IC50=0.018 nM), IL-8 (second panel of FIG. 1C(1) (IC50=0.983 nM) and FIG. 1C(2) (IC50=0.014 nM), and optionally RANTES (1C(2) lower panel (IC50=0.009 nM) production after IL-17A (FIG. 1C(1)) or TNFa (FIG. 1C(2)) stimulation by addition of an in-house generated IL-17A antibody, #134, or Adalimumab, respectively. Antibodies were titrated form 0-150 nM resulting in a dose-dependent of cytokine production compared to the untreated samples. Shown is the mean relative inhibition derived from duplicates per each concentration and stimulus and in addition the IC50 values. Given is one exemplary experiment out of three independent experiments using four different RA-FLS donors.

FIG. 1D TNFa but not IL-17 dependent upregulation of ICAM-1 (CD54) expression on human fibroblast-like synoviocytes.

Fibroblast-like synoviocytes were cultured as described before for 24 hrs alone (black bars) or in the presence of indicated stimuli (100 ng/ml LPS (Sigma #L3129) (open bars), 10 ng/ml IL-17A (PeproTech #200-17) (dotted bars) or 1 ng/ml TNFa (R&D Systems #1090-TW/CF) (hatched bars)). Shown is the expression (mean fluorescence intensity) of ICAM-1 on FLS from healthy donors and RA patients and also peripheral blood monocytes. Briefly, after incubation cells were detached by a short Accutase treatment, stained with an ICAM-1 specific mAb (BD Biosciences #555511) or an appropriate isotype control mAb before subjection to FACS analysis on a FACS CANTO II.

FIG. 2A(1), FIG. 2A(2), FIG. 2A(3), and FIG. 2A(4)—In vitro effect of single or combined IL-17 and/or TNFa stimulation on RA-FLS cytokine production.

RA-FLS were cultured as mentioned before and incubated with IL-17, TNFa or combination (1 ng/ml each) before production of IL-6, IL-8, G-CSF and RANTES was assessed after 24 hrs. Shown is the mean of duplicates from one representative experiment out of four different donors (open/hatched/dotted/solid bars).

FIG. 2A(1) shows IL-6 production.
FIG. 2A(2) shows IL-8 production.
FIG. 2A(3) shows G-CSF production.
FIG. 2A(4) shows RANTES/CCL5 production.

FIG. 2B(1), FIG. 2B(2), FIG. 2B(3), FIG. 2B(4), FIG. 2B(5), FIG. 2B(6), FIG. 2B(7), and FIG. 2B(8)—Synergistic effect of IL-17 and TNFa induced chemokine/MMP production in normal and RA patient derived human primary chondrocytes.

$10^4$ human articular chondrocytes (derived from normal donors or RA patients) were plated and incubated with suboptimal concentrations of IL-17 (40 ng/ml), TNFa (0.1 ng/ml), or combinations of IL-17+TNFa. 24 hrs later, supernatants were collected and subjected to cytokine, chemokine and MMP analysis (using multiplex set from Aushon Bio-Systems).

FIG. 2B(1) shows results for IL-8.
FIG. 2B(2) shows results for MCP-1.
FIG. 2B(3) shows results for MMP-1.
FIG. 2B(4) shows results for MMP-3.
FIG. 2B(5) shows results for MIP-1a.
FIG. 2B(6) shows results for CCL1.
FIG. 2B(7) shows results for CCL17.
FIG. 2B(8) shows results for CCL22.

FIG. 3A(1) and FIG. 3A(2)—IL-17R and TNFRI expression and Taqman® analysis of gene knockdown after single or dual targeting in RA-FLS. Pre-designed short interfering RNA (siRNA) for TNFR (SI00021462 and SI00301945) or IL-171L-17R (Qiagen, SI00104986 and SI03114328) were used to alter expression in RA-FLS. For siRNA transfections, Lipofectamine RNAi Max (Invitrogen)/siRNA mixtures were prepared in Optimem (Invitrogen) such that final concentrations were 2.5 µl/ml and 20 nM respectively. All siRNA solutions targeting a single gene were mixed at a 1:1 ratio (M:M) with All Stars Negative control (Qiagen, SI03650318). All dual targeting mixtures were also at a 1:1 ratio (M:M). Comparisons were made to cells transfected with All Stars Negative control (Negative). RA-FLS were added to the complexes in basal media containing 1% (v/v) FBS for 48 hours prior to lysis. Total RNA was extracted using the RNeasy plus Mini kit and then transcribed to cDNA using AffinityScript QPCR cDNA Synthesis Kit. qPCR reactions were performed on an Mx3000P™ Real-Time PCR System (Agilent Technologies Inc., Santa Clara, Calif., USA). The resulting amplification and melt curves were analyzed to ensure specific PCR product. Threshold cycle (CT) values were used to calculate the fold change in transcript levels. IL-17R and TNFR1 expression levels were determined to ensure specificity of single or dual targeting mixtures.

FIG. 3A(1) shows results for IL-17R.
FIG. 3A(2) shows results for TNFRI.

FIG. 3B(1) and FIG. 3B(2)—S2B IL-6 and MMP-3 production in TNFa:IL-17 stimulated RA-FLS and reduction after single or dual target knockdown in stimulated cells.

Pre-designed short interfering RNA (siRNA) for IL-171L-17R or TNFRI were used to alter expression in RA-FLS. For siRNA transfections, Lipofectamine RNAi Max (Invitrogen)/siRNA mixtures were prepared in Optimem (Invitrogen) such that final concentrations were 2.5 µl/ml and 20 nM respectively. All siRNA solutions targeting a single gene were mixed at a 1:1 ratio (M:M) with All Stars Negative control (Qiagen, SI03650318). All dual targeting mixtures were also at a 1:1 ratio (M:M). All data was compared to cells transfected with All Stars Negative control in the presence of stimulus. RA-FLS were added to the complexes in basal media containing 1% (v/v) FBS for 48 hours prior to stimulation IL-17A/Tweak mixtures made up and added to the transfected cultures such that final concentrations were 100 ng/ml and 1 µg/ml respectively. After a further 24 hours, supernatant was harvested and cytokine levels analyzed. IL-6 or MMP3 levels were assessed using a standard alphaLISA kit (Perkin-Elmer) according to the recommended protocol. All measurements were conducted using a PHERAstarPLUS luminescence microplate reader (BMG Labtech Inc., Cary, N.C., USA).

FIG. 3B(1) shows results for IL-6.
FIG. 3B(2) shows results for MMP-3.

Figure 4A:
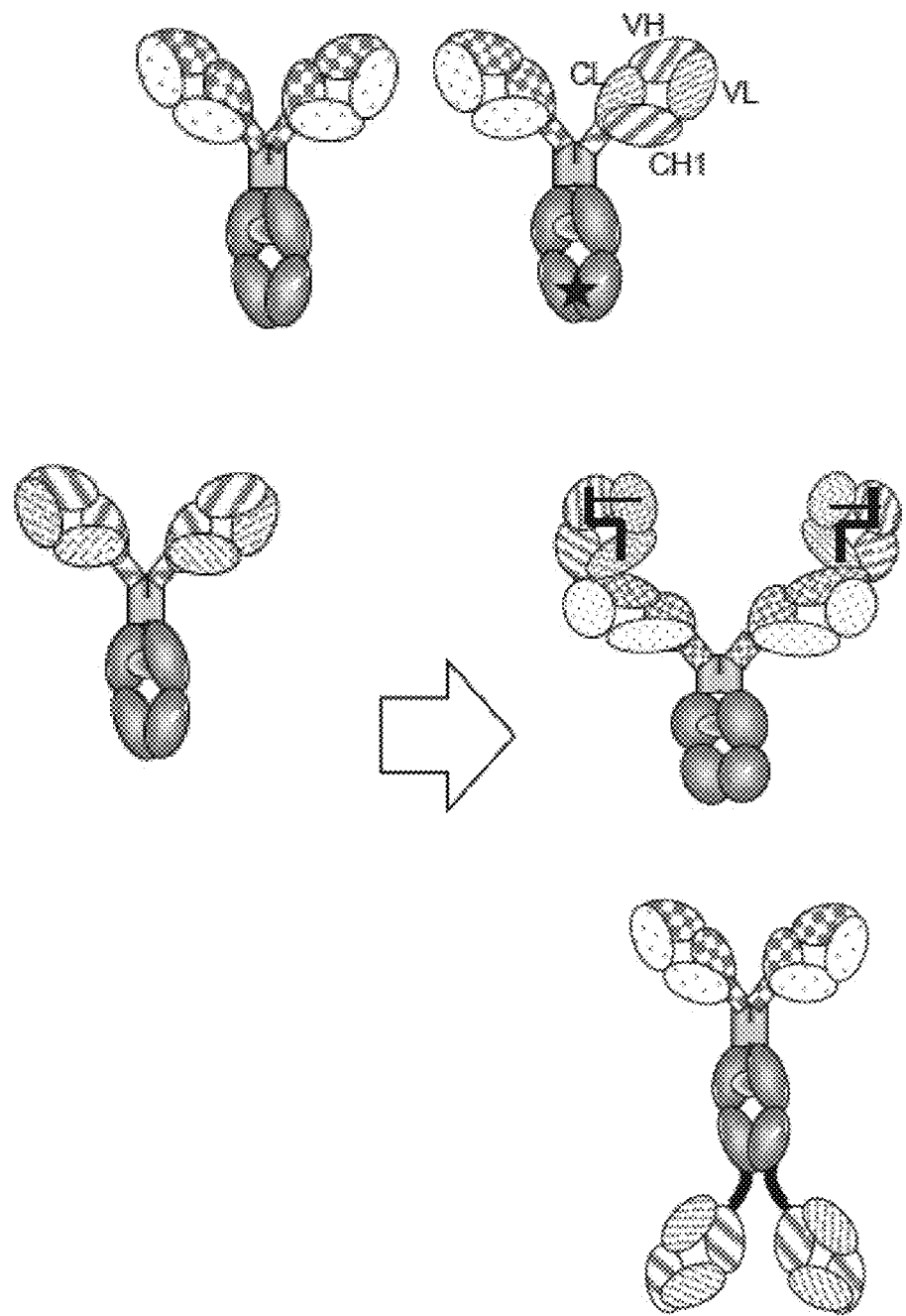

FIG. 4A Overview of generation of anti-TNFa:IL-17IL-17 bispecific antibodies with different stoichiometries and geometries. Schematic view of the prototypic bispecific antibodies: 1+1 CrossMab (top right) consisting of an anti-IL-17 crossed arm (Ch1-Cκ exchange) and an uncrossed anti-TNFa antibody arm. 2+2 scFab (middle right) is composed of two anti-IL-17 scFabs connected to the N-termini of the anti-TNFa antibody. The scFabs are further stabilized by introduction of an additional disulfide bond in the IL-17 variable regions. We used position 44 of the heavy chain and position 100 of the light chain, respectively, to introduce cysteine residues, which can form a disulfide bond when the variable regions of heavy and light chain associate. 2+2 CrossMab (bottom right) includes two crossed anti-IL-17 Fabs (Ch1-Cκ exchange) C-terminally connected to an anti-TNFa antibody. In this format, anti-IL-17 crossed heavy chains (VH+Ck) were fused via a Gly-Ser connector peptide $(G_4S)_4$ to both C-terminal ends of the heavy chains of the anti-TNFa mAb. The parental mAbs are shown on the left, with the anti-TNFa antibody at the top and the anti-IL-17 antibody at the bottom. TNFa-binding entities are marked in chequered (VH) and spotted (VL) shading, IL-17 binding entities in large striped (VH) and small striped (VL) shading. The glycosylation site within the Fc-part is indicated by dots and linker peptides are shown in as thick black lines. Extra disulfide bonds, outside of the hinge region, are marked as thin black bars. The "Knob-into hole" sequence variants are represented by a star.

FIG. 4B(1), FIG. 4B(2), FIG. 4B(3), FIG. 4B(4), FIG. 4B(5), FIG. 4B(6), FIG. 4B(7), FIG. 4B(8), FIG. 4B(9), FIG. 4B(10), FIG. 4B(11), and FIG. 4B(12)—Generation of anti-TNFa:IL-17 bispecific antibodies with different anti-IL-17 Fab amino acid sequences, stoichiometries and geometries.

TNFa-binding entities are marked in chequered (VH) and spotted (VL) shading, IL-17 binding entities in large striped (VH) and small striped (VL) shading. The glycosylation site within the Fc-part is indicated by dots and linker peptides are shown in as thick black lines. Extra disulfide bonds, outside of the hinge region, are marked as thin black bars. The "Knob-into hole" sequence variants are represented by a star.

FIG. 4B(1) illustrate the anti-TNFa parental antibody.

FIGS. 4B(2) and 4B(3) illustrate two anti-IL-17 parental antibodies #136 and #134 respectively.

FIGS. 4B(4), 4B(5), and 4B(6) illustrate 1+1 constructs:

FIG. 4B(4) illustrates antibody #10, IL17a(136)/X-TNFa.

FIG. 4B(5) illustrates antibody #12 scFab-TNFa/IL-17a (136).

FIG. 4B(6) illustrates antibody #22 TNFa/X-IL-17a(134).

FIGS. 4B(7), 4B(8), and 4B(9) illustrate 2+2 scFab constructs:

FIG. 4B(7) illustrates #13 scFab-IL-17a(136)/TNFa and #26 scFab-IL-17a(134)/TNFa.

FIG. 4B(8) illustrates #27 scFab-IL-17a(134)/TNFa.

FIG. 4B(9) illustrates #30 scFab-TNFa/IL-17a(134).

FIGS. 4B(10), 4B(11), and 4B(12) illustrate 2+2 Cross-Mab constructs:

4B(10) illustrates #14 IL-17a(136)/X-TNFa and #29 IL-17a(134)/X-TNFa.

4B(11) illustrates #16 TNFa/X-IL-17a(134).

4B(12) illustrates #28 TNFa/X-IL-17a(134).

Figure 4C:
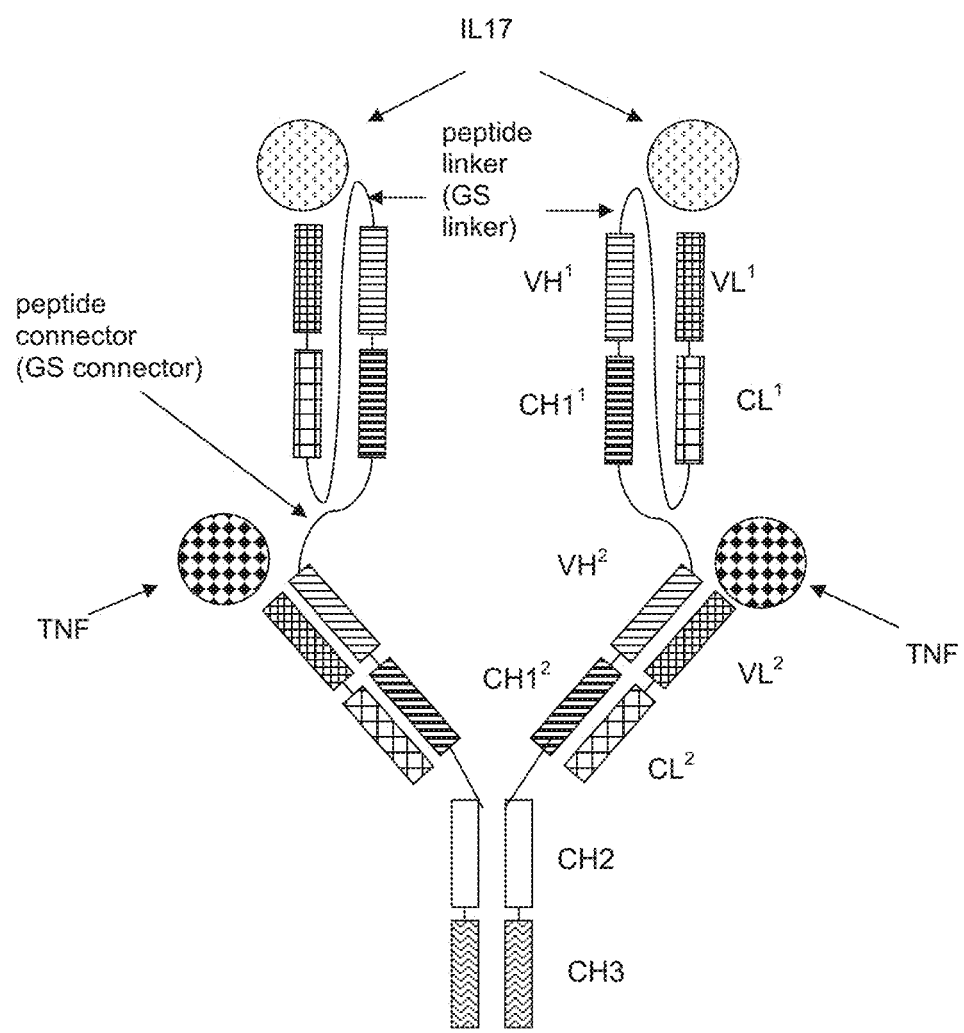

FIG. 4C Detailed schematic drawing of a bispecific tetravalent scFab-IL-17/TNFa antibody having the 2+2 scFab format.

The 2+2 scFab antibody shown comprises two anti-IL-17 scFabs connected to an anti-TNFa antibody via peptide connectors.

Figure 4D:
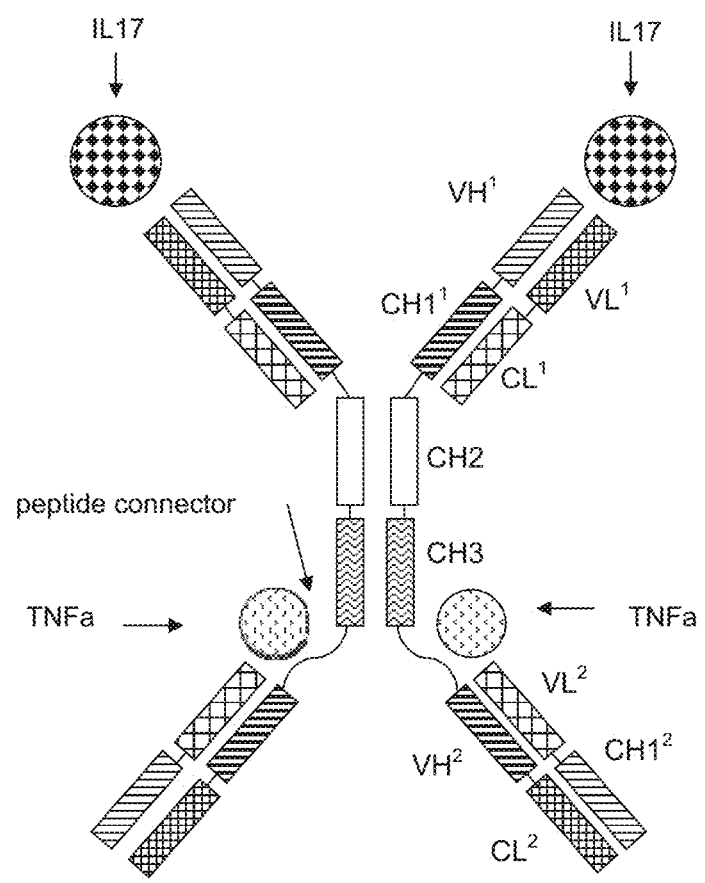

FIG. 4D Detailed schematic drawing of a bispecific tetravalent anti-IL-17/TNFa antibody having the 2+2 Cross-Mab format.

The 2+2 CrossMab antibody shown comprises two crossed anti-TNFa Fabs (CH1-CL exchange) connected to an anti-IL-17 antibody via peptide connectors.

Figure 5:
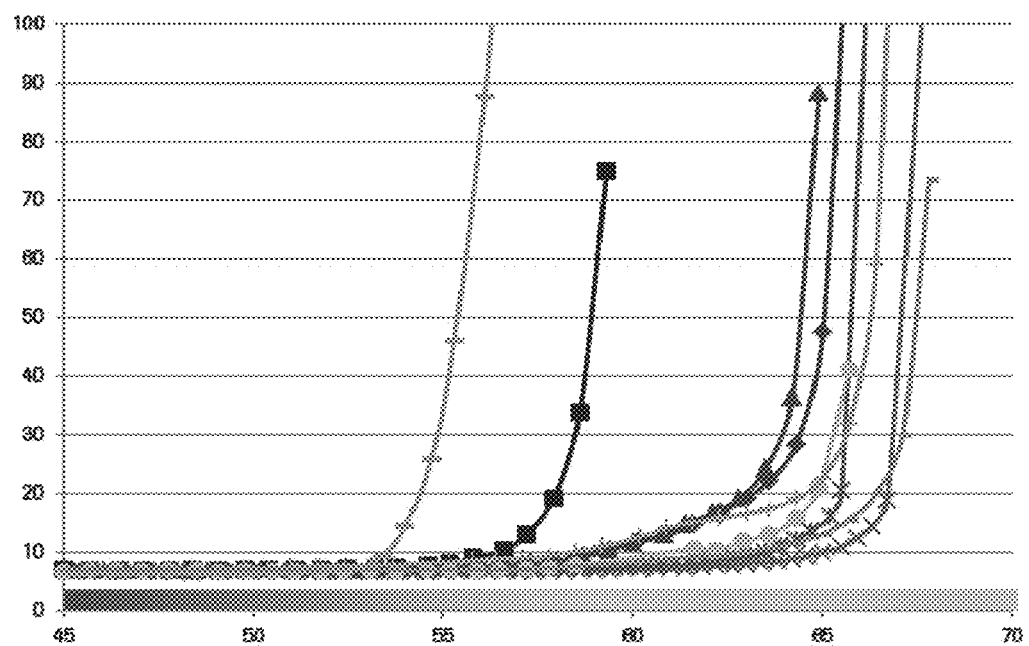

FIG. 5 Study of stability of tetravalent bispecific anti-IL-17/TNFa antibodies.

Antibody stability was measured as protein aggregation over a range of temperatures as shown. The line indicating stability of DVD_TNFa-IL-17 is the left-most line, the line indicating stability of antibody #30 is the right-most line. The line with diamonds is for antibody #13, with squares is for antibody #14, with triangles is for antibody #16, with crosses is for antibody #26, with asterisks is for antibody #27, with circles is for antibody #28, and with dashes is for antibody #29.

FIG. 6A, FIG. 6B, FIG. 6C, FIG. 6D, FIG. 6E, FIG. 6F, FIG. 6G, and FIG. 6H—Concomitant inhibition of in vitro combinational cytokine treatment in FLS by usage of bispecific antibody constructs. RA-FLS were challenged with TNFa, IL-17 or combination in vitro as already described before. In parallel, cells were cultured alone or in the presence of titrated amounts of parental antibodies specific for TNFa or IL-17 or bispecific antibodies (each at 150 nM). Exemplarily shown is the reduction of cytokine secretion (IL-6, IL-8, G-CSF and RANTES) after 24 hrs (exemplary for one RA-FLS donor (#2259) out of two tested at one antibody concentration (150 nM; upper bar diagrams).

Figure 6A:
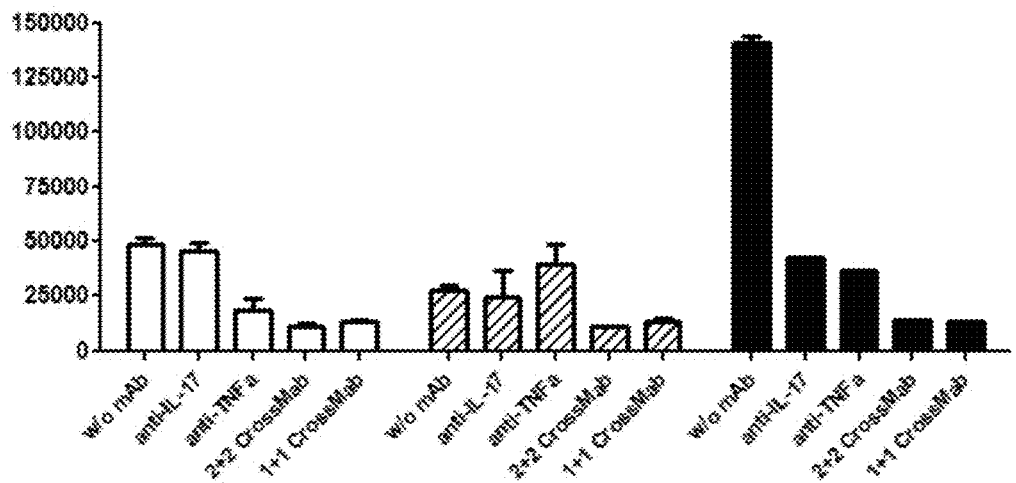

FIG. 6A shows reduction of IL-6 secretion.

Figure 6B:
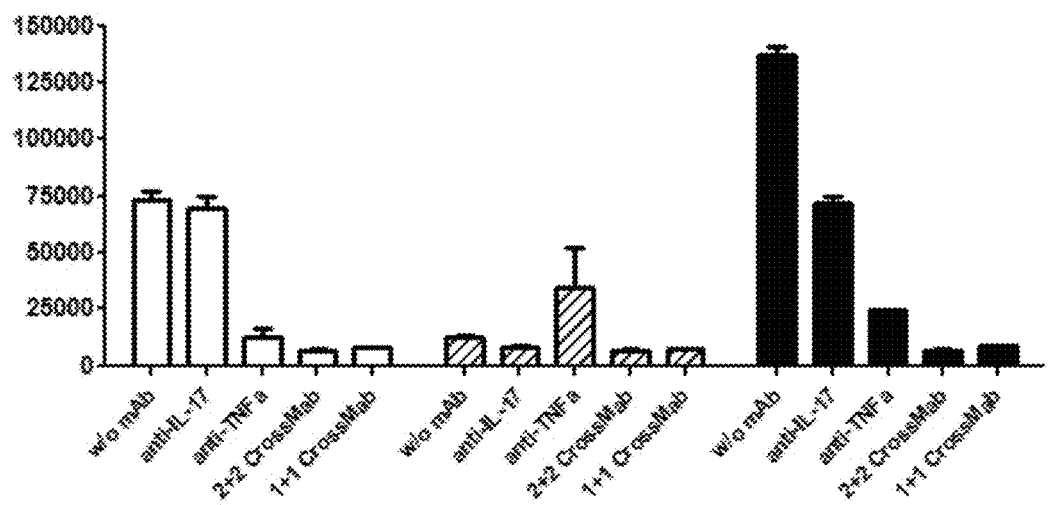

FIG. 6B shows reduction of IL-8 secretion.

Figure 6C:
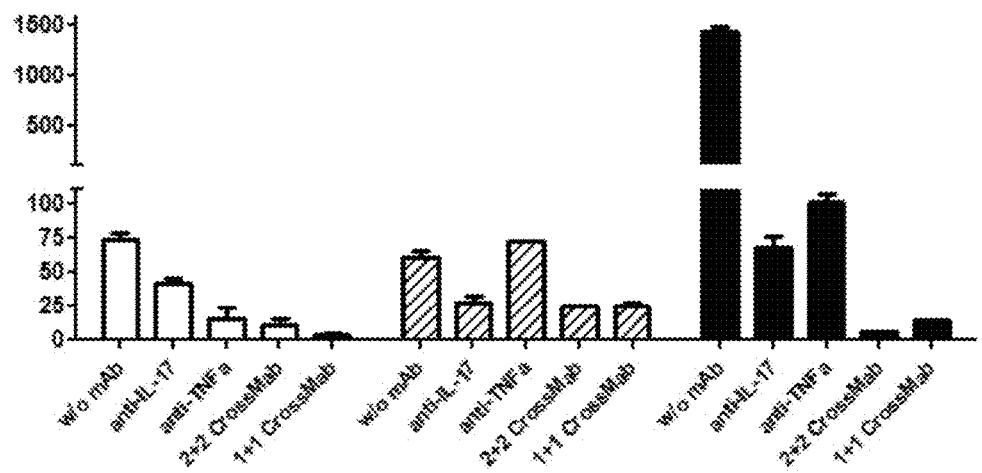

FIG. 6C shows reduction of G-CSF secretion.

Figure 6D:
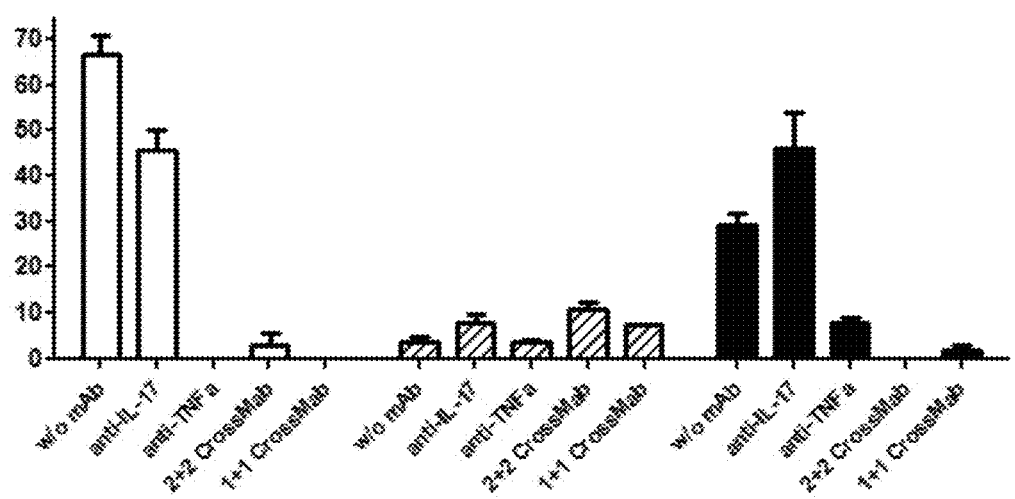

FIG. 6D shows reduction in RANTES secretion.

Figure 6E:
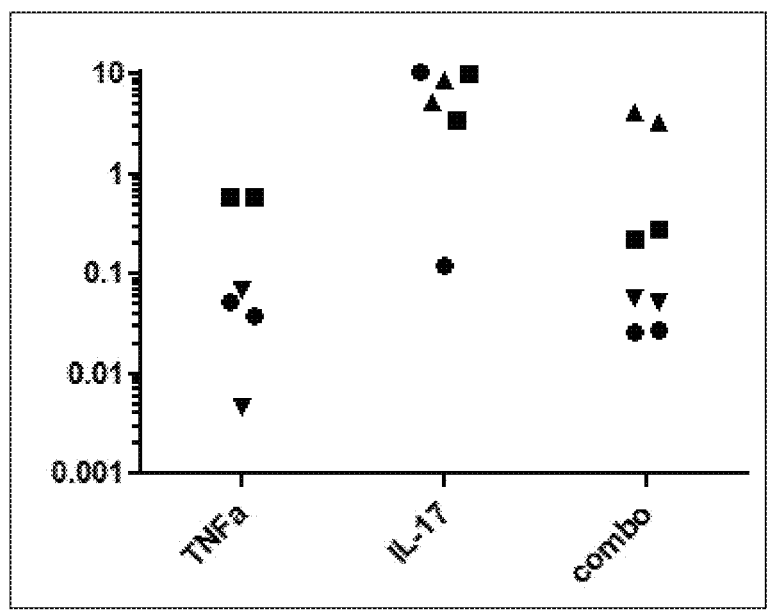

In addition, IC50 values [nM] for inhibition of cytokine production by different parental as well as bispecific antibodies as obtained from two RA-FLS donors are shown:

FIG. 6E shows IC50 values for IL-6 inhibition.

Figure 6F:
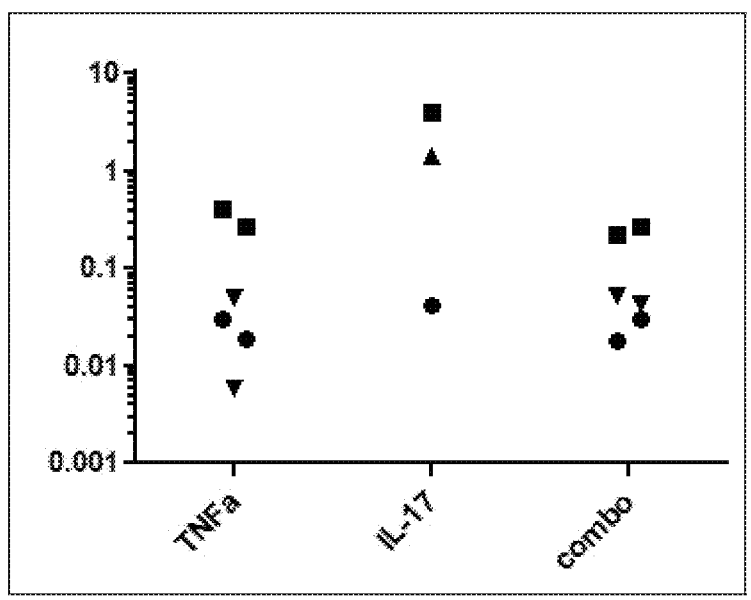

FIG. 6F shows IC50 values for IL-8 inhibition.

Figure 6G:
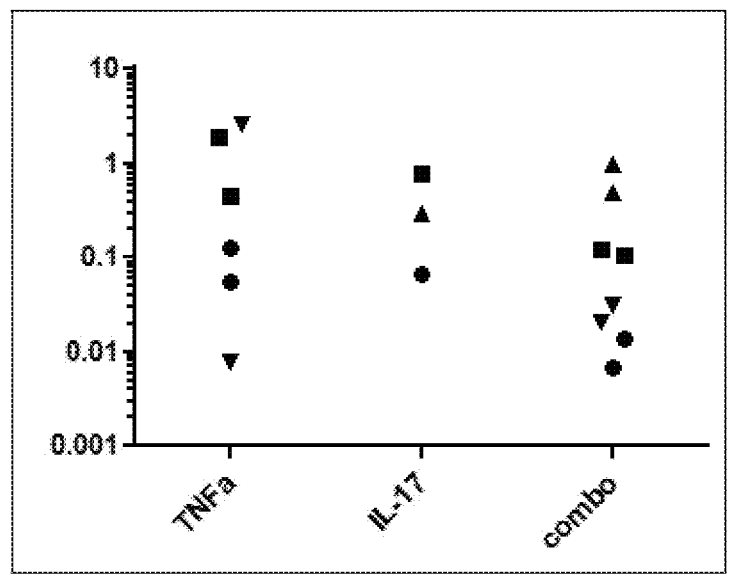

FIG. 6G shows IC50 values for G-CSF inhibition.

Figure 6H:
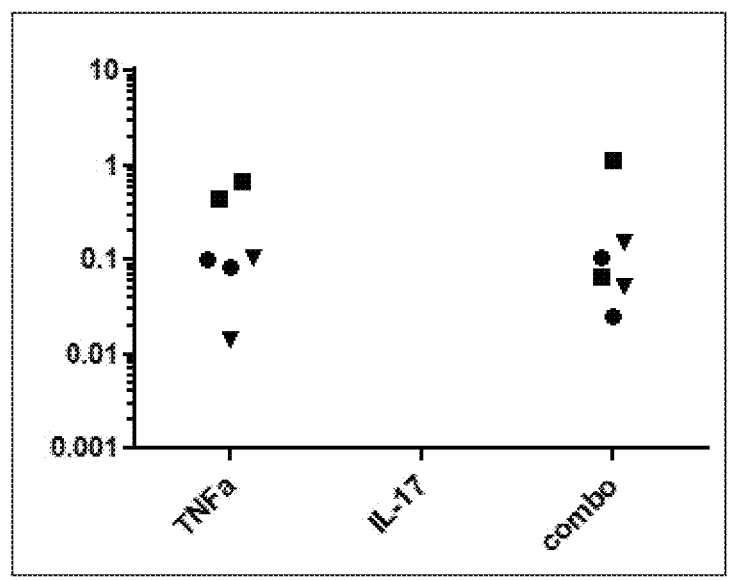

FIG. 6H shows IC50 values for RANTES inhibition.

The following sequences are disclosed in the sequence listing.

| Anti-IL-17 antibodies #134 and #136 | |
|---|---|
| SEQ ID NO: 1 | #134 and 136 VH CDR 1 amino acid sequence |
| SEQ ID NO: 2 | #134 and 136 VH CDR 2 amino acid sequence |
| SEQ ID NO: 3 | #134 and 136 VH CDR 3 amino acid sequence |
| SEQ ID NO: 4 | #134 and 136 VL CDR 1 amino acid sequence |
| SEQ ID NO: 5 | #134 and 136 VL CDR 2 amino acid sequence |
| SEQ ID NO: 6 | #134 and 136 VL CDR 3 amino acid sequence |
| SEQ ID NO: 7 | #134 VH domain nucleotide sequence |
| SEQ ID NO: 8 | #134 VH domain amino acid sequence |
| SEQ ID NO: 9 | #134 VL domain nucleotide sequence |
| SEQ ID NO: 10 | #134 VL domain amino acid sequence |
| SEQ ID NO: 11 | #136 VH domain nucleotide sequence |
| SEQ ID NO: 12 | #136 VH domain amino acid sequence |
| SEQ ID NO: 13 | #136 VL domain nucleotide sequence |
| SEQ ID NO: 14 | #136 VL domain amino acid sequence |
| SEQ ID NO: 15 | #134 VH FR1 amino acid sequence |
| SEQ ID NO: 16 | #134 VH FR2 amino acid sequence |
| SEQ ID NO: 17 | #134 VH FR3 amino acid sequence |
| SEQ ID NO: 18 | #134 VH FR4 amino acid sequence |
| SEQ ID NO: 19 | #134 VL FR1 amino acid sequence |
| SEQ ID NO: 20 | #134 VL FR2 amino acid sequence |
| SEQ ID NO: 21 | #134 VL FR3 amino acid sequence |
| SEQ ID NO: 22 | #134 VL FR4 amino acid sequence |
| SEQ ID NO: 23 | #136 VH FR1 amino acid sequence |
| SEQ ID NO: 24 | #136 VH FR2 amino acid sequence |
| SEQ ID NO: 25 | #136 VH FR3 amino acid sequence |
| SEQ ID NO: 26 | #136 VH FR4 amino acid sequence |
| SEQ ID NO: 27 | #136 VL FR1 amino acid sequence |
| SEQ ID NO: 28 | #136 VL FR2 amino acid sequence |
| SEQ ID NO: 29 | #136 VL FR3 amino acid sequence |
| SEQ ID NO: 30 | #136 VL FR4 amino acid sequence |
| Anti-TNFa (Adalimumab) | |
| SEQ ID NO: 31 | VH CDR 1 amino acid sequence |
| SEQ ID NO: 32 | VH CDR 2 amino acid sequence |
| SEQ ID NO: 33 | VH CDR 3 amino acid sequence |
| SEQ ID NO: 34 | VL CDR 1 amino acid sequence |
| SEQ ID NO: 35 | VL CDR 2 amino acid sequence |
| SEQ ID NO: 36 | VL CDR 3 amino acid sequence |
| SEQ ID NO: 37 | VH domain nucleotide sequence |
| SEQ ID NO: 38 | VH domain amino acid sequence |
| SEQ ID NO: 39 | VL domain nucleotide sequence |
| SEQ ID NO: 40 | VL domain amino acid sequence |
| Parental amino acid sequences | |
| SEQ ID NO: 41 | IL-17 #134 heavy chain |
| SEQ ID NO: 42 | IL-17 #134 light chain |
| SEQ ID NO: 43 | IL-17 #136 heavy chain |
| SEQ ID NO: 44 | IL-17 #136 light chain |
| SEQ ID NO: 45 | Adalimumab heavy chain |
| SEQ ID NO: 46 | Adalimumab light chain |
| 2 + 2 CrossMab sequences | |
| SEQ ID NO: 47 | #14 heavy chain |
| SEQ ID NO: 48 | #16 heavy chain |
| SEQ ID NO: 49 | #28 heavy chain |
| SEQ ID NO: 50 | #29 heavy chain |
| SEQ ID NO: 51 | #14 first soluble chain |
| SEQ ID NO: 52 | #29 first soluble chain |
| SEQ ID NO: 53 | #14 and #29 second soluble chain |
| SEQ ID NO: 54 | #16 and #28 first soluble chain |
| SEQ ID NO: 55 | #16 second soluble chain |
| SEQ ID NO: 56 | #28 second soluble chain |
| 2 + 2 scFab sequences | |
| SEQ ID NO: 57 | #13 heavy chain |
| SEQ ID NO: 58 | #26 heavy chain |
| SEQ ID NO: 59 | #27 heavy chain |
| SEQ ID NO: 60 | #30 heavy chain |
| SEQ ID NO: 61 | #13, #26 and #27 light chain |
| SEQ ID NO: 62 | #30 light chain |
| SEQ ID NO: 75 | #13 heavy chain variant |
| SEQ ID NO: 76 | #26 heavy chain variant |
| SEQ ID NO: 77 | #27 heavy chain variant |
| SEQ ID NO: 78 | #30 heavy chain variant |
| SEQ ID NO: 79 | #13 heavy chain variant |

-continued

| SEQ ID NO: 80 | #26 heavy chain variant |
| SEQ ID NO: 81 | #27 heavy chain variant |
| SEQ ID NO: 82 | #30 heavy chain variant |
| | 1 + 1 CrossMab sequences |
| SEQ ID NO: 63 | #10 and #12 heavy chain "holes" |
| SEQ ID NO: 64 | #10 and #12 heavy chain "knobs" |
| SEQ ID NO: 65 | #10 and #12 light chain |
| SEQ ID NO: 66 | #10 "light" chain ("crossed) |
| SEQ ID NO: 67 | #12 heavy chain scFab "knobs" |
| SEQ ID NO: 68 | #22 heavy chain "holes" |
| SEQ ID NO: 69 | #22 heavy chain "knobs" |
| SEQ ID NO: 70 | #22 light chain |
| SEQ ID NO: 71 | #22 "light" chain ("crossed") |
| SEQ ID NO: 72 | Human IL-17 |
| SEQ ID NO: 73 | Cynomolgus IL-17 |
| SEQ ID NO: 74 | Human TNFa amino acid sequence |

DETAILED DESCRIPTION OF THE INVENTION

The present invention relates to bispecific tetravalent antibodies against human IL-17 and TNFa, methods of producing such antibodies and therapeutic uses of such antibodies.

The antibodies of the invention are bispecific tetravalent antibodies against IL-17 and TNFa. The bispecific tetravalent antibodies of the invention have four antigen binding sites: two antigen binding sites for IL-17 and two antigen binding sites for TNFa. Antibodies having two antigen binding sites for IL-17 and two antigen binding sites for TNFa are referred herein as having a "2+2" format.

The antibodies of the invention may have a "2+2 scFab" format. In this format the antibodies have the form of two single chain Fabs (scFabs) are attached to the two N-terminal ends of an IgG, for example as shown in FIG. 4C. A 2+2 scFab antibody be referred to as "scFab-IL-17/TNFa", such an antibody takes the form of two anti-IL-17 scFabs attached to an anti-TNFa IgG. A 2+2 scFab antibody be referred to as "scFab-TNFa/IL-17", such an antibody takes the form of two anti-TNFa scFabs attached to an anti-IL-17 IgG.

Accordingly, the present invention provides a bispecific tetravalent antibody against IL-17 and TNFa, the antibody having two IL-17 binding sites and two TNFa binding sites, the antibody comprising two heavy chains and two light chains, wherein each heavy chain comprises, in the following order:
a first VL domain,
a CL domain,
a first VH domain,
a CH1 domain,
a second VH domain,
a CH1 domain,
a CH2 domain and
a CH3 domain;
wherein the two light chains each comprise a second VL domain and a CL domain,
wherein the first VL domain and a first VH domain of each respective heavy chain form a first antigen-binding site, thereby providing two first antigen-binding sites;
and wherein each light chain associates with a respective heavy chain to provide a second antigen binding site comprising a second VH domain and a second VL domain, thereby providing two second antigen-binding sites;

and wherein either (i) each first antigen-binding site is an IL-17 binding site and each second antigen-binding site is a TNFa binding site; or (ii) each first antigen-binding site is a TNFa binding site and each second antigen-binding site is an IL-17 binding site.

In the 2+2 scFab antibodies of the invention, chain mispairing is prevented because the N-terminal portions of the antibody form the structure of single chain Fabs which each comprise a first VH and a first VL domain (for example as shown in FIG. 4C). This means that the first VH and first VL domains of the scFab are held in proximity which facilitates their correct pairing with each other, and means that the first VL domain of the scFAb is prevented from mispairing with the second VH domain (that is the VH domain that is located in the part of the heavy chain that forms the structure of an IgG).

In a 2+2 scFab antibody of the invention, the peptide linker is a peptide which may comprise or consist of about 5 to about 40 amino acid residues, about 25 to about 35 amino acid residues, or about 30 amino acid residues. The peptide linker may comprise or consist of Glycine (G) and Serine (S) residues. The peptide linker may comprise or consist of G and S residues according the formula (GxS)y, wherein x is an integer between 1 and 5, i.e. x is 1, 2, 3, 4 or 5, and y is an integer between 1 and 10, i.e. y is 1, 2, 3, 4, 5, 6, 7, 8, 9 or 10. Preferably x is 4. Preferably y is 6. Preferably x is 4 and y is 6, such that the peptide linker is a $(G_4S)_6$ peptide, i.e. 30 amino acids. Also preferred is a peptide linker of $(G_4S)_6GG$, i.e. 32 amino acids. Other preferred linkers are longer, comprising the 30 $(G_4S)_6$ peptide or 32 amino acid $(G_4S)_6GG$ amino acids, provided the molecule is functional in the required antigen binding.

In a 2+2 scFab antibody of the invention, the CH1 domain that is fused to the first VH domain may be connected to the second VH domain via a peptide connector. Such a peptide connector is a peptide that may comprise or consist of about 5 to about 30 amino acid residues, or about 15 to about 25 amino acid residues, or about 20 amino acid residues. The peptide connector may comprise or consist of Glycine (G) and Serine (S) residues. The peptide connector may comprise or consist of G and S residues according the formula (GxS)y, wherein x is an integer between 1 and 5, i.e. x is 1, 2, 3, 4 or 5, and y is an integer between 1 and 7, i.e. y is 1, 2, 3, 4, 5, 6 or 7. Preferably x is 3. Preferably y is 3. Preferably x is 3 and y is 3, such that the peptide connector is a $(G_3S)_3$ peptide.

The present invention further provides a bispecific tetravalent antibody against IL-17 and TNFa, the antibody having two IL-17 binding sites and two TNFa binding sites, wherein the antibody has the following binding activity:
a) each binding site against IL-17 binds to the same epitope on IL-17 as an antigen-binding site comprising either
(i) the VH domain of SEQ ID NO:8 and the VL domain of SEQ ID NO:10; or
(ii) the VH domain of SEQ ID NO:12 and the VL domain of SEQ ID NO: 14; and
b) each binding site against TNFa binds to the same epitope on TNFa as an antigen-binding site comprising the VH of SEQ ID NO: 38 and the VL domain of SEQ ID NO: 40.

The antibodies of the invention having such binding activity may be 2+2 CrossMab antibodies or may be 2+2 scFab antibodies.

An antibody of the invention may be wherein:
a) each binding site against IL-17 comprises a VH domain comprising CDRH3 of SEQ ID NO:3; and b) each binding site against TNFa comprises a VH domain comprising CDRH3 of SEQ ID NO:33.

An antibody of the invention may be wherein:
a) each binding site against IL-17 comprises a VH domain comprising CDRH1 of SEQ ID NO:1, CDRH2 of SEQ ID NO:2, and CDRH3 of SEQ ID NO:3; and
b) each binding site against TNFa comprises a VH antibody domain comprising CDRH1 of SEQ ID NO:31, CDRH2 of SEQ ID NO:32, and CDRH3 of SEQ ID NO:33.

An antibody of the invention may be wherein:
a) each binding site against IL-17 comprises a VH domain and a VL domain, wherein the VH domain comprises CDRH1 of SEQ ID NO:1, CDRH2 of SEQ ID NO:2, and CDRH3 of SEQ ID NO:3, and wherein the VL domain comprises CDRL1 of SEQ ID NO:4, CDRL2 of SEQ ID NO:5, and CDRL3 of SEQ ID NO:6; and
b) each binding site against TNFa comprises a VH domain and a VL domain, wherein the VH domain comprises CDRH1 of SEQ ID NO:31, CDRH2 of SEQ ID NO:32, and CDRH3 of SEQ ID NO:33, and wherein the VL domain CDRL1 of SEQ ID NO:34, CDRL2 of SEQ ID NO:35, and CDRL3 of SEQ ID NO:36, CDRs of Adalimumab.

An antibody of the invention may be wherein:
a) each binding site against IL-17 comprises the VH domain of SEQ ID NO:8 (of #134) or SEQ ID NO:12 (of #136); and
b) each binding site against TNFa comprises the VH domain of SEQ ID NO: 38 (of Adalimumab).

An antibody of the invention may be wherein:
a) each binding site against IL-17 comprises the VL domain of SEQ ID NO:10 (of #134), or SEQ ID NO:14 (of #136); and
b) each binding site against IL-17 comprises the VL domain of SEQ ID NO:40 (of Adalimumab).

An antibody of the invention may be wherein:
(i) each binding site against IL-17 comprises the VH domain of SEQ ID NO:8 (of #134); or
(ii) each binding site against IL-17 comprises the VL domain of SEQ ID NO:10 (of #134).

An antibody of the invention may be wherein:
(i) each binding site against IL-17 comprises the VH domain of SEQ ID NO:8 (of #134); and
(ii) each binding site against IL-17 comprises the VL domain of SEQ ID NO:10 (of #134).

A preferred antibody of the invention may be wherein each heavy chain has the amino acid sequence of SEQ ID NO:48, each first soluble chain has the amino acid sequence of SEQ ID NO:54, and each second soluble chain has the amino acid sequence of SEQ ID NO:55. Such an antibody is a preferred 2+2 Cross Mab (#16).

An antibody of the invention may be wherein each heavy chain has the amino acid sequence of SEQ ID NO:47, each first soluble chain has the amino acid sequence of SEQ ID NO:51, and each second soluble chain has the amino acid sequence of SEQ ID NO:53 (#14).

An antibody of the invention may be wherein each heavy chain has the amino acid sequence of SEQ ID NO:49, each first soluble chain has the amino acid sequence of SEQ ID NO:54, and each second soluble chain has the amino acid sequence of SEQ ID NO:56 (#28).

An antibody of the invention may be wherein each heavy chain has the amino acid sequence of SEQ ID NO:50, each first soluble chain has the amino acid sequence of SEQ ID NO:52, and each second soluble chain has the amino acid sequence of SEQ ID NO:53 (#29).

An antibody of the invention may be wherein each heavy chain has the amino acid sequence of SEQ ID NO:57 or a cleaved variant thereof, and each light chain has the amino acid sequence of SEQ ID NO:61.

An antibody of the invention may be wherein each heavy chain has the amino acid sequence of SEQ ID NO:57, or a cleaved variant thereof lacking Lys 938 or lacking both Gly937 and Lys938, and each light chain has the amino acid sequence of SEQ ID NO:61.

A preferred antibody of the invention may be wherein each heavy chain has the amino acid sequence of SEQ ID NO:57, and each light chain has the amino acid sequence of SEQ ID NO:61. Such an antibody is a preferred 2+2 scFab (#13).

An antibody of the invention may be wherein each heavy chain comprises, has, or consists of the amino acid sequence of SEQ ID NO:75 and each light chain has the amino acid sequence of SEQ ID NO:61.

An antibody of the invention may be wherein each heavy chain comprises, has, or consists of the amino acid sequence of SEQ ID NO:79, and each light chain has the amino acid sequence of SEQ ID NO:61

An antibody of the invention may be wherein each heavy chain comprises, has, or consists of the amino acid sequence of SEQ ID NO:57, SEQ ID NO:75 or SEQ ID NO:79, and each light chain has the amino acid sequence of SEQ ID NO:61. SEQ ID NO:57 encodes the full-length heavy chain of antibody #13. SEQ ID NO:75 encodes the cleaved variant of the full-length heavy chain of antibody #13 which lacks the C-terminal lysine (Lys938) of the full-length sequence. SEQ ID NO:79 encodes the cleaved variant of the full-length heavy chain of antibody #13 which lacks the C-terminal glycine-lysine (Gly937 and Lys938) of the full-length sequence.

An antibody of the invention may be wherein each heavy chain has the amino acid sequence of SEQ ID NO:58 or a cleaved variant thereof, and each light chain has the amino acid sequence of SEQ ID NO:61.

An antibody of the invention may be wherein each heavy chain has the amino acid sequence of SEQ ID NO:58, or a cleaved variant thereof lacking Lys938 or lacking both Gly937 and Lys938, and each light chain has the amino acid sequence of SEQ ID NO:61.

An antibody of the invention may be wherein each heavy chain has the amino acid sequence of SEQ ID NO:58, and each light chain has the amino acid sequence of SEQ ID NO:61 (#26).

An antibody of the invention may be wherein each heavy chain comprises, has, or consists of the amino acid sequence of SEQ ID NO:76, and each light chain has the amino acid sequence of SEQ ID NO:61.

An antibody of the invention may be wherein each heavy chain comprises, has, or consists of the amino acid sequence of SEQ ID NO:80, and each light chain has the amino acid sequence of SEQ ID NO:61.

An antibody of the invention may be wherein each heavy chain comprises, has, or consists of the amino acid sequence of SEQ ID NO:58, SEQ ID NO:76 or SEQ ID NO:80, and each light chain has the amino acid sequence of SEQ ID NO:61. SEQ ID NO:58 encodes the full-length heavy chain of antibody #26. SEQ ID NO:76 encodes the cleaved variant of the full-length heavy chain of antibody #26 which lacks the C-terminal lysine (Lys938) of the full-length sequence. SEQ ID NO:80 encodes the cleaved variant of the full-length heavy chain of antibody #26 which lacks the C-terminal glycine-lysine (Gly937 and Lys938) of the full-length sequence.

An antibody of the invention may be wherein each heavy chain has the amino acid sequence of SEQ ID NO:59 or a cleaved variant thereof, and each light chain has the amino acid sequence of SEQ ID NO:61.

An antibody of the invention may be wherein each heavy chain has the amino acid sequence of SEQ ID NO:59, or a cleaved variant thereof lacking Lys938 or lacking both Gly937 and Lys938, and each light chain has the amino acid sequence of SEQ ID NO:61.

An antibody of the invention may be wherein each heavy chain has the amino acid sequence of SEQ ID NO:59, and each light chain has the amino acid sequence of SEQ ID NO:61 (#27).

An antibody of the invention may be wherein each heavy chain comprises, has, or consists of the amino acid sequence of SEQ ID NO:77, and each light chain has the amino acid sequence of SEQ ID NO:61.

An antibody of the invention may be wherein each heavy chain comprises, has, or consists of the amino acid sequence of SEQ ID NO: 81, and each light chain has the amino acid sequence of SEQ ID NO:61.

An antibody of the invention may be wherein each heavy chain comprises, has, or consists of the amino acid sequence of SEQ ID NO:59, SEQ ID NO:77 or SEQ ID NO:81, and each light chain has the amino acid sequence of SEQ ID NO:61. SEQ ID NO: 59 encodes the full-length heavy chain of antibody #27. SEQ ID NO: 77 encodes the cleaved variant of the full-length heavy chain of antibody #27 which lacks the C-terminal lysine (Lys938) of the full-length sequence. SEQ ID NO: 81 encodes the cleaved variant of the full-length heavy chain of antibody #27 which lacks the C-terminal glycine-lysine (Gly937 and Lys938) of the full-length sequence.

An antibody of the invention may be wherein each heavy chain has the amino acid sequence of SEQ ID NO:60 or a cleaved variant thereof, and each light chain has the amino acid sequence of SEQ ID NO:62.

An antibody of the invention may be wherein each heavy chain has the amino acid sequence of SEQ ID NO:60, or a cleaved variant thereof lacking Lys933 or lacking both Gly932 and Lys933, and each light chain has the amino acid sequence of SEQ ID NO:62.

An antibody of the invention may be wherein each heavy chain has the amino acid sequence of SEQ ID NO:60, and each light chain has the amino acid sequence of SEQ ID NO:62 (#30).

An antibody of the invention may be wherein each heavy chain comprises, has, or consists of the amino acid sequence of SEQ ID NO:78, and each light chain has the amino acid sequence of SEQ ID NO:62.

An antibody of the invention may be wherein each heavy chain comprises, has, or consists of the amino acid sequence of SEQ ID NO: 82, and each light chain has the amino acid sequence of SEQ ID NO:62.

An antibody of the invention may be wherein each heavy chain comprises, has, or consists of the amino acid sequence of SEQ ID NO:60, SEQ ID NO:78 or SEQ ID NO:82, and each light chain has the amino acid sequence of SEQ ID NO:62. SEQ ID NO:60 encodes the full-length heavy chain of antibody #30. SEQ ID NO:78 encodes the cleaved variant of the full-length heavy chain of antibody #30 which lacks the C-terminal lysine (Lys932) of the full-length sequence. SEQ ID NO:82 encodes the cleaved variant of the full-length heavy chain of antibody #30 which lacks the C-terminal glycine-lysine (Gly932 and Lys933) of the full-length sequence.

The antibodies of the invention may compete for binding to IL-17 and/or TNFa with an antibody disclosed herein. For example an antibody of the invention may compete for binding to IL-17 and/or TNFa with an antibody selected from antibody #13, #14, #16, #26, #27, #28, #29, and #30.

Preferably the antibodies of the invention are antibodies comprising the CDR and/or variable domain sequences of the anti-IL-17 antibody #134.

Preferably the antibodies of the invention are 2+2 Cross-Mab antibodies.

The antibodies of the invention preferably inhibit IL-17 and/or TNFa. Inhibition may also be termed neutralisation herein, and refers to the reduction of a biological activity of IL-17 or TNFa. The reduction in biological activity may be partial or total. The degree to which an antibody inhibits IL-17 or TNFa is referred to as its potency. Potency may be expressed as an IC50 value. In functional assays, IC50 is the concentration that reduces a biological response by 50% of its maximum. IC50 may be calculated by plotting % maximal biological response (represented e.g. by IL-6 production in response to IL-17) or % inhibition by antibody, and using a software program such as Prism (GraphPad) to fit a sigmoidal function to the data to generate an IC50 value. Algorithm 205 may be used in the software X1Fit.

The antibodies of the invention may be inhibitors of inflammatory cytokine production. In particular, they may be inhibitors of matrix metalloproteinase (MMP) production, which MMP production is induced by IL-17, by TNFa, or by a combination of IL-17 and TNFa. The antibodies of the invention may be inhibitors of the production of inflammatory cytokines such as IL-6, IL-8, G-CSF and RANTES by cells such as fibroblast-like synoviocytes (FLS) and chondrocytes, which inflammatory cytokine production is induced by IL-17, by TNFa, or by a combination of IL-17 and TNFa.

The antibodies of the invention may inhibit the production of IL-6 and/or IL8 by RA-FLS that is induced by stimulation with IL-17. The antibodies may inhibit IL-6 and/or IL-8 production in response to IL-17 in RA-FLS with an IC50 value of 1.0 nM or less, or with an IC50 value of 0.5 nM or less, or with an IC50 value of 0.4 nM or less.

The antibodies of the invention may inhibit the production of IL-6 and/or IL-8 by RA-FLS that is induced by stimulation with TNFa. The antibodies may inhibit IL-6 and/or IL-8 production in response to TNFa in RA-FLS with an IC50 value of 0.2 nM or less, or with an IC50 value of 0.15 nM or less, with an IC50 value of 0.1 nM or less, or with an IC50 value of 0.05 nM or less.

The antibodies of the invention may inhibit the production of MMP by chondrocytes that is induced by combined stimulation with IL-17 and TNFa (IL-17/TNFa combined stimulation). The antibodies may inhibit MMP production in response to IL-17/TNFa combined stimulation in chondrocytes with an IC50 value of $5 \times 10^{-8}$ M or less, with an IC50 value of $1 \times 10^{-8}$ M or less, $7 \times 10^{-9}$ M or less, or $3 \times 10^{-9}$ M or less.

The antibodies of the invention may bind IL-17 with an apparent $K_D$ of 1.0 nM or less, with an apparent $K_D$ of 0.5 nM or less, with an apparent $K_D$ of 0.2 nM or less, with an apparent $K_D$ of 0.1 nM or less, or with an apparent $K_D$ of 0.05 nM or less. Binding to IL-17 refers to binding to an IL-17A/A homodimer.

The antibodies of the invention may bind TNFa with an apparent $K_D$ of 1.0 nM or less, with an apparent $K_D$ of 0.5 nM or less, with an apparent $K_D$ of 0.1 nM or less, or with apparent $K_D$ of 0.05 nM or less, preferably with an apparent $K_D$ of 0.02 nM or less.

Binding affinity ($K_d$) may be determined using an "SPR-based kinetic affinity determination" as described under that heading below in the Materials and Methods section. Assessment of independent IL-17- and TNFa-binding to the CrossMab may be determined as also described below in the Materials and Method section.

The antibodies of the invention bind to IL-17, which is also known as IL-17A. The antibodies of the invention bind to IL-17A/A dimers and IL-17A monomers in IL-17 heterodimers with IL-17B, IL-17C, IL-17D, IL-17E or IL-17F. The antibodies of the invention preferably do not bind to non-IL-17A monomers, that is, they do not bind to IL-17B, IL-17C, IL-17D, IL-17E or IL-17F monomers.

The antibodies of the invention bind to IL-17A/A homodimers, and to heterodimers comprising an IL-17A monomer. The antibodies of the invention may bind IL-17A/A homodimers and bind heterodimers comprising an IL-17A monomer, and do not bind non-IL-17A homodimers. The antibodies of the invention preferably bind IL-17A/A homodimers and IL-17A/F heterodimers, and do not bind IL-17F/F homodimers.

The antibodies of the invention may cross-react with both human IL-17 and cynomolgus IL-17. A cross-reactive antibody binds both human IL-17 and cynomolgus IL-17. Specifically, the antibodies of the invention may bind human IL-17A, human IL-17A/A homodimers, and heterodimers comprising human IL-17A, and also bind cynomolgus IL-17A, cynomolgus IL-17A/A homodimers, and heterodimers comprising cynomolgus IL-17A. Thus, the antibodies of the invention may be used in cynomolgus models to investigate their mechanism of action in vivo.

An antibody of the invention may compete for binding to IL-17 and/or TNFa with any antibody of the invention disclosed herein e.g. antibody #13, #14, #16, #26, #27, #28, #29, or #30.

Competition between antibodies may be assayed in vitro, for example by tagging a reporter molecule to one binding member which can be detected in the presence of one or more other untagged binding members, to enable identification of binding members which bind the same epitope or an overlapping epitope.

Competition may be determined for example using ELISA in which e.g. IL-17, fragment of IL-17, is immobilised to a plate and a first tagged antibody is added to the plate along with one or more other untagged antibody is added to the plate. Presence of an untagged antibody that competes with the tagged binding member is observed by a decrease in the signal emitted by the tagged binding member. Similarly, a surface plasmon resonance assay may be used to determine competition between binding members.

The antibodies of the invention may have high stability. Stability may be determined by measuring antibody aggregation under conditions of increasing temperature. Antibodies that do not have high stability will tend to aggregate at a relatively low temperature, whereas antibodies that have high stability will aggregate only at a relatively high temperature (see FIG. 4E).

The antibodies of the invention may have high stability such that at 55° C. a 1 mg/ml formulation in 20 mM His/HisCl, 140 mM NaCl solution at pH 6.0 does not exhibit significant aggregation. Preferred antibodies of the invention have an aggregation onset temperature of >55° C., preferably >58° C., in a 1 mg/ml formulation in 20 mM His/HisCl, 140 mM NaCl solution at pH 6.0. This may be determined using a DLS (dynamic light scattering) method in which samples are heated up and the hydrodynamic radius ("radius, nm") is recorded continuously during heat-up. The temperature of onset of aggregation (Tagg) is a metric for stability. See further the Materials and Methods below.

The antibodies of the invention may have additional disulphide bonds. Such additional disulphide bonds may improve the stability of the antibody.

The antibodies of the invention may comprise one, two, or more than two additional disulphide bonds, especially outside of the hinge region.

Additional disulphide bond may be employed as a consequence of the introduction of the knob-into-hole mutations, between the two heavy chains at position S354C on the knob side, and Y349C on the hole side.

Another option is the further stabilization of antibodies such as scFabs, with exchange of the amino acid at position 44 of the heavy chain and at position 100 of the light chain, respectively, for a cysteine.

Disulphide bonds may be between a light chain variable domain and a heavy chain variable domain, or between a light chain constant domain and a heavy chain CH1 constant domain.

The antibody heavy chain variable domain (VH) and the antibody light chain variable domain (VL) of the heavy and light chain can be disulphide stabilized by introduction of a disulphide bond between the following positions:
  i) heavy chain variable domain position 44 to light chain variable domain position 100,
  ii) heavy chain variable domain position 105 to light chain variable domain position 43, or
  iii) heavy chain variable domain position 101 to light chain variable domain position 100 (numbering always according to the Kabat numbering (of variable domains) (Kabat, E. A., et al., (1991) Sequences of Proteins of Immunological Interest, Fifth Ed., NIH Publication No 91-3242).

The antibody heavy chain variable domain (VH) and the antibody light chain variable domain (VL) of the heavy and light chain of the antibody that specifically binds to a second antigen) may be disulphide stabilized by introduction of a disulphide bond between the following positions: heavy chain variable domain position 44 to light chain variable domain position 100.

Such further disulphide stabilization may be achieved by the introduction of a disulphide bond between the variable domains VH and VL of the antibody heavy and light chain.

Techniques to introduce unnatural disulphide bridges for stabilization for a single chain Fv are described e.g. in WO 94/029350, Rajagopal, V., et al, Prot. Engin. 10 (1997) 1453-59; Kobayashi, H., et al., Nuclear Medicine & Biology, Vol. 25, (1998) 387-393; or Schmidt, M., et al., Oncogene (1999) 18, 1711-1721.

An optional disulphide bond between the variable domains may be between heavy chain variable domain position 44 and light chain variable domain position 100, and this may be preferred.

An optional disulphide bond between the variable domains may be between heavy chain variable domain position 105 and light chain variable domain position 43 (numbering always according to the Kabat numbering (of variable domains)).

Antibodies having one or more such disulphide bonds outside of the hinge region may have improved stability (high stability). Stability may be determined by measuring antibody aggregation under conditions of increasing temperature.

Pharmaceutical compositions and formulations according to the present invention, and for use in accordance with the present invention, may comprise an antibody of the invention and a pharmaceutically acceptable excipient, carrier, buffer, stabiliser or other materials well known to those skilled in the art. Such materials such be non-toxic and should not interfere with the efficacy of the antibody. The composition may be in the form of a lyophilised formulation or an aqueous solution. The precise nature of the carrier or other material will depend on the route of administration, which may be by injection. Administration of the composition may be subcutaneous, for example subcutaneous injection. Thus the composition of the invention may be a composition for subcutaneous administration.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The composition should be sterile for in vivo administration. This may be readily accomplished by filtration through sterile filtration membranes, prior to or following lyophilization and reconstitution. The target binding member ordinarily will be stored in lyophilized form or in solution.

For injection the composition will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Many methods for the preparation of pharmaceutical formulations are known to those skilled in the art. See e.g. Robinson, 1978, and Osol, 1980.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

A composition may be administered alone or in combination with other treatments, concurrently or sequentially or as a combined preparation with another therapeutic agent or agents, and this may be dependent upon the condition to be treated.

The antibodies of the invention are useful for treating or preventing rheumatoid arthritis. The antibodies of the invention may be particularly useful in treating or preventing rheumatoid arthritis in patients exhibiting elevated TNFa and/or IL-17 or in patients who have been determined to have elevated TNFa and/or IL-17, and/or in patients who are non-responsive to anti-TNFa treatment.

Accordingly, the invention provides methods of treatment comprising administration an antibody of the invention, pharmaceutical compositions or formulations comprising such an antibody, and use of such an antibody in the manufacture of a medicament for administration, or example in a method of making a medicament or pharmaceutical composition comprising formulating the antibody with a pharmaceutically acceptable excipient.

The invention provides a method of treating or preventing rheumatoid arthritis, the method comprising administering to a subject in need of treatment an antibody of the invention or composition thereof.

The invention provides antibodies as described herein for use in a method of treatment.

The invention also provides antibodies as described herein for use in a method of treating or preventing rheumatoid arthritis in a patient. The patient may have or exhibit elevated TNFa and/or IL-17. The patient may have been determined to have elevated TNFa and/or IL-17.

The invention further provides antibodies as described herein for use in a method or treating a patient to prevent or reduce bone erosion, cartilage damage, or synovitis, or to improve grip strength or bond formation rate.

An antibody for use in the present invention may be used as part of a combination therapy in conjunction with an additional medicinal component. Combination treatments may be used to provide significant synergistic effects, particularly the combination of a binding member for use in the present invention with one or more other drugs. An antibody for use in the present invention may be administered concurrently or sequentially or as a combined preparation with another therapeutic agent or agents, for the treatment of one or more of the conditions listed herein.

For example, an antibody for use in the invention may be used in combination with an existing therapeutic agent for the treatment of rheumatoid arthritis.

The invention also provides methods for the production of an antibody according to the invention. In such methods the sequences of nucleic acids encoding the chains of an antibody according to the invention are inserted into one or more expression vectors, said vector(s) is/are inserted in a eukaryotic host cell, the encoded antibody is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, HEK293F cells, COS cells, yeast, or *E. coli* cells, and the antibody is recovered from the cells (from the supernatant or after cells lysis).

Recombinant production of antibodies is well-known in the state of the art and described, for example, in the review articles of Makrides, 1999; Geisse, 1996; Kaufman 2000; and Werner, 1998.

The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including column chromatography and others well known in the art. See Ausubel, F. et al. (eds.), Current Protocols in Molecular Biology, Greene Publishing and Wiley Interscience, New York (1987).

Antibodies are suitably separated from the culture medium by conventional immunoglobulin purification procedures such as, for example, protein A-Sepharose, hydroxylapatite chromatography, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, HEK293F cells, CHO cells, or myeloma cells that do not otherwise produce immunoglobulin protein, to obtain the synthesis of recombinant monoclonal antibodies in the host cells.

Antibodies produced by host cells may undergo post-translational cleavage of one or more, particularly one or two, amino acids from the C-terminus of the heavy chain. This may be the case for the 2+2 scFab antibodies of the invention. Therefore an antibody produced by a host cell by expression of a specific nucleic acid molecule encoding a full-length heavy chain may include the full-length heavy chain, or it may include a cleaved variant of the full-length heavy chain (also referred to herein as a cleaved variant heavy chain). This may be the case where the final two C-terminal amino acids of the heavy chain are glycine and lysine. The cleaved variant may lack the final C-terminal amino acid or the final two C-terminal amino acids of the full-length heavy chain. The cleaved variant may lack the final C-terminal amino acid which is a lysine or the final two C-terminal amino acids which are glycine and lysine of the full-length heavy chain. Hence the host cell may produce a population of antibodies wherein the population comprises antibodies including a full-length heavy chain and antibodies including a cleaved variant heavy chain.

The final C-terminal amino acids of an antibody heavy chain, particularly the final two C-terminal amino acids of an antibody heavy chain, such as the final two amino acids of SEQ ID NOs 75-82, are part of the constant domain (or constant region). More specifically, the final C-terminal amino acids of an antibody heavy chain, such as the final two amino acids of SEQ ID NOs 75-82, are in the end part of the CH3 domain. This end part of the CH3 domain is not involved in the binding of an antigen and is not involved in effector functions. Thus the antibodies of the invention comprising full-length heavy chains have the same binding function and effector functions as antibodies of the invention comprising cleaved variant heavy chains.

Compositions of the invention, such as the pharmaceutical compositions described herein, comprise a population of antibodies of the invention. The population of antibodies may comprise antibodies having a full-length heavy chain and antibodies having a cleaved variant heavy chain. The population of antibodies may consist of a mixture of antibodies having a full-length heavy chain and antibodies having a cleaved variant heavy chain, wherein at least 50%, at least 60%, at least 70%, at least 80% or at least 90% of the antibodies have a cleaved variant heavy chain.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an antibody.

Antibodies comprising a cleaved variant heavy chain may be obtained by providing a nucleic acid encoding a heavy chain sequence that lacks one or more C-terminal amino acids relative to a full-length heavy chain. Antibodies comprising a cleaved variant heavy chain may be obtained by providing a nucleic acid encoding a heavy chain sequence that lacks one or two C-terminal amino acids relative to a full-length heavy chain. Antibodies comprising a cleaved variant heavy chain may be obtained by providing a nucleic acid encoding a cleaved variant heavy chain sequence according to any one of SEQ ID NOs 75-82. The nucleic acid may be transfected into a host cell, such as one of the host cells described above, to obtain recombinant antibodies comprising heavy chain cleaved variants from the host cells.

A population of antibodies comprising antibodies having a full-length heavy chain and antibodies having a cleaved variant heavy chain may be obtained by providing a population of nucleic acids comprising nucleic acids encoding full-length heavy chains and nucleic acids encoding cleaved variant heavy chains. The population of nucleic acid may be transfected into a population of host cells, such that the population of host cells produces a population of antibodies comprising antibodies having a full-length heavy chain and antibodies having a cleaved variant heavy chain.

Nucleic acids encoding heavy chains of antibodies of the invention may be obtained by taking a heavy chain sequence and adding one or more amino acids to the C-terminus. Nucleic acids encoding heavy chains of antibodies of the invention may be obtained by taking a heavy chain sequence as set out in any one of SEQ ID NOs 75-78 and adding one amino acid to the C-terminus, which one amino acid may be lysine. Nucleic acids encoding heavy chains of antibodies of the invention may be obtained by taking a heavy chain sequence as set out in any one of SEQ ID NOs 79-82 and adding one or two amino acids to the C-terminus, which one or two amino acids may be glycine or glycine and lysine respectively.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

Terminology

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Rheumatoid arthritis (RA) is an inflammatory disorder that causes pain and swelling in the joints. RA is characterised by autoimmunity, synovial inflammation (synovitis), cartilage damage and bone destruction.

"Synovitis" refers to inflammation of the synovial membrane. The synovial membrane lines certain types of joints (synovial joints). Synovitis is commonly found in rheumatoid arthritis. Synovial joints include those in the wrists, fingers and knees, and all of these joints are commonly affected in RA. Synovitis also occurs in Psoriasis, Lupus (SLE) and other inflammatory diseases.

The term patient refers to a subject or individual. Preferably the subject is a human subject. The subject may have rheumatoid arthritis. The subject may have been determined to be predisposed to developing rheumatoid arthritis. The subject may have been determined to have elevated levels of IL-17 and/or TNFa.

"TNF" is tumour necrosis factor. TNF may also be termed TNFa, TNFa and TNF-alpha. TNF was formerly known as cachetin. TNFa as used herein means human TNF. The amino acid sequence of human TNF, as disclosed in Swiss Prot P01375, is set out in SEQ ID NO: 31.

"IL-17" is interleukin-17, which is also known as interleukin-17A. IL-17 as used herein means human IL-17 unless otherwise indicated. The amino acid sequence of human IL-17, as disclosed in Swiss Prot Q16552, is set out in SEQ ID NO: 32). Reference to "IL-17" or "IL-17" herein means IL-17A.

There are several members of the IL-17 family, in addition to IL-17 (IL-17A) there are IL-17B, IL-17C, IL-17D, IL-17E (also known as IL25) and IL-17F. IL-17A and IL-17F share a relatively high degree of sequence homology (about 50% amino acid sequence identity). IL-17A occurs as a homodimer ("IL-17A/A") and may also occur as a heterodimer with IL-17F ("IL-17A/F").

An antibody is an immunoglobulin, whether natural or partly or wholly synthetically produced. The term covers any binding protein that comprises an antigen-binding site provided by VH and VL domains.

An IgG antibody is an antibody having two heavy chains and associated two light chains. An IgG antibody has the archetypal "Y-shape" comprising two arms. The N-terminal ends of the light and heavy chains comprising the VH and VL domains form an antigen-binding site at the end of each arm.

The term "antigen-binding site", which may also be referred herein to as a "binding site", describes the part of an antibody molecule which comprises the area which specifically binds to and is complementary to part or all of an antigen. Where an antigen is large, an antibody may only bind to a particular part of the antigen, which part is termed an epitope. An epitope is a region of an antigen that is bound by an antibody. An antibody may be specific for a particular epitope that is unique to an antigen or common to related antigens.

The antigen-binding site of an antibody comprises amino acid residues from the "complementary determining regions" or "CDRs". CDR3 of the heavy chain is the region which contributes most to antigen binding and defines the antibody's properties. "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4.

An antigen-binding site is provided an antibody light chain variable domain (VL) and an antibody heavy chain variable region domain (VH).

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention.

The term "CDRH1" denotes the CDR1 region of the heavy chain variable region calculated according to Kabat (Kabat et al., Sequences of Proteins of Immunological Interest, 5th ed., Public Health Service, National Institutes of Health, Bethesda, Md. (1991)). CDRH2, CDRL3, etc. mean the respective regions from the heavy(H) or light(L) chain. For example, an antigen binding site characterized by comprising CDRH1 of SEQ ID NO:3 means that the antigen binding site comprises this amino acid sequence as a heavy chain variable chain CDR1 region in its variable heavy chain. For example, an antigen binding site characterized by comprising CDRH1 of SEQ ID NO:3, CDRH2 of SEQ ID NO:4, CDRH3 of SEQ ID NO:5 means that the antigen binding sites comprises in its heavy chain as sequence of CDR1 SEQ ID NO:3, as sequence of CDR2 SEQ ID NO:4, and as sequence of CDR3 SEQ ID NO:5.

One or more CDRs or a set of CDRs of an antibody may be grafted into a framework (e.g. human framework) to provide an antibody of the invention. Framework regions may comprise human germline gene segment sequences. Thus, the framework may be germlined, whereby one or more residues within the framework are changed to match the residues at the equivalent position in the most similar human germline framework. A non-germlined antibody has the same CDRs, but different frameworks, compared with a germlined antibody. In an antibody molecule of the invention it is preferred that all framework regions are human: any or all these may be human germline gene segment sequences and any or all of them may be germlined.

The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a non-human (e.g. mouse, rabbit or hamster) CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising for example a mouse variable region and a human constant region. Such mouse/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Variants of the VH and VL domains and CDRs for which amino acid sequences are set out herein can be obtained by means or methods of sequence alteration or mutation and screening, and can be employed in the antibodies of the invention. Heavy chain variants, such as the heavy chain cleaved variants described herein, can be obtained by sequence alteration of a nucleic acid encoding the heavy chain, such that the nucleic acid encodes a heavy chain lacking the final, or final two, C-terminal amino acids of the full-length heavy chain.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or inhibit IL-17 and/or TNFa and/or for any other desired property.

Variable domain amino acid sequence variants of any of the VH and VL domains whose sequences are specifically disclosed herein may be employed in the antibodies of the invention. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs.

Preferably alterations do not result in loss of function, so a binding member comprising a thus-altered amino acid sequence preferably retains an ability to bind and/or inhibit IL-17 and/or TNFa. More preferably, it retains the same quantitative binding and/or inhibiting ability as an antibody in which the alteration is not made, e.g. as measured in an in vitro or in vivo assay described herein. Most preferably, the binding member comprising a thus-altered amino acid sequence has an improved ability to bind or inhibit IL-17 or TNFa compared with a binding member in which the alteration is not made, e.g. as measured in an in vitro or in vivo assay described herein.

Alteration may comprise replacing one or more amino acid residues with a non-naturally occurring or non-standard amino acid, modifying one or more amino acid residue into a non-naturally occurring or non-standard form, or inserting one or more non-naturally occurring or non-standard amino acid into the sequence. Preferred numbers and locations of alterations of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc.

A light chain constant domain may be referred to herein as CL. Light chains domains may be of the kappa (Cκ) or lambda (Cλ) type, and light chain constant domains may be referred to herein as Cκ or Cλ.

Heavy chain constant regions may of any one or more immunoglobulin classes. Immunoglobulin classes include IgG, IgM, IgA, IgD and IgE isotypes, and in the case of IgG and IgA their subtypes. IgG constant domains may be used in preferred embodiments of the present invention, especially IgG1 (e.g. if Fc receptor binding is desired for effector function) or IgG4 (e.g. if reduced Fc receptor binding is desired).

The binding of an antibody to an antigen is reference to specific binding of that antibody to that antigen. An antibody that binds to an antigen specifically binds to that antigen. Specific binding refers to the interaction between antigen-binding site in an antibody and its cognate epitope in an antigen. The term is also applicable where e.g. an antigen-binding site is specific for a particular epitope which is carried by a number of antigens, in which case the antibody comprising the antigen binding-site will be able to bind to the various antigens carrying that epitope.

An antibody "against" a particular antigen is an antibody that binds to that antigen.

As used herein, the terms, "binds to", "binding", "specifically binding" refers to the binding of the bispecific antibody to an epitope of the antigen (either TNFa or IL-17) with sufficient affinity such that the antibody is useful as a therapeutic agent in inhibiting TNFa and/or IL-17 according to the invention. The binding of the antibody to an epitope of either antigen (either TNFa or IL-17) can be measured in an in vitro assay, preferably in an plasmon resonance assay (e.g. BIAcore, GE-Healthcare Uppsala, Sweden) with purified wild-type human antigen (preferably with IL-17A homodimer for the IL-17 antigen). The affinity of the binding is defined by the terms ka (rate constant for the association of the antibody from the antibody/antigen complex), kd (dissociation constant), and KD (kd/ka). A bispecific antibody comprising an antigen-binding site that specifically binds to IL-17 and an antigen-binding site that specifically binds to TNFa refers to a bispecific antibody with an IL-17 antigen-binding site which specifically binds to IL-17 with a binding affinity ($K_D$) of 1.0 nM or less (i.e. from $1.0 \times 10^{-9}$ M or less), e.g. from $1.0 \times 10^{-9}$ M to $1.0 \times 10^{-13}$ M (in one embodiment from $1.0 \times 10^{-9}$ M to $1.0 \times 10^{-13}$ M), and with a TNFa antigen-binding site which specifically binds to IL-17 with a binding affinity ($K_D$) of 1.0 nM or less (i.e. from $1.0 \times 10^{-9}$ M or less), e.g. from $1.0 \times 10^{-9}$ M to $1.0 \times 10^{-13}$ M (in one embodiment from $1.0 \times 10^{-9}$ M to $1.0 \times 10^{-13}$ M)

Binding affinity ($K_D$) may be determined according to a measurement protocol as set out above in the Materials and Methods.

The "affinity" of an antibody describes the strength of binding of s single antigen to single antigen-binding site, and is independent of the number of sites. When, however, a polyvalent antigen combines with a polyvalent antibody, the binding strength is greatly increased because all of the antibody-antibody bonds must be broken simultaneously before the antigen and antibody can dissociate. The total binding strength of a polyvalent antibody with a polyvalent antigen is referred to as the "avidity" of the interaction.

Antibodies which compete for binding to the same antigen can be identified by Surface Plasmon Resonance competition assay.

Antibody specificity refers to selective recognition of the antibody for a particular epitope of an antigen. Natural antibodies, for example, are monospecific.

"Bispecific antibodies" according to the invention are antibodies which have two different antigen-binding specificities. Where an antibody has more than one specificity, the recognized epitopes may be associated with a single antigen or with more than one antigen. Antibodies of the present invention are specific for two different antigens, IL-17 and TNFa.

The term "valent" as used herein denotes the presence of a specified number of binding sites in an antibody molecule. As such, the term "tetravalent" denotes the presence of four binding sites in an antibody molecule.

The bispecific antibodies according to the invention are "tetravalent", meaning that they have four binding sites. Some binding sites may be identical, so long as the antibody has binding sites for two different antigens (i.e. is bispecific).

The term "host cell" as used in the current application denotes any kind of cellular system which can be engineered to generate the antibodies according to the current invention. In one embodiment HEK293 cells and CHO cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Expression in NS0 cells is described by, e.g., Barnes, L. M., et al., Cytotechnology 32 (2000) 109-123; Barnes, L. M., et al., Biotech. Bioeng. 73 (2001) 261-270.

Transient expression is described by, e.g., Durocher, Y., et al., Nucl. Acids. Res. (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

EXAMPLES

Materials and Methods

General information regarding the nucleotide sequences of human immunoglobulins light and heavy chains is given in: Kabat, E. A., et al., *Sequences of Proteins of Immunological Interest,* 5th ed., Public Health Service, National Institutes of Health, Bethesda, Md. (1991). Amino acids of antibody constant chains are numbered and referred to according to EU index according to Kabat (Kabat, E. A., et al., *Sequences of Proteins of Immunological Interest,* 5th ed., Public Health Service, National Institutes of Health, Bethesda, Md., (1991)).

Recombinant DNA Techniques

Standard methods were used to manipulate DNA as described in Sambrook, J., et al., *Molecular Cloning: A Laboratory Manual*; Cold Spring Harbor Laboratory Press, Cold Spring Harbor, N.Y. (1989). The molecular biological reagents were used according to the manufacturer's instructions.

Gene Synthesis

Desired gene segments can be prepared from oligonucleotides made by chemical synthesis. The gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing.

Gene synthesis fragments were ordered according to given specifications at Geneart (Regensburg, Germany). All gene segments encoding light and heavy chains of TNFa/IL-17 bispecific antibodies were synthesized with a 5'-end DNA sequence coding for a leader peptide which targets proteins for secretion in eukaryotic cells, and unique restriction sites at the 5' and 3' ends of the synthesized gene. DNA sequences carrying disulfide stabilized "knobs-into-hole" modified heavy chains were designed with S354C and T366W mutations in the "knobs" heavy chain and Y349C, T366S, L368A and Y407V mutations in the "hole" heavy chain.

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 11.5 was used for sequence creation, mapping, analysis, annotation and illustration.

Expression Vectors

For the expression of the described antibodies variants of expression plasmids for transient expression (e.g. in HEK293 EBNA or HEK293-F cells) or for stable expression (e.g. in CHO cells) based either on a cDNA organization with a CMV-Intron A promoter or on a genomic organization with a CMV promoter were applied.

In case of IgG4_SPLE the intron between the CH1 domain and the hinge domain was removed, keeping the remainder of the antibody gene in a genomic organization. The intron-deleted version of IgG4_SPLE no longer shows hingeless antibodies as a result of a splice artefact commonly seen in IgG4_SPLE encoded in total genomic organization.

Beside the antibody expression cassette the vectors contained:
- an origin of replication which allows replication of this plasmid in *E. coli*, and
- a ß-lactamase gene which confers ampicillin resistance in *E. coli*.

The transcription unit of the antibody gene is composed of the following elements:
- unique restriction site(s) at the 5' end
- the immediate early enhancer and promoter from the human cytomegalovirus,
- followed by the Intron A sequence in the case of the cDNA organization,
- a 5'-untranslated region of a human antibody gene,
- an immunoglobulin heavy chain signal sequence,
- the human antibody chain (heavy chain, modified heavy chain or light chain) either as cDNA or as genomic organization with an the immunoglobulin exon-intron organization
- a 3' untranslated region with a polyadenylation signal sequence, and
- unique restriction site(s) at the 3'end. For transient and stable transfections larger quantities of the plasmids were prepared by plasmid preparation from transformed *E. coli* cultures (Nucleobond AX, Macherey-Nagel).

Cell Culture Techniques

Standard cell culture techniques were used as described in *Current Protocols in Cell Biology* (2000), Bonifacino, J. S., Dasso, M., Harford, J. B., Lippincott-Schwartz, J. and Yamada, K. M. (eds.), John Wiley & Sons, Inc.

Transient Transfections in HEK293-F System

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2 \times 10^6$ viable cells/ml on the day of transfection. DNA-293fectin™ complexes were prepared in Opti-MEM® I medium (Invitrogen, USA) using 325 µl of 293fectin™ (Invitrogen, Germany) and 250 µg of heavy and light chain plasmid DNA in a 1:1 molar ratio for a 250 ml final transfection volume for monospecific parent antibodies. "Knobs-into-hole" DNA-293fectin complexes with two heavy chains and one light chain were prepared in Opti-MEM® I medium (Invitrogen, USA) using 325 µl of 293fectin™ (Invitrogen, Germany) and 250 µg of "Knobs-into-hole" heavy chain 1 and 2 and light chain plasmid DNA generally in a 1:1:1 molar ratio for a 250 ml final transfection volume (For format described in WO2011/117330 ("bispecific one-armed scFab antibodies")). For expression yield and product quality optimization the ratio can be varied. DNA-293fectin complexes were prepared in Opti-MEM® I medium (Invitrogen, USA) using 325 µl of 293fectin™ (Invitrogen, Germany) and 250 µg of "Knobs-into-hole" heavy chain 1 and 2 and light chain 1 and 2 plasmid DNA in a 1:1:1:1 molar ratio for a 250 ml final transfection volume (For the format described in WO 2009/080253 ("CrossMabs" or "CH1-CL domain exchanged antibodies")). For expression yield and product quality optimization the ratio can be varied. Antibody containing cell culture supernatants were harvested 7 days after transfection by centrifugation at 14000 g for 30 minutes and filtered through a sterile filter (0.22 µm). Supernatants were stored at −20° C. until purification.

Protein Determination

The protein concentration of purified antibodies and derivatives was determined by determining the optical density (OD) at 280 nm, using the molar extinction coefficient calculated on the basis of the amino acid sequence according to Pace, C. N., et. al., Protein Science 4 (1995) 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads are washed three times in TBS-NP40 (50 mM Tris, pH 7.5, 150 mM NaCl, 1% Nonidet-P40). Subsequently, 1-15 mL cell culture supernatant are applied to the Protein A Agarose beads pre-equilibrated in TBS-NP40. After incubation for at 1 h at room temperature the beads are washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5,0. Bound antibody is eluted by addition of 35 µl NuPAGE® LDS Sample Buffer (Invitrogen). Half of the sample is combined with NuPAGE® Sample Reducing Agent or left unreduced, respectively, and heated for 10 min at 70° C. Consequently, 20 µl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was measured by Protein A-HPLC chromatography. Briefly, cell culture supernatants containing antibodies and derivatives that bind to Protein A were applied to a HiTrap Protein A column (GE Healthcare) in 50 mM K2HPO4, 300 mM NaCl, pH 7.3 and eluted from the matrix with 550 mM acetic acid, pH 2.5 on a Dionex HPLC-System. The eluted protein was quantified by UV absorbance and integration of peak areas. A purified standard IgG1 antibody served as a standard. Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 µL/well biotinylated anti-human IgG capture molecule F(ab')2<hFcgamma>BI (Dianova) at 0.1 µg/mL for 1 h at room temperature or alternatively over night at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 h on a microtiterplate shaker at room temperature. The wells were washed three times with 200 µL/well PBST and bound antibody was detected with 100 µl F(ab')2<hFcgamma>POD (Dianova) at 0.1 µg/mL as detection antibody for 1-2 h on a microtiterplate shaker at room temperature. Unbound detection antibody was washed away three times with 200 μL/well PBST and the bound detection antibody was detected by addition of 100 μL ABTS/well. Determination of absorbance was performed on a Tecan Fluor Spectrometer at a measurement wavelength of 405 nm (reference wavelength 492 nm).

Purification of Bispecific Antibodies

Bispecific antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Fractions containing purified bispecific antibodies with less than 5% high molecular weight aggregates were pooled and stored as 1.0 mg/ml aliquots at −80° C.

SDS-PAGE

The NuPAGE® Pre-Cast gel system (Invitrogen) was used according to the manufacturer's instruction. In particular, 4-20% NuPAGE® Novex® TRIS-Glycine Pre-Cast gels and a Novex® TRIS-Glycine SDS running buffer were used. Reducing of samples was achieved by adding NuPAGE® sample reducing agent prior to running the gel.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH2PO4$/$K2HPO4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

The total deglycosylated mass of the bispecific antibodies was determined and confirmed via electrospray ionization mass spectrometry (ESI-MS). Moreover potential sideproducts such as LC and HC mispairing were detected and relatively quantified. Briefly, 100 μg purified antibodies at a protein concentration of up to 3 mg/ml were deglycosylated with 14 or 28 U N-Glycosidase F (Roche) in 100 mM NaH2PO4/Na2HPO4, pH 7 at 37 or 45° C. for 16 or 2 h and subsequently desalted via HPLC on a Sephadex G25 column (GE Healthcare). The mass of the respective heavy and light chains was determined by ESI-MS after deglycosylation and reduction. In brief, 50 μg antibody in 115 μl were incubated at 37° C. for 30 min with 60 μl 0.5 M TCEP in 4 M Guanidine-hydrochloride and 50 μl 8 M Guanidine-hydrochloride and subsequently desalted. The total mass and the mass of the reduced heavy and light chains were determined via ESI-MS on a maXis UHR-TOF (Bruker) MS system equipped with a TriVersa NanoMate (Advion) source.

In Vitro Studies

Cells, Cell Culture Procedures and Reagents

Human primary fibroblast-like synoviocytes (FLS), derived from normal donors or RA patients, were obtained from Cell Applications, Inc. (San Diego, Calif.; German distributor: tebu-bio, Offenbach, Germany) at early passage (p.2-3) and cultured in *Synoviocyte Growth Medium* (Cell Applications, Inc.; Cat. #415-500) or in DMEM supplemented with 10% heat inactivated Fetal Calf Serum (FCS) (Invitrogen Life Technologies, Carlsbad, Calif.), 2 mM L-glutamine, Penicillin/streptomycin, 20 mM HEPES. Cells were normally used between passages four and eight. In brief, usually $2 \times 10^4$ HFLS-RA cells/well were seeded in 200 μl/well medium in 96-well cell culture plates (Costar/Corning Life Sciences, Amsterdam, The Netherlands) and pre-cultured for two days at 37° C., 5% $CO_2$ before cytokines (and optionally antibodies) were added. Prior to the cytokine addition, medium was removed and 150 μl/w of the corresponding cytokine (optional: antibody) dilution was added.

Primary human chondrocytes were obtained from a commercial source (Cell Applications, Inc., San Diego, Calif.) or from human cartilage obtained at autopsy through the National Disease Research Interchange (NDRI), Pennsylvania, USA. Cells were cultured in phenol-red free DMEM containing 10% heat-inactivated FCS, penicillin/streptomycin (Invitrogen Life Technologies, Carlsbad, Calif.), 25 μg/ml ascorbic acid (Sigma), HEPES (Invitrogen), and 2 mM L-glutamine. Upon confluence, chondrocytes were passaged 1:3, trypsinized, washed, and plated at $10^4$ cells per well in 96-well Primaria (Falcon) tissue culture plates in 200 μl growth medium for upcoming experiments. Chondrocytes were normally used between passages four and eight.

For some experiments, A-375 melanoma cells (obtained from ATCC, Manassas, Va.; #CRL-1619) were used according to the provider's instructions. Briefly, $2 \times 10^4$ cells/w were seeded in 200 μl/well in 96-well cell culture plates (Costar 3596), cultured overnight at 37° C., 5% $CO_2$ before medium was removed and stimuli and antibodies of interest were added and cells were incubated for additional 24 hrs.

Reagents and Antibodies Used in this Study

Human recombinant IL-17A protein (PeproTech, Hamburg, Germany; Cat. #200-17), IL-17AF (R&D Systems, Wiesbaden, Germany; Cat. #5194IL/CF), and TNFa (R&D Systems; Cat. #210-TA/CF TNFa) were used at indicated concentrations. The anti-human TNFa antibody, having Adalimumab VL/VH sequences, was constructed as human $IgG_1$. A Fab anti-TNFa was generated thereof by Papain cleavage using routine methods. The anti-human IL-17 antibodies #134 and #136 were generated in house as human $IgG_1$ Bispecific anti-TNFa:IL-17 antibodies were generated based on these antibodies and with a human $IgG_1$ backbone. A more detailed description of the generated antibody formats is mentioned in the result section. All antibodies and bispecific antibodies were generated by transient transfection of HEK293F cells using the Freestyle system (Invitrogen).

Commercially available Adalimumab/Humira® and Certolizumab were used for internal controls.

The anti-human TNFa antibody, based on Adalimumab VL/VH sequences, was constructed as human $IgG_1$. A Fab anti-TNFa was generated thereof by Papain cleavage using routine methods.

The anti-human IL-17 antibody (human $IgG_1$) was generated by standard methods upon repeated immunization of female Balb/c mice with recombinant human IL17 (Peprotech).

Bispecific anti-TNFa:IL-17 antibodies were generated based on these antibodies (human IgG$_1$ backbone). All antibodies and bispecific antibodies were generated by transient transfection of HEK293F cells using the Freestyle system (Invitrogen), using methods described elsewhere herein.

Commercially available Adalimumab/Humira® and Certolizumab® were used for internal controls.

Flow Cytometric Analysis

For detection of TNFRI (CD120a) and IL-17R/CD217 expression in synovial fibroblasts, untreated cultured FLS were subjected to FACS analysis immediately after accutase treatment. These FLS were stained with Alexa647-coupled anti-human CD217 (BioLegend, #340903) and biotinylated anti-human TNFRI antibody (BD Biosciences, #550900; followed by secondary antibody reagent), respectively, or appropriate isotype control antibodies.

To examine ICAM-1 expression and up-regulation, FLS were cultured in the presence or absence of indicated stimuli for 24 hrs. Cells were detached and collected, and were then incubated with PE-labelled anti-human ICAM-1 mAb (BD, #555511). After washing with PBS, stained cells (live-gated on the basis of forward and side scatter profiles and propidium iodide exclusion) were analyzed on a FACS Canto II (Becton-Dickinson, San Jose, Calif., USA) and data were processed using FlowJo software (TriStar).

Detection of Cytokines, Chemokines and MMPs and Antibody Inhibition Experiments

After a pre-culture of two days for synoviocytes, medium was removed and replaced with fresh growth medium containing indicated cytokines or antibodies. Cells were stimulated with recombinant IL-17 or TNFa or the combination of both for 24-72 hours, at which time supernatant was removed from the cell layer and stored at –80° C. prior to analysis. Cytokine content was measured using specific flex-sets (BD Biosciences) or ELISA kits (PharMingen) according to the manufacturer's instruction. In this study, the inhibitory potential of either mono- or bispecific antibodies was assessed or the combination of two monospecific (parental) antibodies.

Normal or RA-derived chondrocytes were plated in 96-well tissue culture dishes (10$^4$ cells/well) and allowed to attach overnight. Medium was replaced with fresh medium containing indicated antibody amounts and one hour later, given stimulant was added. Cells were then further incubated for 24 hours before media were collected and frozen in aliquots. MMP or cytokine expression was determined by AlphaLISA, Luminex, or using Aushon Searchlight kits. Some readouts (in particular MMP levels) were assessed using a standard alphaLISA kit according to the recommended protocol. All measurements were conducted using a PHERAstarPLUS luminescence microplate reader (BMG Labtech Inc., Cary, N.C., USA).

Knockdown of Gene Expression Using siRNA

Pre-designed short interfering RNA (siRNA) for TNFRSF1A and IL-17RA (Qiagen) were used to alter expression in RA-FLS. For siRNA transfections, Lipofectamine RNAi Max (Invitrogen)/siRNA mixtures were prepared in Optimem (Invitrogen) such that final concentrations were 2.5 µl/ml and 20 nM respectively. All siRNA solutions targeting a single gene were mixed with All Stars Negative control (Qiagen). RA-FLS were added to the complexes in basal media containing 1% (v/v) FBS for 48 hours prior to lysis for Taqman analysis or stimulated as follows. TNFA/IL-17A mixtures were made up and added to the transfected cultures such that final concentrations were 10 ng/ml and 100 ng/ml respectively. After a further 24 hours supernatant was harvested and cytokine levels were analyzed.

Taqman® Analysis

Total RNA was extracted using the RNeasy plus Mini kit and then transcribed to cDNA using AffinityScript QPCR cDNA Synthesis Kit. qPCR reactions were performed on an Mx3000P™ Real-Time PCR System (Agilent Technologies Inc., Santa Clara, Calif., USA). The resulting amplification and melt curves were analyzed to ensure specific PCR product. Threshold cycle (CT) values were used to calculate the fold change in transcript levels.

Stability Study

To assess the thermal stability of the various constructs, purified protein samples were transferred to 20 mM His/HisCl, 140 mM NaCl, pH 6.0. In 384-well plates, 40 µL of sample were covered with 20 µL of paraffin oil and heated from 25 to 80° C. with a constant heat rate of 0.05° C./min in a DLS (dynamic light scattering) PlateReader (Wyatt). The hydrodynamic radius (Rh) is recorded during this temperature ramp. The aggregation onset temperature (Tagg) is defined as the temperature at which the hydrodynamic radius sharply increases. By comparison with typical stable monoclonal antibodies, an aggregation onset temperature of >58° C. is desired for stable molecules.

SPR-Based Kinetic Affinity Determination

Around 2000 resonance units (RU) of the capturing system (10 µg/ml goat anti human IgG; GE Healthcare, Sweden) were immobilized on a CM4 or CM5 chip at pH 5.0 by amine coupling. The sample and system buffer was PBS-T (10 mM phosphate buffered saline with 0.05% Tween20 pH 7.4). The flow cell was set to 37° C. The bispecific antibody was captured by injecting a 25 nM solution for 120 sec at a flow of 10 µl/min. Association was measured by injection of human IL17 or TNFa in various concentrations in solution for 90 sec at a flow of 30 µl/min starting with 100 nM (IL17) or 25 nM (TNFa) in 1:2 dilutions. The dissociation phase was monitored for up to 600 sec, followed by surface regeneration by 40 sec washing with a 0.85% H$_3$PO$_4$ solution at a flow rate of 30 µl/min. Bulk refractive index differences as well as blank injections were considered (=double referencing). For calculation of apparent KD and other kinetic parameters the Langmuir 1:1 model was applied.

Assessment of Independent IL17- and TNF-Binding to the Crossmab

Around 3000 resonance units (RU) of the capturing system (10 µg/ml goat anti human IgG; GE Healthcare Bio-Sciences AB, Sweden) were immobilized on a CM4 chip at pH 5.0 by amine coupling. The sample and system buffer was PBS-T. The temperature of the flow cell was set to 25° C. The bispecific antibody was captured by injecting a 50 nM solution for 240 sec at a flow of 10 µl/min. Independent binding of each ligand to the bispecific antibody was analyzed by determining the active binding capacity for each ligand at 50 nM concentration for 120 sec, either added sequentially in both orders, or added as a mixture (flow of 30 µl/min). The surface was regenerated by 40 sec washing with a 0.85% H$_3$PO$_4$ solution at a flow rate of 30 µl/min. Bulk refractive index differences were corrected by subtracting the response obtained from a goat anti human IgG surface.

Example 1—Response of Synovial Fibroblasts to TNFa Stimulation and to IL-17 Stimulation Prior to functional in vitro studies the expression of the TNFa as well as IL-17 receptors (CD217) was assessed by FACS analysis. Human fibroblast-like synoviocytes (FLS), both from RA patients and healthy donors clearly expressed TNFRI and IL-17A receptor (FIG. 1A) without any major differences. Next, FLS were investigated for cytokine responses upon treatment with the respective ligands.

As is shown in FIGS. 1B(1), FIG. 1B(2), FIG. 1B(3), and FIG. 1B(4), stimulation of RA-FLS with titrated amounts of TNFa and also with IL-17 resulted in significant and high production of pro-inflammatory cytokines and chemokines such as Interleukin-6 and -8 or G-CSF. Interestingly, RANTES (CCL5) was mainly produced upon TNFa incubation but not in response to IL-17. Nevertheless, significantly lower amounts of TNFa than IL-17 were required to induce comparable cytokine responses. Similar results were obtained using FLS derived from healthy donors or using A375 melanoma cells. These effects were almost abolished in the presence of inhibiting/neutralizing monoclonal antibodies against TNFa (Adalimumab) or IL-17 (in-house generated mAb) underlining the specificity of the induced cytokine responses in vitro (FIGS. 1C(1) and FIG. 1C(2).

In addition, further biological effects such as proliferation and expression of adhesion makers were evaluated: both IL-17 and TNFa had no significant effect on FLS proliferation, whereas only TNFa leads to significant upregulation of ICAM-1 expression on both normal and RA-FLS (FIG. 1D).

Example 2—Response of Synovial Fibroblasts and Chondrocytes to Costimulation with IL-17 and TNFa The data from the experiments in Example 1 underline that IL-17 alone and TNFa alone play an important role in the activation of FLS. Recently, several studies demonstrated a synergistic interplay between certain cytokines, such as TNFa and IL-1ß etc. (Qi J et al.; Zhang Y et al.). Importantly, both IL-17 and TNFa are found at elevated levels in the synovium of RA patients (Ziolkowska M et al., J I 2000; Kotake S et al., J Clin Invest 1999; Saxne T et al., Arthritis Rheum 1988; Brennan F M et al., Lancet 1989; Husby G et al., J Autoimmun 1988) and they were shown to interact in vivo (Koenders M I et al., Arthritis Rheum 2011). We investigated whether co-treatment of IL-17 and TNFa led to an increased cytokine response in human RA-relevant cells such as FLS or chondrocytes.

RA-FLS from different donors were incubated with IL-17, TNFa, or IL-17 and TNFa in combination, and the production of several cytokines was assessed after 72 hours. Combinational treatment led to an additively increased production of IL-6 and IL-8, whereas G-CSF secretion was enhanced in a synergistic manner (FIG. 2A(1), FIG. 2A(2), FIG. 2A(3), and FIG. 2A(4)). In contrast, RANTES production was mainly induced by TNFa and not by IL-17 and there was no further induction by a combinational stimulation. The use of different cell donors also demonstrated some heterogeneity of the responses, but the same tendency was observed in cells from all donors tested.

The response of human chondrocytes upon single and combination stimulation with IL-17 and TNFa was investigated. For this, human primary chondrocytes, either derived from normal donors or RA patients, were incubated with TNFa, increasing concentrations of IL-17, or a combination of TNFa and IL-17 and subsequently checked for secretion of different MMPs and cytokines. Comparable to the FLS experiments, in RA and healthy human chondrocytes the TNFa/IL-17 combination treatment showed a clearly augmented response compared to the single stimulation, in particular for MMP-1, -3, and IL-8, mostly in a dose-dependent way. In addition, similar synergistic effects were also demonstrated for MCP-1 production and further pro-inflammatory cytokines and MMPs, whereas there were other markers not shown that responded only to a minor degree. Interestingly, there were some differences detectable between the responses of normal or RA chondrocytes, which were not observed between normal and RA FLS.

Altogether these data show that the combination of IL-17 and TNFa resulted in an increased production of pro-inflammatory cytokines and matrix-degenerative enzymes in vitro.

Example 3—In Vitro Response to TNFa/L-17 in Combination is Reduced by Knockdown of TNFa and IL-17 Receptors The results of Example 2 were further supported by additional siRNA data. For this experiment, FLS were transfected with TNFRI or IL-17RA. The abundance of this expression was almost completely abolished by application of siRNA sequences targeting the mRNA of those receptors (FIG. 3A(1) and FIG. 3A(2)).

On the functional level, FLS challenged with a combination of TNFa and IL-17 showed a production of e.g. IL-6 and MMP-3 (FIG. 3B(1) and FIG. 3B(2)). siRNA treatment led to a substantial diminution of the chemokine responses, consistent with those effects being completely dependent on the presence and functionality of the appropriate receptors. Simultaneous disruption of IL-17R and TNFRI signalling even increased this effect.

Example 5—Generation and Biochemical Characterisation of Bispecific Antibodies

Having shown the relevance of combining anti-TNFa and anti-IL-17 therapy for RA treatment, in particular by suppression of inflammation and synovitis as well as protection of bone and cartilage degeneration, we next generated bispecific antibodies for optimal combined inhibition of TNFa and IL-17 and tested their potency in different in vitro models.

As TNFa has been described on the surface of monocytes and T cells (Mitoma et al, Gastroenterology 2005), the role of avidity in the potency of bispecific antibodies was investigated. To this aim, we devised bispecific antibodies with different valencies for the respective ligands. Three lead formats were developed to generate bispecific TNFa:IL-17 antibodies based on the following architecture (see FIG. 5):

First, a bispecific antibody was generated, principally derived from a conventional IgG, in which one arm is directed against IL-17 and the second one against TNFa ("1+1"). Such a molecule consists of two different heavy chains and two different light chains which could lead to mixtures. In order to exclusively produce the desired isomer, the "CrossMab" design was used, which has been described elsewhere by Schaefer, Klein and others (Schaefer W et al., PNAS 2011). In this molecule, the light chain mispairing is avoided by exchange of the CH1-Cκ domains in the anti-IL-17 arm. The resulting molecule was designated "1+1 CrossMab".

In addition, a "2+2" molecule was generated in which two anti-IL-17 single chain Fabs (scFabs) were fused to the two N-terminal ends of a conventional (i.e. intact) anti-TNFa Mab. The antibody was called "2+2 scFab". Herein, to avoid mispairing, the anti-IL-17 light chain (VL+Ck) was fused to the anti-IL-17 heavy chain (VH+Ch1) using a Gly-Ser linker peptide $(G_4S)_6$ and the C-terminus of this scFab was fused to the N-terminal end of the anti-TNFa IgG heavy chain using a Gly-Ser connector peptide $(G_3S)_3$.

Additional molecules with "2+2" architecture were generated without use of linkers within the Fabs. Such molecules contains two different light chains, and—in analogy to the CrossMab format cited above—light chain mispairing was avoided by exchange of the heavy and light chain constant domains in the Fabs situated at the C-termini of the molecule. For example in this format anti-IL-17 crossed "heavy" chains (VH+Ck) were fused via a Gly-Ser connector peptide $(G4S)_4$ to both C-terminal ends of the heavy chains of an intact anti-TNFa mAb, and the corresponding anti-IL-17 "light" chains were crossed accordingly (VL+CH1). Alternatively, anti-TNFa crossed "heavy" chains (VH+CK) were fused via a Gly-Ser connector peptide (G4S)4 to both C-terminal ends of the heavy chains of an anti-IL-17 mAb, and the corresponding anti-TNFa "light" chains were crossed accordingly (VL+Ch1). The resulting bispecific format was termed "2+2 CrossMab".

All bispecific antibodies were purified from the supernatants of transfected HEK293 cells (see Material & Methods) and analyzed for integrity and functionality. For all 1+1 and 2+2 bispecific antibody constructs used in this study, Biacore analyses using the protocol already described above demonstrated functionality of both binding moieties towards the respective antigens.

The bispecific antibodies retained binding to IL-17A/A, IL-17A/F and TNFa in direct comparison to their parental anti-IL-17 and anti-TNFa antibodies (Table 1). Further simultaneous binding to both IL-17 and TNFa, and cross-reactivity with cynomolgus monkey IL-17A/A was also shown (Table 2). Moreover, binding to FcgRIIIa was demonstrated for all formats.

TABLE 1

Biacore Determinations of antibody functional affinity.

| Antibody | IL-17 A/A* (app KD) | IL-17 A/F (KD) | IL-17 F/F (KD) | TNFa (app KD) |
|---|---|---|---|---|
| BiSp Parental IL-17A #136 | 0.18 nM | 0.26 nM | NB | — |
| BiSp Parental IL-17A #134 | 0.13 nM | 0.27 nM | — | — |
| BiSp Parental Adalimumab | — | — | — | 0.016 nM |
| 1 + 1 TNFa crossed IL-17A[#136] (#10) | 0.33 nM | 0.24 nM | — | 0.027 nM |
| 1 + 1 TNFa scFab IL-17A[#136] (#12) | 0.41 nM | 0.25 nM | — | 0.034 nM |
| 1 + 1 IL-17[#134] crossed TNFa (#22) | 0.02 nM | 0.50 nM | — | 0.015 nM |
| 2 + 2 IL-17[#136] scFab TNFa mab (#13) | 0.04 nM | 0.24 nM | — | 0.039 nM |
| 2 + 2 TNFa crossed IL-17[#136] mab (#14) | 0.30 nM | 0.29 nM | — | 0.019 nM |
| 2 + 2 IL-17[#134] crossed TNFa mab (#16) | 0.09 nM | 1.11 nM | — | 0.032 nM |

(NB means no binding detected) app KD = apparent KD.

The chosen SPR setup uses IL17 in solution, therefore avidity effects of IL17A antibodies can only be excluded for "monomeric" IL17A/F, but not for "dimeric" IL17A/A.

TABLE 2

Biacore determinations of antibody binding

| Antibody | Simultaneous binding to IL-17A + TNFa | Cyno IL-17A/A* | FcγRIIIa |
|---|---|---|---|
| BiSp Parental IL-17A #136 | − | + | + |
| BiSp Parental IL-17A #134 | − | + | + |
| BiSp Parental Adalimumab | − | − | + |
| 1 + 1 TNFa crossed, IL-17A[#136] (#10) | + | + | + |
| 1 + 1 TNFa scFab, IL-17[#136] (#12) | + | + | + |
| 1 + 1 IL-17[#134] crossed TNFa (#22) | + | + | + |
| 2 + 2 IL-17[#136] scFab TNFa mab (#13) | + | + | + |
| 2 + 2 TNFa crossed IL-17[#136] mab (#14) | + | + | + |
| 2 + 2 IL-17[#134] crossed TNFa mab (#16) | + | + | + |

The stability of the 2+2 CrossMab and 2+2 scFab antibodies was assessed, and compared with that of a dual variable domain (DVD) bispecific antibody against IL-17 and TNF (anti-IL-17/TNFa DVD, or DVD_TNFa-IL-17; DVD_HC_D2-GS10-B6-17 DVD Sequences 667-671 in WO2010/102251 and DVD_LC_E7-GS10-B6-17 DVD Sequences 672-676 in WO2010/102251). The formats of the various 2+2 CrossMab and 2+2 scFab are shown in FIGS. 4B(1)-4B(12), and the stability data are shown in FIG. 5.

The antibodies may have improved stability (and may have high stability) compared with the anti-IL-17/TNFa DVD (FIG. 5). The anti-IL-17/TNFa DVD showed significant aggregation at about 55° C., whereas the antibodies of the invention showed no significant aggregation at about 55° C.

The antibodies of the invention comprising anti-IL-17 #134 Fabs have further improved stability compared with antibodies of the invention comprising anti-IL-17 #136 Fabs. For example antibody #29 (2+2 CrossMab comprising anti-IL-17#134 Fabs) is more stable than antibody #14 (2+2 CrossMab comprising anti-IL-17#136 Fabs), as shown in FIG. 5.

The antibodies of the invention comprising additional disulphide bridges have relatively high stabilities. For example the 2+2 ScFv antibody #30 is more stable than the DVD_TNFa-IL-17 antibody, as shown in FIG. 5.

The effects on antibody stability of inclusion of the IL-17#134 sequences and of inclusion of additional disulphide bonds are additive. This is evidenced by antibody #28, which is a 2+2 CrossMab comprising anti-IL-17#134 sequences and additional disulphide bonds, and which has higher stability than antibody #16, which is a 2+2 CrossMab comprising anti-IL-17#134 sequences without additional disulphide bonds (FIG. 5).

The measured aggregation onset temperatures for various antibodies were as follows:

| Antibody | T agg (° C.) |
|---|---|
| #13 | 58 |
| #14 | 55 |
| #16 | 58 |
| #26 | 55 |
| #27 | 64 |
| #28 | 59 |

-continued

| Antibody | T agg (° C.) |
|---|---|
| #29 | 58 |
| #30 | 62 |
| DVD_TNF-IL17 | 53 |

Example 6—Inhibition of Cytokine Production Induced by IL-17, TNFa, or IL-17 and TNFa in Combination in Human Synovial Fibroblasts Using Bispecific Antibodies After integrity, specificity and affinity of the different anti-IL-17:TNFa bispecific antibody constructs was evaluated, the functional activity of those entities was characterized in disease-relevant assays.

First, the single anti-IL-17 or anti-TNFa component of the different bispecific antibodies was assessed for the inhibition of an IL-17- or a TNFa-induced production of pro-inflammatory cytokines (IL-6, IL-8 and RANTES production) by HFLS-RA in reference to the parental mAbs.

In Table 3 the IC50 values are shown exemplarily for the inhibition of selected cytokines, demonstrating (a) the functionality of the bispecific antibodies, as the reported IC50 values were comparable to those of the parental antibodies, and (b) the differences between several antibody formats and the superiority of the bivalent ("2+2") antibody formats compared to the monovalent molecule.

TABLE 3

Inhibitory potential of bispecific vs. parental antibodies upon FLS stimulation with TNFa or IL-17.

| | RA-FLS | | | |
|---|---|---|---|---|
| | IL-17 treatment (10 ng/ml) | | TNFa treatment (1 ng/ml) | |
| Antibody | IC50 IL-6 [nM] | IC50 IL-8 [nM] | IC50 IL-6 [nM] | IC50 IL-8 [nM] |
| Adalimumab | n.t. | n.t. | 0.018 | 0.014 |
| Anti-IL-17 134 | 1.83 | 0.98 | n.t. | n.t. |
| 1 + 1 CrossMab (#22) | n.c. | 6.06 | 0.79 | 0.33 |
| 2 + 2 scFab (#13) | 0.39 | 0.41 | 0.13 | 0.10 |
| 2 + 2 CrossMab (#16) | 0.39 | 0.33 | 0.04 | 0.03 |

RA-FLS were cultured as described above and stimulated either with IL-17 or TNFa in the presence of titrated antibody amounts. After 72 hours IL-6 and IL-8 TNFa production was assessed in the supernatant. Shown are the IC50 values regarding the cytokine inhibition of different antibodies (n.t.=not tested; n.c. not calculable, although about 70% inhibition was observable).

There were also slight differences observed between the two 2+2 formats, in particular the advantage of the 2+2 CrossMab compared to the 2+2 scFab, which can be explained by a 2+2 CrossMab having improved accessibility of the anti-TNFa binding moiety.

Those data were confirmed by similar studies using A375 melanoma cell line (Table 4).

TABLE 4

Inhibition of IL-17 or TNFa induced interleukin-8 production in A375 cells

| Antibody | TNFa stimulation IC50 [nM] | IL-17 stimulation IC50 [nM] |
|---|---|---|
| Adalimumab | 0.016 | n.t. |
| Anti-IL-17 136 | n.t. | 1.092 |
| Anti-IL-17 134 | n.t. | 0.846 |
| 1 + 1 CrossMab #22 | 0.198 | 8.852 |
| 2 + 2 scFab #13 | 0.068 | 0.709 |
| 2 + 2 CrossMab #16 | 0.034 | 0.423 |

The functionality of the single components of shown anti-IL-17/TNFa bispecific antibodies was tested by their capacity to inhibit either an IL-17 or a TNFa-induced production of interleukin-8 by human A375 cells. Briefly, $2\times10^4$ A375 cells per well were cultured overnight before pre-incubation with titrated amounts (0-150/500 nM) of indicated bispecific antibodies in comparison to parental antibodies and addition of 10 ng/ml of recombinant human IL-17A or 1 ng/ml of recombinant human TNFa, respectively. After 24 hrs, supernatants were analyzed for IL-8 production by CBA (BD Biosciences). Shown are the mean IC50 values [nM] out of duplicates for the inhibition of the IL-8 secretion induced by the single stimuli (n.t.=not tested)

The functionality of the bispecific antibodies was also shown in an assay setup with human chondrocytes as described above. All molecules tested were able to reduce an IL-17 or TNFa induced MMP-3 production at comparable antibody levels, whereas again the "2+2" bispecific antibody format was more potent (i.e. effective at lower concentrations) (Table 5).

TABLE 5

Inhibition of MMP-3 production in TNFa or IL-17 chondrocytes by bispecific vs. parental antibodies.

| Antibody | IL-17 treatment IC50 [M] | TNFa treatment IC50 [M] | Combination treatment IC50 [M] |
|---|---|---|---|
| Adalimumab | n.t. | $2.828 \times 10^{-9}$ | $2.115 \times 10^{-9}$ |
| Anti-IL-17 134 | $3.357 \times 10^{-8}$ | n.t.* | $1.231 \times 10^{-7}$ |
| 1 + 1 CrossMab #22 | $3.801 \times 10^{-7}$ | $1.157 \times 10^{-8}$ | $5.381 \times 10^{-8}$ |
| 2 + 2 scFab #13 | $3.586 \times 10^{-8}$ | $1.952 \times 10^{-8}$ | $6.098 \times 10^{-9}$ |
| 2 + 2 CrossMab #16 | $9.385 \times 10^{-9}$ | $2.799 \times 10^{-9}$ | $2.605 \times 10^{-9}$ |

Chondrocytes were cultured as described before and stimulated either with IL-7 (10 ng/ml) or TNFa (0.1 ng/ml) or combination in the presence of titrated antibody amounts. Shown are the IC50 values [M] of the MMP-3 inhibition by indicated antibodies (n.t.=not tested).

Bispecific Antibodies Inhibit Cytokine and MMP Secretion in FLS or Chondrocytes Upon Double Stimulation RA-FLS were challenged either with TNFa, IL-17 or combination, thus Adalimumab, anti-IL-17 #134, 1+1 CrossMab #22, 2+2 scFab #13 and 2+2 CrossMab #16 as already described and were either left untreated or pre-incubated with an anti-IL-17 or anti-TNFa or bispecific antibody.

In agreement with the above results, in cells stimulated with IL-17 and TNFa in combination, there was a clear either additive or synergistic effect in the inhibition of IL-6, IL-8, G-CSF and RANTES production of the bispecific antibodies compared with the parental antibodies. Anti-IL- 17 or anti-TNFa antibodies alone prevented the cytokine induction upon single treatment by the respective stimulus, which was also true for all bispecific antibodies (FIG. 6 A, FIG. 6B, FIG. 6C, FIG. 6D, FIG. 6E, FIG. 6F, FIG. 6G, and FIG. 6H).

In particular upon stimulation with both ligands, there were superior inhibitory effects of the bispecific antibodies compared with parental antibodies (exemplarily shown for one out of two RA-FLS donors tested). This was true for the majority of detected analytes (e.g. IL-8, G-CSF, RANTES) and was further confirmed in chondrocyte experiments, in which different bispecific antibody formats also inhibited the production of MMP3 upon combo challenge (Table 3).

The 2+2 CrossMab antibody #16) consistently showed improved performance compared with the 1+1 CrossMab bispecific antibody #22 in different biological assays. This improved potency could not be explained by just a two-fold increase in binding sites, because the Biacore data do not point towards a bivalent of binding of 2+2 bispecific antibody to a single TNFa trimer or IL-17A dimer molecule (Table 1). In the biological (potency) assays, binding of cell membrane-bound TNFa (mTNFa) may play a role as was reported elsewhere for example in monocytes or T cells (ten Hove T et al., Gut 2002; Shen C et al., Aliment Pharmacol Ther. 2005; Nesbitt et al., Inflamm Bowel Dis 2007).

We generated a Fab fragment of the anti-TNFa antibody and measured its potency in functional assays. Although the anti-TNFa Fab retained its functionality by preventing a TNFa-induced production of Interleukin-8 in A375 cells, there was a clearly reduced activity (IC50 of 0.02 nM (IgG) vs. 0.431 nM (Fab), confirming that the decreased potency of the 1+1 format is due its monovalent binding mode.

Abbreviations

BFR bone formation rate
FLS Fibroblast-like synoviocytes
G-CSF Granulocyte colony-stimulating factor
MMP matrix metalloproteinase
RANTES Chemokine ligand 5, also known as CCL5. Abbr for Regulated on Activation, Normal T cell Expressed and Secreted.
TNFRSF1A TNF receptor, also known as TNFR1 and CD120a

NON-PATENT REFERENCES

Ash Z et al., Expert Opin Biol Ther 2012; 12(9): 1277-1289.
Atzeni F et al., Curr Opin Investig Drugs 2009: 10(11); 1204-11: 2040-3429.
Canete J. D., Pablos J. L. Current Topics in Medicinal Chemistry 2013; 6: 752-759.
Diarra, D., et al., 2007. Nat. Med. 13:156.
Geisse, S., et al., Protein Expr. Purif. 8 (1996) 271-282.
Genovese M. C. et al., Arthritis & Rheumatism 2004; 50(5): 1412-1419.
Hellings, P. W. et al., Am. J. Resp. Cell Mol. Biol. 2003; 28: 42-50.
Hueber A J, et al. J Immunol 2010; 184(7): 3336-3340.
Kaufman, R. J., Mol. Biotechnol. 16 (2000) 151-160.
Keffer, J., et al. 1991. EMBO J. 10:4025.
Kehlen A et al., Clin Exp Immunol 2002.
Koenders M I., et al. Arthritis & Rheumatism 2011; 63(8): 2329-2339.
Kotake S. et al., Clin Invest 1999; 103(9):1345-52.
Li X et al., Biochem Biophys Res Comm 2010
Makrides, S. C., Protein Expr. Purif. 17 (1999) 183-202.
McInness I. B., and Schett G. NEJM 2011; 365: 2205-2219.
Mitoma H, et al., Gastroenterology 2005: 128(2): 376-392.
Nesbitt A, et al., Inflamm Bowel Dis 2007; 13(11): 1323-1332.
Osol ed., Remington's Pharmaceutical Sciences, Mack Publishing., 1980.
Pieringer H, et al., Current Pharmaceutical Design 2013.
Qi J, et al., Int Immunopharmacol. 2012; 14(4):770-8.
Robinson ed., Sustained and Controlled Release Drug Delivery Systems, Marcel Dekker, Inc., New York, 1978
Sadik C D et al., PLoS One 2011
Schaefer W, et al., PNAS 2011; 108(27): 11187-11192.
Shen C, et al., J. Aliment Pharmacol Ther. 2005; 21(3): 251-258.
ten Hove T, et al., Gut 2002; 50: 206-211.
van den Berg W B, et al., Nat. Rev. Rheumatol. 2009; 5: 549-553.
Weinblatt et al., Ann.Rheum.Dis. 2007
Werner, R. G., Arzneimittelforschung (Drug Res.) 48 (1998) 870-880
Woodrick R et al., Bull NYU Hosp Jt Dis. 2010; 68(3): 211-7.
Zhang Y, et al., Int Immunopharmacol. 2013; 15(2):199-205.
Ziolkowska M, et al., Journal of Immunology, 2000; 164 (5):2832-2838.

The invention claimed is:

1. A bispecific tetravalent antibody against IL-17 and TNFa, the antibody comprising two heavy chains, two first soluble chains, and two second soluble chains,
wherein each heavy chain comprises, from N-terminus to C-terminus:
a first VH domain,
a CH1 domain,
a CH2 domain,
a CH3 domain, and either
(i) a second VL domain and a CH1 domain, or
(ii) a second VH domain and a CL domain and;
wherein the two first soluble chains each comprise, from N-terminus to C-terminus, a first VL domain and a first CL domain, and wherein the two second soluble chains each comprise, from N-terminus to C-terminus, either
(i) a second VL domain and a CH1 domain, or
(ii) a second VH domain and a CL domain;
wherein each of the first soluble chains is associated with a respective heavy chain to provide a first antigen-binding site comprising a first VH domain and a first VL domain, thereby providing two first antigen-binding sites, and each of the second soluble chains is associated with a respective heavy chain to provide a second antigen-binding site comprising a second VH domain and a second VL domain, thereby providing two second antigen-binding sites; and
wherein either (i) each first antigen-binding site is an IL-17 binding site and each second antigen-binding site is a TNFa binding site; or (ii) each first antigen-binding site is a TNFa binding site and each second antigen-binding site is an IL-17 binding site, wherein:
a) each binding site against IL-17 comprises a VH domain and a VL domain, wherein the VH domain comprises CDRH1 of SEQ ID NO: 1, CDRH2 of SEQ ID NO: 2, and CDRH3 of SEQ ID NO: 3, and wherein the VL domain comprises CDRL1 of SEQ ID NO:4, CDRL2 of SEQ ID NO: 5, and CDRL3 of SEQ ID NO:6; and
b) each binding site against TNFa comprises a VH domain and a VL domain, wherein the VH domain comprises CDRH1 of SEQ ID NO: 31, CDRH2 of SEQ ID NO: 32, and CDRH3 of SEQ ID NO: 33, and wherein the VL domain CDRL1 of SEQ ID NO:34, CDRL2 of SEQ ID NO: 35, and CDRL3 of SEQ ID NO: 36.

2. The antibody according to claim 1, wherein the first antigen-binding sites are IL-17 binding sites and the second antigen-binding sites are TNFa binding sites.

3. The antibody according to claim 1, wherein the first antigen-binding sites are TNFa binding sites and the second antigen-binding sites are IL-17 binding sites.

4. The antibody according to claim 1, wherein:
a) each binding site against IL-17 comprises
(i) the VH domain of SEQ ID NO: 8 and the VL domain of SEQ ID NO: 10; or
(ii) the VH domain of SEQ ID NO: 12 and the VL domain of SEQ ID NO: 14; and
b) each binding site against TNFa comprises the VH of SEQ ID NO: 38 and the VL domain of SEQ ID NO: 40.

5. The antibody according to claim 1, wherein
a) each binding site against IL-17 comprises the VH domain of SEQ ID NO:8 or SEQ ID NO:12; and
b) each binding site against TNFa comprises the VH domain of SEQ ID NO: 38.

6. The antibody according to claim 5, wherein
a) each binding site against IL-17 comprises the VL domain of SEQ ID NO: 10, or SEQ ID NO: 14; and
b) each binding site against TNFa comprises the VL domain of SEQ ID NO: 40.

7. The antibody according to claim 1, wherein each heavy chain has the amino acid sequence of SEQ ID NO: 48, each first soluble chain has the amino acid sequence of SEQ ID NO: 54, and each second soluble chain has the amino acid sequence of SEQ ID NO: 55.

8. The antibody according to claim 1, wherein the antibody comprises one or more disulphide bonds between a light chain variable domain and a heavy chain variable domain.

9. The antibody according to claim 8 comprising a disulphide bond between amino acid VH44 and amino acid VL100, according to Kabat numbering.

10. The antibody according to claim 1, which has high stability, defined as an aggregation onset temperature of >58° C. in a 1 mg/ml formulation in 20 mM His/HisCl, 140 mM NaCl solution at pH 6.0.

11. The antibody according to claim 1, wherein the antibody inhibits the production of IL-6 and/or IL-8 in response to IL-17 in RA-FLS with an IC50 value of 1.0 nM or less.

12. The antibody according to claim 1, wherein the antibody inhibits the production of IL-6 and/or IL-8 in response to TNFa in RA-FLS with an IC50 value of 0.2 nM or less.

13. The antibody according to claim 1, wherein the antibody inhibits MMP production in response to IL-17/TNFa combined stimulation in chondrocytes with an IC50 value of $1\times10^{-8}$ nM or less.

14. The antibody according to claim 1, wherein the antibody binds to an IL-17A/A homodimer with an apparent KD of 0.5 nM or less.

15. The antibody according to claim 1, which binds IL-17A/A homodimers and IL-17A/F heterodimers, and does not bind IL-17F/F homodimers.

16. An isolated nucleic acid which comprises one or more nucleotide sequences encoding the bispecific tetravalent antibody according to claim 1, or the heavy chain or the soluble chain of said bispecific tetravalent antibody.

17. An expression vector or a set of expression vectors collectively for expression of the bispecific tetravalent antibody of claim 1, the expression vector or set of expression vectors collectively comprising nucleotide sequences encoding the bispecific tetravalent antibody according to claim 1, or the heavy chains, the first soluble chains, or the second soluble chains of said bispecific tetravalent antibody, wherein the nucleotide sequences are operably linked to a promoter.

18. A host cell carrying the expression vector or set of expression vectors of claim 17.

19. A method of producing a bispecific tetravalent antibody, the method comprising culturing host cells according to claim 18 under conditions for production of said bispecific tetravalent antibody.

20. A method according to claim 19 further comprising recovering said bispecific tetravalent antibody.

21. A method according to claim 20 further comprising formulating the bispecific tetravalent antibody into a composition including at least one additional component.

22. A composition comprising the bispecific tetravalent antibody of claim 1 and a pharmaceutically acceptable carrier.

23. A method for the treatment of rheumatoid arthritis, said method comprising administering to a subject in need of treatment an effective amount of an antibody according to claim 1 or the composition of claim 22.

* * * * *

SEQUENCE LISTING

```
<160> NUMBER OF SEQ ID NOS: 82

<210> SEQ ID NO 1
<211> LENGTH: 5
<212> TYPE: PRT
<213> ORGANISM: Artificial Sequence
<220> FEATURE:
<223> OTHER INFORMATION: #134 and 136 VH CDR 1 amino acid sequence

<400> SEQUENCE: 1

Ser Tyr Gly Val His
1               5

<210> SEQ ID NO 2
<211> LENGTH: 16
<212> TYPE: PRT
<213> ORGANISM: Artificial Sequence
<220> FEATURE:
```

```
<223> OTHER INFORMATION: #134 and 136 VH CDR 2 amino acid sequence

<400> SEQUENCE: 2

Val Ile Trp Ser Asp Gly Thr Thr Thr Tyr Asn Ser Ala Leu Lys Ser
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: #134 and 136 VH CDR 3 amino acid sequence

<400> SEQUENCE: 3

Asp Thr His Tyr Arg Leu Tyr Tyr Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: #134 and 136 VL CDR 1 amino acid sequence

<400> SEQUENCE: 4

Arg Ser Ser Gln Ser Leu Val His Ser Asn Gly Asp Thr Tyr Phe His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: #134 and 136 VL CDR 2 amino acid sequence

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: #134 and 136 VL CDR 3 amino acid sequence

<400> SEQUENCE: 6

Ser Gln Thr Thr His Ala Pro Phe Thr
1               5

<210> SEQ ID NO 7
<211> LENGTH: 364
<212> TYPE: DNA
<213> ORGANISM: Artificial Sequence
<220> FEATURE:
<223> OTHER INFORMATION: #134 VH domain nucleotide sequence

<400> SEQUENCE: 7
gaggtgcagc tggtcgagag cggcggaggg ctggtgcagc caggcggcag cctgaggctg      60
tcctgcgccg ccagcggctt cagcctggac agctacggcg tgcactgggt gcggcaggcc    120
ccaggcaagg gcctggaatg ggtgtccgtg atctggtccg acggcaccac cacctacaac    180
agcgccctga gagcaggtt caccatcagc agggacaaca gcaagaacac cctgtacctg    240
cagatgaaca gcctgagggc cgaggacacc gccgtgtact actgcgccag ggacacacac    300
```

```
tacaggctgt actattacgc catggattac tggggccagg gtaccaccgt gaccgtctcc    360
tcag                                                                 364
```

<210> SEQ ID NO 8
<211> LENGTH: 121
<212> TYPE: PRT
<213> ORGANISM: Artificial Sequence
<220> FEATURE:
<223> OTHER INFORMATION: #134 VH domain amino acid sequence

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser
        115                 120
```

<210> SEQ ID NO 9
<211> LENGTH: 337
<212> TYPE: DNA
<213> ORGANISM: Artificial Sequence
<220> FEATURE:
<223> OTHER INFORMATION: #134 VL domain nucleotide sequence

<400> SEQUENCE: 9

```
gacatcgtga tgacccagag ccccctgagc ctgcccgtga cccaggcga gcccgctagc     60 atcagctgca ggtccagcca gagcctggtg cacagcaacg gcgacaccta cttccactgg   120
tatctgcaga agcccggcca gtccccccag ctgctgatct acaaggtgtc caacaggttc   180
agcggcgtgc ccgacaggtt ctccggcagc ggctccggca ccgacttcac cctgaagatc   240
agcagggtgg aggccgagga cgtgggcgtg tactactgca gccagaccac ccacgccccc   300
ttcaccttcg gccagggcac caagctggag atcaaac                            337
```

<210> SEQ ID NO 10
<211> LENGTH: 112
<212> TYPE: PRT
<213> ORGANISM: Artificial Sequence
<220> FEATURE:
<223> OTHER INFORMATION: #134 VL domain amino acid sequence

<400> SEQUENCE: 10

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45
```

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

<210> SEQ ID NO 11
<211> LENGTH: 364
<212> TYPE: DNA
<213> ORGANISM: Artificial Sequence
<220> FEATURE:
<223> OTHER INFORMATION: #136 VH domain nucleotide sequence

<400> SEQUENCE: 11
gaggtgcagc tggtcgagag cggcggaggg ctggtgcagc caggcggcag cctgaggctg      60
tcctgcgccg ccagcggctt cagcctggac agctacggcg tgcactgggt gcggcaggcc     120
accggcaagg gcctggaatg ggtgtccgtg atctggtccg acggcaccac cacctacaac     180
agcgccctga gagcaggttt caccatcagc agggagaacg ccaagaacag cctgtacctg     240
cagatgaaca gcctgagggc cggcgacacc gccgtgtact actgcgccag ggacacacac     300
tacaggctgt actattacgc catggattac tggggccagg gtaccaccgt gaccgtctcc     360
tcag                                                                 364

<210> SEQ ID NO 12
<211> LENGTH: 121
<212> TYPE: PRT
<213> ORGANISM: Artificial Sequence
<220> FEATURE:
<223> OTHER INFORMATION: #136 VH domain amino acid sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Thr Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser
        115                 120

<210> SEQ ID NO 13
<211> LENGTH: 337
<212> TYPE: DNA
<213> ORGANISM: Artificial Sequence
<220> FEATURE:
<223> OTHER INFORMATION: #136 VL domain nucleotide sequence

<400> SEQUENCE: 13

```
gacatcgtga tgacccagag cccctgagc ctgcccgtga ccccaggcga gcccgctagc      60
atcagctgca ggtccagcca gagcctggtg cacagcaacg gcgacaccta cttccactgg    120
tatctgcaga agcccggcca gtccccccag ctgctgatct acaaggtgtc caacaggttc    180
agcggcgtgc ccgacaggtt ctccggcagc ggctccggca ccgacttcac cctgaagatc    240
agcagggtgg aggccgagga cgtgggcgtg tactactgca gccagaccac ccacgccccc    300
ttcaccttcg gccagggcac caagctggag atcaaac                             337
```

```
<210> SEQ ID NO 14
<211> LENGTH: 112
<212> TYPE: PRT
<213> ORGANISM: Artificial Sequence
<220> FEATURE:
<223> OTHER INFORMATION: #136 VL domain amino acid sequence

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110
```

```
<210> SEQ ID NO 15
<211> LENGTH: 30
<212> TYPE: PRT
<213> ORGANISM: Artificial Sequence
<220> FEATURE:
<223> OTHER INFORMATION: #134 VH FR1 amino acid sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp
            20                  25                  30
```

```
<210> SEQ ID NO 16
<211> LENGTH: 14
<212> TYPE: PRT
<213> ORGANISM: Artificial Sequence
<220> FEATURE:
<223> OTHER INFORMATION: #134 VH FR2 amino acid sequence

<400> SEQUENCE: 16

Trp Val Arg Gln Ala Pro Gly Lys Gly Leu Glu Trp Val Ser
1               5                   10
```

```
<210> SEQ ID NO 17
<211> LENGTH: 32
<212> TYPE: PRT
<213> ORGANISM: Artificial Sequence
<220> FEATURE:
```

<223> OTHER INFORMATION: #134 VH FR3 amino acid sequence

<400> SEQUENCE: 17

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: #134 VH FR4 amino acid sequence

<400> SEQUENCE: 18

Trp Gly Gln Gly Thr Thr Val Thr Val Ser Ser
1               5                   10

<210> SEQ ID NO 19
<211> LENGTH: 23
<212> TYPE: PRT
<213> ORGANISM: Artificial Sequence
<220> FEATURE:
<223> OTHER INFORMATION: #134 VL FR1 amino acid sequence

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 20
<211> LENGTH: 15
<212> TYPE: PRT
<213> ORGANISM: Artificial Sequence
<220> FEATURE:
<223> OTHER INFORMATION: #134 VL FR2 amino acid sequence

<400> SEQUENCE: 20

Trp Tyr Leu Gln Lys Pro Gly Gln Ser Pro Gln Leu Leu Ile Tyr
1               5                   10                  15

<210> SEQ ID NO 21
<211> LENGTH: 32
<212> TYPE: PRT
<213> ORGANISM: Artificial Sequence
<220> FEATURE:
<223> OTHER INFORMATION: #134 VL FR3 amino acid sequence

<400> SEQUENCE: 21

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 22
<211> LENGTH: 10
<212> TYPE: PRT
<213> ORGANISM: Artificial Sequence
<220> FEATURE:
<223> OTHER INFORMATION: #134 VL FR4 amino acid sequence

<400> SEQUENCE: 22

Phe Gly Gln Gly Thr Lys Leu Glu Ile Lys

<210> SEQ ID NO 23
<211> LENGTH: 30
<212> TYPE: PRT
<213> ORGANISM: Artificial Sequence
<220> FEATURE:
<223> OTHER INFORMATION: #136 VH FR1 amino acid sequence

<400> SEQUENCE: 23

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ser Leu Asp
            20                  25                  30

<210> SEQ ID NO 24
<211> LENGTH: 14
<212> TYPE: PRT
<213> ORGANISM: Artificial Sequence
<220> FEATURE:
<223> OTHER INFORMATION: #136 VH FR2 amino acid sequence

<400> SEQUENCE: 24

Trp Val Arg Gln Ala Thr Gly Lys Gly Leu Glu Trp Val Ser
 1               5                  10

<210> SEQ ID NO 25
<211> LENGTH: 32
<212> TYPE: PRT
<213> ORGANISM: Artificial Sequence
<220> FEATURE:
<223> OTHER INFORMATION: #136 VH FR3 amino acid sequence

<400> SEQUENCE: 25

Arg Phe Thr Ile Ser Arg Glu Asn Ala Lys Asn Ser Leu Tyr Leu Gln
 1               5                  10                  15
Met Asn Ser Leu Arg Ala Gly Asp Thr Ala Val Tyr Tyr Cys Ala Arg
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: #136 VH FR4 amino acid sequence

<400> SEQUENCE: 26

Trp Gly Gln Gly Thr Thr Val Thr Val Ser Ser
 1               5                  10

<210> SEQ ID NO 27
<211> LENGTH: 23
<212> TYPE: PRT
<213> ORGANISM: Artificial Sequence
<220> FEATURE:
<223> OTHER INFORMATION: #136 VL FR1 amino acid sequence

<400> SEQUENCE: 27

Asp Ile Val Met Thr Gln Ser Pro Leu Ser Leu Pro Val Thr Pro Gly
 1               5                  10                  15
Glu Pro Ala Ser Ile Ser Cys
            20

<210> SEQ ID NO 28
<211> LENGTH: 15

```
<212> TYPE: PRT
<213> ORGANISM: Artificial Sequence
<220> FEATURE:
<223> OTHER INFORMATION: #136 VL FR2 amino acid sequence

<400> SEQUENCE: 28

Trp Tyr Leu Gln Lys Pro Gly Gln Ser Pro Gln Leu Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: #136 VL FR3 amino acid sequence

<400> SEQUENCE: 29

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 30
<211> LENGTH: 10
<212> TYPE: PRT
<213> ORGANISM: Artificial Sequence
<220> FEATURE:
<223> OTHER INFORMATION: #136 VL FR4 amino acid sequence

<400> SEQUENCE: 30

Phe Gly Gln Gly Thr Lys Leu Glu Ile Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: VH CDR 1 amino acid sequence

<400> SEQUENCE: 31

Gly Phe Thr Phe Asp Asp Tyr Ala Met His
1               5                   10

<210> SEQ ID NO 32
<211> LENGTH: 17
<212> TYPE: PRT
<213> ORGANISM: Artificial Sequence
<220> FEATURE:
<223> OTHER INFORMATION: VH CDR 2 amino acid sequence

<400> SEQUENCE: 32

Ala Ile Thr Trp Asn Ser Gly His Ile Asp Tyr Ala Asp Ser Val Glu
1               5                   10                  15

Gly

<210> SEQ ID NO 33
<211> LENGTH: 12
<212> TYPE: PRT
<213> ORGANISM: Artificial Sequence
<220> FEATURE:
<223> OTHER INFORMATION: VH CDR 3 amino acid sequence

<400> SEQUENCE: 33

Val Ser Tyr Leu Ser Thr Ala Ser Ser Leu Asp Tyr
1               5                   10
```

<210> SEQ ID NO 34
<211> LENGTH: 11
<212> TYPE: PRT
<213> ORGANISM: Artificial Sequence
<220> FEATURE:
<223> OTHER INFORMATION: VL CDR 1 amino acid sequence

<400> SEQUENCE: 34

Arg Ala Ser Gln Gly Ile Arg Asn Tyr Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: VL CDR 2 amino acid sequence

<400> SEQUENCE: 35

Ala Ala Ser Thr Leu Gln Ser
1               5

<210> SEQ ID NO 36
<211> LENGTH: 9
<212> TYPE: PRT
<213> ORGANISM: Artificial Sequence
<220> FEATURE:
<223> OTHER INFORMATION: VL CDR 3 amino acid sequence

<400> SEQUENCE: 36

Gln Arg Tyr Asn Arg Ala Pro Tyr Thr
1               5

<210> SEQ ID NO 37
<211> LENGTH: 364
<212> TYPE: DNA
<213> ORGANISM: Artificial Sequence
<220> FEATURE:
<223> OTHER INFORMATION: VH domain nucleotide sequence

<400> SEQUENCE: 37
gaggtgcaac tggtcgaaag cggcggggga ctcgtccagc ccggcaggtc cctgagactt      60
tcttgcgccg cttcaggttt cacctttgac gattacgcaa tgcactgggt ccgccaggcc     120
cctgggaagg gcctggagtg ggtcagcgct atcacatgga actccggaca tattgactat     180
gcagattctg ttgagggtcg gttcaccatc agtagggaca tgccaaaaa cagcctctac      240 ctgcagatga atagcttgag agctgaagac actgcagtgt attactgtgc caaggtctct     300
tacctgtcaa cagcaagctc cctcgattat tggggccaag ggaccctggt gactgtctcc     360
tcag                                                                  364

<210> SEQ ID NO 38
<211> LENGTH: 121
<212> TYPE: PRT
<213> ORGANISM: Artificial Sequence
<220> FEATURE:
<223> OTHER INFORMATION: VH domain amino acid sequence

<400> SEQUENCE: 38

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

```
Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser
        115                 120

<210> SEQ ID NO 39
<211> LENGTH: 322
<212> TYPE: DNA
<213> ORGANISM: Artificial Sequence
<220> FEATURE:
<223> OTHER INFORMATION: VL domain nucleotide sequence

<400> SEQUENCE: 39
gacatccaga tgacccagag cccctcctct ctgtcagcca gcgtgggcga tagggtcaca      60
attacctgca gagcttccca gggcatccgc aactacctcg catggtatca gcaaagcct     120 ggaaaagccc caaagctgct tatttacgct gcatctactc tgcagagtgg cgtgcccagc    180
cggttctccg gttctgggtc aggcacagac tttacccctca ctatcagctc cctgcagcct    240
gaggatgtcg ccacctatta ctgtcagaga tacaatagag ctccatatac attcggacaa    300
ggaaccaagg tcgaaatcaa ac                                             322

<210> SEQ ID NO 40
<211> LENGTH: 107
<212> TYPE: PRT
<213> ORGANISM: Artificial Sequence
<220> FEATURE:
<223> OTHER INFORMATION: VL domain amino acid sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
                100                 105

<210> SEQ ID NO 41
<211> LENGTH: 451
<212> TYPE: PRT
<213> ORGANISM: Artificial Sequence
<220> FEATURE:
<223> OTHER INFORMATION: IL-17 #134 heavy chain
```

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr His Tyr Arg Leu Tyr Tyr Ala Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
```

Asp Lys Ser Arg Trp Gln Gln Gly Asn Val Phe Ser Cys Ser Val Met
            405                 410                 415
420                 425                 430

His Glu Ala Leu His Asn His Tyr Thr Gln Lys Ser Leu Ser Leu Ser
            435                 440                 445

Pro Gly Lys
    450

<210> SEQ ID NO 42
<211> LENGTH: 219
<212> TYPE: PRT
<213> ORGANISM: Artificial Sequence
<220> FEATURE:
<223> OTHER INFORMATION: IL-17 #134 light chain

<400> SEQUENCE: 42

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 43
<211> LENGTH: 451
<212> TYPE: PRT
<213> ORGANISM: Artificial Sequence
<220> FEATURE:
<223> OTHER INFORMATION: IL-17 #136 heavy chain

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

-continued

Gly Val His Trp Val Arg Gln Ala Thr Gly Lys Gly Leu Glu Trp Val
            35                  40                  45
Ser Val Ile Trp Ser Asp Gly Thr Thr Thr Tyr Asn Ser Ala Leu Lys
 50                  55                  60
Ser Arg Phe Thr Ile Ser Arg Glu Asn Ala Lys Asn Ser Leu Tyr Leu
 65                  70                  75                  80
Gln Met Asn Ser Leu Arg Ala Gly Asp Thr Ala Val Tyr Tyr Cys Ala
                85                  90                  95
Arg Asp Thr His Tyr Arg Leu Tyr Tyr Ala Met Asp Tyr Trp Gly
            100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys

<210> SEQ ID NO 44
<211> LENGTH: 219
<212> TYPE: PRT
<213> ORGANISM: Artificial Sequence
<220> FEATURE:
<223> OTHER INFORMATION: IL-17 #136 light chain

<400> SEQUENCE: 44

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 45
<211> LENGTH: 451
<212> TYPE: PRT
<213> ORGANISM: Artificial Sequence
<220> FEATURE:
<223> OTHER INFORMATION: Adalimumab heavy chain

<400> SEQUENCE: 45

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 46
<211> LENGTH: 214
<212> TYPE: PRT
<213> ORGANISM: Artificial Sequence
<220> FEATURE:
<223> OTHER INFORMATION: Adalimumab light chain
```

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 47
<211> LENGTH: 699
<212> TYPE: PRT
<213> ORGANISM: Artificial Sequence
<220> FEATURE:
<223> OTHER INFORMATION: #14 heavy chain

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Thr Gly Lys Gly Leu Glu Trp Val
        35                  40                  45

Ser Val Ile Trp Ser Asp Gly Thr Thr Thr Tyr Asn Ser Ala Leu Lys
50                  55                  60

Ser Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

```
Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys Gly Gly Gly Gly Ser Gly Gly Gly Gly Ser Gly Gly Gly
                450                 455                 460

Gly Ser Gly Gly Gly Gly Ser Glu Val Gln Leu Val Glu Ser Gly Gly
465                 470                 475                 480

Gly Leu Val Gln Pro Gly Arg Ser Leu Arg Leu Ser Cys Ala Ala Ser
                485                 490                 495

Gly Phe Thr Phe Asp Asp Tyr Ala Met His Trp Val Arg Gln Ala Pro
                500                 505                 510

Gly Lys Gly Leu Glu Trp Val Ser Ala Ile Thr Trp Asn Ser Gly His
                515                 520                 525

Ile Asp Tyr Ala Asp Ser Val Glu Gly Arg Phe Thr Ile Ser Arg Asp
530                 535                 540

Asn Ala Lys Asn Ser Leu Tyr Leu Gln Met Asn Ser Leu Arg Ala Glu
```

```
545                 550                 555                 560
Asp Thr Ala Val Tyr Tyr Cys Ala Lys Val Ser Tyr Leu Ser Thr Ala
                565                 570                 575

Ser Ser Leu Asp Tyr Trp Gly Gln Gly Thr Leu Val Thr Val Ser Ser
                580                 585                 590

Ala Ser Val Ala Ala Pro Ser Val Phe Ile Phe Pro Pro Ser Asp Glu
                595                 600                 605

Gln Leu Lys Ser Gly Thr Ala Ser Val Val Cys Leu Leu Asn Asn Phe
                610                 615                 620

Tyr Pro Arg Glu Ala Lys Val Gln Trp Lys Val Asp Asn Ala Leu Gln
625                 630                 635                 640

Ser Gly Asn Ser Gln Glu Ser Val Thr Glu Gln Asp Ser Lys Asp Ser
                645                 650                 655

Thr Tyr Ser Leu Ser Ser Thr Leu Thr Leu Ser Lys Ala Asp Tyr Glu
                660                 665                 670

Lys His Lys Val Tyr Ala Cys Glu Val Thr His Gln Gly Leu Ser Ser
                675                 680                 685

Pro Val Thr Lys Ser Phe Asn Arg Gly Glu Cys
                690                 695

<210> SEQ ID NO 48
<211> LENGTH: 699
<212> TYPE: PRT
<213> ORGANISM: Artificial Sequence
<220> FEATURE:
<223> OTHER INFORMATION: #16 heavy chain

<400> SEQUENCE: 48

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Ala Ile Thr Trp Asn Ser Gly His Ile Asp Tyr Ala Asp Ser Val
                50                  55                  60

Glu Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
```

```
            210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Phe Ser Leu Asp Ser Tyr Gly Val His Trp Val Arg Gln Ala Pro
            500                 505                 510

Gly Lys Gly Leu Glu Trp Val Ser Val Ile Trp Ser Asp Gly Thr Thr
        515                 520                 525

Thr Tyr Asn Ser Ala Leu Lys Ser Arg Phe Thr Ile Ser Arg Asp Asn
    530                 535                 540

Ser Lys Asn Thr Leu Tyr Leu Gln Met Asn Ser Leu Arg Ala Glu Asp
545                 550                 555                 560

Thr Ala Val Tyr Tyr Cys Ala Arg Asp Thr His Tyr Arg Leu Tyr Tyr
                565                 570                 575

Tyr Ala Met Asp Tyr Trp Gly Gln Gly Thr Thr Val Thr Val Ser Ser
            580                 585                 590

Ala Ser Val Ala Ala Pro Ser Val Phe Ile Phe Pro Pro Ser Asp Glu
        595                 600                 605

Gln Leu Lys Ser Gly Thr Ala Ser Val Val Cys Leu Leu Asn Asn Phe
    610                 615                 620

Tyr Pro Arg Glu Ala Lys Val Gln Trp Lys Val Asp Asn Ala Leu Gln
625                 630                 635                 640
```

Ser Gly Asn Ser Gln Glu Ser Val Thr Glu Gln Asp Ser Lys Asp Ser
                645                 650                 655

Thr Tyr Ser Leu Ser Ser Thr Leu Thr Leu Ser Lys Ala Asp Tyr Glu
            660                 665                 670

Lys His Lys Val Tyr Ala Cys Glu Val Thr His Gln Gly Leu Ser Ser
        675                 680                 685

Pro Val Thr Lys Ser Phe Asn Arg Gly Glu Cys
    690                 695

<210> SEQ ID NO 49
<211> LENGTH: 699
<212> TYPE: PRT
<213> ORGANISM: Artificial Sequence
<220> FEATURE:
<223> OTHER INFORMATION: #28 heavy chain

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Val Ser Tyr Leu Ser Thr Ala Ser Ser Leu Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
    290                 295                 300

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Gly Gly Gly
            450                 455                 460

Gly Ser Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Phe Ser Leu Asp Ser Tyr Gly Val His Trp Val Arg Gln Ala Pro
            500                 505                 510

Gly Lys Cys Leu Glu Trp Val Ser Val Ile Trp Ser Asp Gly Thr Thr
            515                 520                 525

Thr Tyr Asn Ser Ala Leu Lys Ser Arg Phe Thr Ile Ser Arg Asp Asn
530                 535                 540

Ser Lys Asn Thr Leu Tyr Leu Gln Met Asn Ser Leu Arg Ala Glu Asp
545                 550                 555                 560

Thr Ala Val Tyr Tyr Cys Ala Arg Asp Thr His Tyr Arg Leu Tyr Tyr
                565                 570                 575

Tyr Ala Met Asp Tyr Trp Gly Gln Gly Thr Thr Val Thr Val Ser Ser
            580                 585                 590

Ala Ser Val Ala Ala Pro Ser Val Phe Ile Phe Pro Pro Ser Asp Glu
            595                 600                 605

Gln Leu Lys Ser Gly Thr Ala Ser Val Val Cys Leu Leu Asn Asn Phe
            610                 615                 620

Tyr Pro Arg Glu Ala Lys Val Gln Trp Lys Val Asp Asn Ala Leu Gln
625                 630                 635                 640

Ser Gly Asn Ser Gln Glu Ser Val Thr Glu Gln Asp Ser Lys Asp Ser
            645                 650                 655

Thr Tyr Ser Leu Ser Ser Thr Leu Thr Leu Ser Lys Ala Asp Tyr Glu
            660                 665                 670

Lys His Lys Val Tyr Ala Cys Glu Val Thr His Gln Gly Leu Ser Ser
            675                 680                 685

Pro Val Thr Lys Ser Phe Asn Arg Gly Glu Cys
            690                 695
```

<210> SEQ ID NO 50
<211> LENGTH: 699

<212> TYPE: PRT
<213> ORGANISM: Artificial Sequence
<220> FEATURE:
<223> OTHER INFORMATION: #29 heavy chain

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Gly Gly Gly Gly
        450                 455                 460

Gly Ser Gly Gly Gly Ser Glu Val Gln Leu Val Glu Ser Gly Gly
465                 470                 475                 480

Gly Leu Val Gln Pro Gly Arg Ser Leu Arg Leu Ser Cys Ala Ala Ser
            485                 490                 495

Gly Phe Thr Phe Asp Asp Tyr Ala Met His Trp Val Arg Gln Ala Pro
            500                 505                 510

Gly Lys Gly Leu Glu Trp Val Ser Ala Ile Thr Trp Asn Ser Gly His
        515                 520                 525

Ile Asp Tyr Ala Asp Ser Val Glu Gly Arg Phe Thr Ile Ser Arg Asp
530                 535                 540

Asn Ala Lys Asn Ser Leu Tyr Leu Gln Met Asn Ser Leu Arg Ala Glu
545                 550                 555                 560

Asp Thr Ala Val Tyr Tyr Cys Ala Lys Val Ser Tyr Leu Ser Thr Ala
            565                 570                 575

Ser Ser Leu Asp Tyr Trp Gly Gln Gly Thr Leu Val Thr Val Ser Ser
        580                 585                 590

Ala Ser Val Ala Ala Pro Ser Val Phe Ile Phe Pro Pro Ser Asp Glu
            595                 600                 605

Gln Leu Lys Ser Gly Thr Ala Ser Val Val Cys Leu Leu Asn Asn Phe
        610                 615                 620

Tyr Pro Arg Glu Ala Lys Val Gln Trp Lys Val Asp Asn Ala Leu Gln
625                 630                 635                 640

Ser Gly Asn Ser Gln Glu Ser Val Thr Glu Gln Asp Ser Lys Asp Ser
            645                 650                 655

Thr Tyr Ser Leu Ser Ser Thr Leu Thr Leu Ser Lys Ala Asp Tyr Glu
        660                 665                 670

Lys His Lys Val Tyr Ala Cys Glu Val Thr His Gln Gly Leu Ser Ser
            675                 680                 685

Pro Val Thr Lys Ser Phe Asn Arg Gly Glu Cys
        690                 695

<210> SEQ ID NO 51
<211> LENGTH: 219
<212> TYPE: PRT
<213> ORGANISM: Artificial Sequence
<220> FEATURE:
<223> OTHER INFORMATION: #14 first soluble chain

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215

<210> SEQ ID NO 52
<211> LENGTH: 219
<212> TYPE: PRT
<213> ORGANISM: Artificial Sequence
<220> FEATURE:
<223> OTHER INFORMATION: #29 first soluble chain

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Phe His Trp Tyr Leu Gln Lys Pro Gly Gln Ser
                35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 53
<211> LENGTH: 212
<212> TYPE: PRT
<213> ORGANISM: Artificial Sequence
<220> FEATURE:
<223> OTHER INFORMATION: #14 and #29 second soluble chain

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
        210

<210> SEQ ID NO 54
<211> LENGTH: 214
<212> TYPE: PRT
<213> ORGANISM: Artificial Sequence
<220> FEATURE:
<223> OTHER INFORMATION: #16 and #28 first soluble chain

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 55
<211> LENGTH: 217
<212> TYPE: PRT
<213> ORGANISM: Artificial Sequence
<220> FEATURE:
<223> OTHER INFORMATION: #16 second soluble chain

<400> SEQUENCE: 55

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                20                  25                  30

Asn Gly Asp Thr Tyr Phe His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Thr
                 85                  90                  95

Thr His Ala Pro Phe Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205
```

Asp Lys Lys Val Glu Pro Lys Ser Cys
    210             215

<210> SEQ ID NO 56
<211> LENGTH: 217
<212> TYPE: PRT
<213> ORGANISM: Artificial Sequence
<220> FEATURE:
<223> OTHER INFORMATION: #28 second soluble chain

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Cys Gly Thr Lys Leu Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys
    210             215

<210> SEQ ID NO 57
<211> LENGTH: 938
<212> TYPE: PRT
<213> ORGANISM: Artificial Sequence
<220> FEATURE:
<223> OTHER INFORMATION: #13 heavy chain

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

-continued

```
                65                  70                  75                  80
Ser Arg Val Glu Ala Glu Asp Val Gly Val Tyr Tyr Cys Ser Gln Thr
                        85                  90                  95
Thr His Ala Pro Phe Thr Phe Gly Cys Gly Thr Lys Leu Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys Gly Gly Gly Gly Ser
210                 215                 220
Gly Gly Gly Gly Ser Gly Gly Gly Ser Gly Gly Gly Gly Ser Gly
225                 230                 235                 240
Gly Gly Gly Ser Gly Gly Gly Ser Gly Gly Glu Val Gln Leu Val
                245                 250                 255
Glu Ser Gly Gly Gly Leu Val Gln Pro Gly Gly Ser Leu Arg Leu Ser
        260                 265                 270
Cys Ala Ala Ser Gly Phe Ser Leu Asp Ser Tyr Gly Val His Trp Val
        275                 280                 285
Arg Gln Ala Thr Gly Lys Cys Leu Glu Trp Val Ser Val Ile Trp Ser
        290                 295                 300
Asp Gly Thr Thr Thr Tyr Asn Ser Ala Leu Lys Ser Arg Phe Thr Ile
305                 310                 315                 320
Ser Arg Glu Asn Ala Lys Asn Ser Leu Tyr Leu Gln Met Asn Ser Leu
                325                 330                 335
Arg Ala Gly Asp Thr Ala Val Tyr Tyr Cys Ala Arg Asp Thr His Tyr
                340                 345                 350
Arg Leu Tyr Tyr Tyr Ala Met Asp Tyr Trp Gly Gln Gly Thr Thr Val
        355                 360                 365
Thr Val Ser Ser Ala Ser Thr Lys Gly Pro Ser Val Phe Pro Leu Ala
        370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
                405                 410                 415
Ala Leu Thr Ser Gly Val His Thr Phe Pro Ala Val Leu Gln Ser Ser
                420                 425                 430
Gly Leu Tyr Ser Leu Ser Ser Val Val Thr Val Pro Ser Ser Ser Leu
        435                 440                 445
Gly Thr Gln Thr Tyr Ile Cys Asn Val Asn His Lys Pro Ser Asn Thr
        450                 455                 460
Lys Val Asp Lys Lys Val Glu Pro Lys Ser Cys Gly Gly Gly Ser Gly
465                 470                 475                 480
Gly Gly Ser Gly Gly Ser Glu Val Gln Leu Val Glu Ser Gly Gly
                485                 490                 495
```

```
Gly Leu Val Gln Pro Gly Arg Ser Leu Arg Leu Ser Cys Ala Ala Ser
            500                 505                 510

Gly Phe Thr Phe Asp Asp Tyr Ala Met His Trp Val Arg Gln Ala Pro
            515                 520                 525

Gly Lys Gly Leu Glu Trp Val Ser Ala Ile Thr Trp Asn Ser Gly His
            530                 535                 540

Ile Asp Tyr Ala Asp Ser Val Glu Gly Arg Phe Thr Ile Ser Arg Asp
545                 550                 555                 560

Asn Ala Lys Asn Ser Leu Tyr Leu Gln Met Asn Ser Leu Arg Ala Glu
                565                 570                 575

Asp Thr Ala Val Tyr Tyr Cys Ala Lys Val Ser Tyr Leu Ser Thr Ala
            580                 585                 590

Ser Ser Leu Asp Tyr Trp Gly Gln Gly Thr Leu Val Thr Val Ser Ser
            595                 600                 605

Ala Ser Thr Lys Gly Pro Ser Val Phe Pro Leu Ala Pro Ser Ser Lys
            610                 615                 620

Ser Thr Ser Gly Gly Thr Ala Ala Leu Gly Cys Leu Val Lys Asp Tyr
625                 630                 635                 640

Phe Pro Glu Pro Val Thr Val Ser Trp Asn Ser Gly Ala Leu Thr Ser
                645                 650                 655

Gly Val His Thr Phe Pro Ala Val Leu Gln Ser Ser Gly Leu Tyr Ser
            660                 665                 670

Leu Ser Ser Val Val Thr Val Pro Ser Ser Ser Leu Gly Thr Gln Thr
            675                 680                 685

Tyr Ile Cys Asn Val Asn His Lys Pro Ser Asn Thr Lys Val Asp Lys
            690                 695                 700

Lys Val Glu Pro Lys Ser Cys Asp Lys Thr His Thr Cys Pro Pro Cys
705                 710                 715                 720

Pro Ala Pro Glu Leu Leu Gly Gly Pro Ser Val Phe Leu Phe Pro Pro
                725                 730                 735

Lys Pro Lys Asp Thr Leu Met Ile Ser Arg Thr Pro Glu Val Thr Cys
            740                 745                 750

Val Val Val Asp Val Ser His Glu Asp Pro Glu Val Lys Phe Asn Trp
            755                 760                 765

Tyr Val Asp Gly Val Glu Val His Asn Ala Lys Thr Lys Pro Arg Glu
            770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815

Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
            835                 840                 845

Leu Thr Lys Asn Gln Val Ser Leu Thr Cys Leu Val Lys Gly Phe Tyr
            850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910
```

Val Phe Ser Cys Ser Val Met His Glu Ala Leu His Asn His Tyr Thr
            915                 920                 925

Gln Lys Ser Leu Ser Leu Ser Pro Gly Lys
            930                 935

<210> SEQ ID NO 58
<211> LENGTH: 938
<212> TYPE: PRT
<213> ORGANISM: Artificial Sequence
<220> FEATURE:
<223> OTHER INFORMATION: #26 heavy chain

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Cys Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Ser Gly Gly Gly Gly Ser Gly
225                 230                 235                 240

Gly Gly Gly Ser Gly Gly Gly Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Ser Leu Asp Ser Tyr Gly Val His Trp Val
        275                 280                 285

Arg Gln Ala Pro Gly Lys Cys Leu Glu Trp Val Ser Val Ile Trp Ser
    290                 295                 300

Asp Gly Thr Thr Thr Tyr Asn Ser Ala Leu Lys Ser Arg Phe Thr Ile
305                 310                 315                 320

Ser Arg Asp Asn Ser Lys Asn Thr Leu Tyr Leu Gln Met Asn Ser Leu
                325                 330                 335

-continued

```
Arg Ala Glu Asp Thr Ala Val Tyr Tyr Cys Ala Arg Asp Thr His Tyr
                340                 345                 350
Arg Leu Tyr Tyr Tyr Ala Met Asp Tyr Trp Gly Gln Gly Thr Thr Val
            355                 360                 365
Thr Val Ser Ser Ala Ser Thr Lys Gly Pro Ser Val Phe Pro Leu Ala
        370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
                405                 410                 415
Ala Leu Thr Ser Gly Val His Thr Phe Pro Ala Val Leu Gln Ser Ser
            420                 425                 430
Gly Leu Tyr Ser Leu Ser Ser Val Val Thr Val Pro Ser Ser Ser Leu
        435                 440                 445
Gly Thr Gln Thr Tyr Ile Cys Asn Val Asn His Lys Pro Ser Asn Thr
    450                 455                 460
Lys Val Asp Lys Lys Val Glu Pro Lys Ser Cys Gly Gly Gly Ser Gly
465                 470                 475                 480
Gly Gly Ser Gly Gly Gly Ser Glu Val Gln Leu Val Glu Ser Gly Gly
                485                 490                 495
Gly Leu Val Gln Pro Gly Arg Ser Leu Arg Leu Ser Cys Ala Ala Ser
            500                 505                 510
Gly Phe Thr Phe Asp Asp Tyr Ala Met His Trp Val Arg Gln Ala Pro
        515                 520                 525
Gly Lys Gly Leu Glu Trp Val Ser Ala Ile Thr Trp Asn Ser Gly His
    530                 535                 540
Ile Asp Tyr Ala Asp Ser Val Glu Gly Arg Phe Thr Ile Ser Arg Asp
545                 550                 555                 560
Asn Ala Lys Asn Ser Leu Tyr Leu Gln Met Asn Ser Leu Arg Ala Glu
                565                 570                 575
Asp Thr Ala Val Tyr Tyr Cys Ala Lys Val Ser Tyr Leu Ser Thr Ala
            580                 585                 590
Ser Ser Leu Asp Tyr Trp Gly Gln Gly Thr Leu Val Thr Val Ser Ser
        595                 600                 605
Ala Ser Thr Lys Gly Pro Ser Val Phe Pro Leu Ala Pro Ser Ser Lys
    610                 615                 620
Ser Thr Ser Gly Gly Thr Ala Ala Leu Gly Cys Leu Val Lys Asp Tyr
625                 630                 635                 640
Phe Pro Glu Pro Val Thr Val Ser Trp Asn Ser Gly Ala Leu Thr Ser
                645                 650                 655
Gly Val His Thr Phe Pro Ala Val Leu Gln Ser Ser Gly Leu Tyr Ser
            660                 665                 670
Leu Ser Ser Val Val Thr Val Pro Ser Ser Ser Leu Gly Thr Gln Thr
        675                 680                 685
Tyr Ile Cys Asn Val Asn His Lys Pro Ser Asn Thr Lys Val Asp Lys
    690                 695                 700
Lys Val Glu Pro Lys Ser Cys Asp Lys Thr His Thr Cys Pro Pro Cys
705                 710                 715                 720
Pro Ala Pro Glu Leu Leu Gly Gly Pro Ser Val Phe Leu Phe Pro Pro
                725                 730                 735
Lys Pro Lys Asp Thr Leu Met Ile Ser Arg Thr Pro Glu Val Thr Cys
            740                 745                 750
Val Val Val Asp Val Ser His Glu Asp Pro Glu Val Lys Phe Asn Trp
```

```
                755                 760                 765
Tyr Val Asp Gly Val Glu Val His Asn Ala Lys Thr Lys Pro Arg Glu
            770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815

Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
        835                 840                 845

Leu Thr Lys Asn Gln Val Ser Leu Thr Cys Leu Val Lys Gly Phe Tyr
    850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
        915                 920                 925

Gln Lys Ser Leu Ser Leu Ser Pro Gly Lys
    930                 935

<210> SEQ ID NO 59
<211> LENGTH: 938
<212> TYPE: PRT
<213> ORGANISM: Artificial Sequence
<220> FEATURE:
<223> OTHER INFORMATION: #27 heavy chain

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

-continued

```
                180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys Gly Gly Gly Gly Ser
            210                 215                 220
Gly Gly Gly Gly Ser Gly Gly Gly Ser Gly Gly Gly Ser Gly
225                 230                 235                 240
Gly Gly Gly Ser Gly Gly Gly Ser Gly Gly Glu Val Gln Leu Val
            245                 250                 255
Glu Ser Gly Gly Gly Leu Val Gln Pro Gly Gly Ser Leu Arg Leu Ser
            260                 265                 270
Cys Ala Ala Ser Gly Phe Ser Leu Asp Ser Tyr Gly Val His Trp Val
            275                 280                 285
Arg Gln Ala Pro Gly Lys Gly Leu Glu Trp Val Ser Val Ile Trp Ser
            290                 295                 300
Asp Gly Thr Thr Thr Tyr Asn Ser Ala Leu Lys Ser Arg Phe Thr Ile
305                 310                 315                 320
Ser Arg Asp Asn Ser Lys Asn Thr Leu Tyr Leu Gln Met Asn Ser Leu
            325                 330                 335
Arg Ala Glu Asp Thr Ala Val Tyr Tyr Cys Ala Arg Asp Thr His Tyr
            340                 345                 350
Arg Leu Tyr Tyr Tyr Ala Met Asp Tyr Trp Gly Gln Gly Thr Thr Val
            355                 360                 365
Thr Val Ser Ser Ala Ser Thr Lys Gly Pro Ser Val Phe Pro Leu Ala
            370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
            405                 410                 415
Ala Leu Thr Ser Gly Val His Thr Phe Pro Ala Val Leu Gln Ser Ser
            420                 425                 430
Gly Leu Tyr Ser Leu Ser Ser Val Val Thr Val Pro Ser Ser Ser Leu
            435                 440                 445
Gly Thr Gln Thr Tyr Ile Cys Asn Val Asn His Lys Pro Ser Asn Thr
            450                 455                 460
Lys Val Asp Lys Lys Val Glu Pro Lys Ser Cys Gly Gly Gly Ser Gly
465                 470                 475                 480
Gly Gly Ser Gly Gly Gly Ser Glu Val Gln Leu Val Glu Ser Gly Gly
            485                 490                 495
Gly Leu Val Gln Pro Gly Arg Ser Leu Arg Leu Ser Cys Ala Ala Ser
            500                 505                 510
Gly Phe Thr Phe Asp Asp Tyr Ala Met His Trp Val Arg Gln Ala Pro
            515                 520                 525
Gly Lys Gly Leu Glu Trp Val Ser Ala Ile Thr Trp Asn Ser Gly His
            530                 535                 540
Ile Asp Tyr Ala Asp Ser Val Glu Gly Arg Phe Thr Ile Ser Arg Asp
545                 550                 555                 560
Asn Ala Lys Asn Ser Leu Tyr Leu Gln Met Asn Ser Leu Arg Ala Glu
            565                 570                 575
Asp Thr Ala Val Tyr Tyr Cys Ala Lys Val Ser Tyr Leu Ser Thr Ala
            580                 585                 590
Ser Ser Leu Asp Tyr Trp Gly Gln Gly Thr Leu Val Thr Val Ser Ser
            595                 600                 605
```

-continued

```
Ala Ser Thr Lys Gly Pro Ser Val Phe Pro Leu Ala Pro Ser Ser Lys
            610                 615                 620

Ser Thr Ser Gly Gly Thr Ala Ala Leu Gly Cys Leu Val Lys Asp Tyr
625                 630                 635                 640

Phe Pro Glu Pro Val Thr Val Ser Trp Asn Ser Gly Ala Leu Thr Ser
                645                 650                 655

Gly Val His Thr Phe Pro Ala Val Leu Gln Ser Ser Gly Leu Tyr Ser
            660                 665                 670

Leu Ser Ser Val Val Thr Val Pro Ser Ser Ser Leu Gly Thr Gln Thr
            675                 680                 685

Tyr Ile Cys Asn Val Asn His Lys Pro Ser Asn Thr Lys Val Asp Lys
            690                 695                 700

Lys Val Glu Pro Lys Ser Cys Asp Lys Thr His Thr Cys Pro Pro Cys
705                 710                 715                 720

Pro Ala Pro Glu Leu Leu Gly Gly Pro Ser Val Phe Leu Phe Pro Pro
                725                 730                 735

Lys Pro Lys Asp Thr Leu Met Ile Ser Arg Thr Pro Glu Val Thr Cys
            740                 745                 750

Val Val Val Asp Val Ser His Glu Asp Pro Glu Val Lys Phe Asn Trp
            755                 760                 765

Tyr Val Asp Gly Val Glu Val His Asn Ala Lys Thr Lys Pro Arg Glu
770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815

Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
            835                 840                 845

Leu Thr Lys Asn Gln Val Ser Leu Thr Cys Leu Val Lys Gly Phe Tyr
            850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
            915                 920                 925

Gln Lys Ser Leu Ser Leu Ser Pro Gly Lys
    930                 935

<210> SEQ ID NO 60
<211> LENGTH: 933
<212> TYPE: PRT
<213> ORGANISM: Artificial Sequence
<220> FEATURE:
<223> OTHER INFORMATION: #30 heavy chain

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30
```

```
Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gly Gly Gly Ser Gly Gly Gly Gly Ser Gly
225                 230                 235                 240

Gly Gly Gly Ser Gly Gly Glu Val Gln Leu Val Glu Ser Gly Gly Gly
                245                 250                 255

Leu Val Gln Pro Gly Arg Ser Leu Arg Leu Ser Cys Ala Ala Ser Gly
            260                 265                 270

Phe Thr Phe Asp Asp Tyr Ala Met His Trp Val Arg Gln Ala Pro Gly
        275                 280                 285

Lys Gly Leu Glu Trp Val Ser Ala Ile Thr Trp Asn Ser Gly His Ile
290                 295                 300

Asp Tyr Ala Asp Ser Val Glu Gly Arg Phe Thr Ile Ser Arg Asp Asn
305                 310                 315                 320

Ala Lys Asn Ser Leu Tyr Leu Gln Met Asn Ser Leu Arg Ala Glu Asp
                325                 330                 335

Thr Ala Val Tyr Tyr Cys Ala Lys Val Ser Tyr Leu Ser Thr Ala Ser
            340                 345                 350

Ser Leu Asp Tyr Trp Gly Gln Gly Thr Leu Val Thr Val Ser Ser Ala
        355                 360                 365

Ser Thr Lys Gly Pro Ser Val Phe Pro Leu Ala Pro Ser Ser Lys Ser
    370                 375                 380

Thr Ser Gly Gly Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
            420                 425                 430

Ser Ser Val Val Thr Val Pro Ser Ser Ser Leu Gly Thr Gln Thr Tyr
        435                 440                 445
```

```
Ile Cys Asn Val Asn His Lys Pro Ser Asn Thr Lys Val Asp Lys Lys
    450                 455                 460

Val Glu Pro Lys Ser Cys Gly Gly Gly Ser Gly Gly Gly Ser Gly Gly
465                 470                 475                 480

Gly Ser Glu Val Gln Leu Val Glu Ser Gly Gly Gly Leu Val Gln Pro
                    485                 490                 495

Gly Gly Ser Leu Arg Leu Ser Cys Ala Ala Ser Gly Phe Ser Leu Asp
                500                 505                 510

Ser Tyr Gly Val His Trp Val Arg Gln Ala Pro Gly Lys Gly Leu Glu
            515                 520                 525

Trp Val Ser Val Ile Trp Ser Asp Gly Thr Thr Tyr Asn Ser Ala
530                 535                 540

Leu Lys Ser Arg Phe Thr Ile Ser Arg Asp Asn Ser Lys Asn Thr Leu
545                 550                 555                 560

Tyr Leu Gln Met Asn Ser Leu Arg Ala Glu Asp Thr Ala Val Tyr Tyr
                565                 570                 575

Cys Ala Arg Asp Thr His Tyr Arg Leu Tyr Tyr Ala Met Asp Tyr
                580                 585                 590

Trp Gly Gln Gly Thr Thr Val Thr Val Ser Ser Ala Ser Thr Lys Gly
            595                 600                 605

Pro Ser Val Phe Pro Leu Ala Pro Ser Ser Lys Ser Thr Ser Gly Gly
        610                 615                 620

Thr Ala Ala Leu Gly Cys Leu Val Lys Asp Tyr Phe Pro Glu Pro Val
625                 630                 635                 640

Thr Val Ser Trp Asn Ser Gly Ala Leu Thr Ser Gly Val His Thr Phe
                645                 650                 655

Pro Ala Val Leu Gln Ser Ser Gly Leu Tyr Ser Leu Ser Ser Val Val
                660                 665                 670

Thr Val Pro Ser Ser Ser Leu Gly Thr Gln Thr Tyr Ile Cys Asn Val
            675                 680                 685

Asn His Lys Pro Ser Asn Thr Lys Val Asp Lys Lys Val Glu Pro Lys
        690                 695                 700

Ser Cys Asp Lys Thr His Thr Cys Pro Pro Cys Pro Ala Pro Glu Leu
705                 710                 715                 720

Leu Gly Gly Pro Ser Val Phe Leu Phe Pro Pro Lys Pro Lys Asp Thr
                725                 730                 735

Leu Met Ile Ser Arg Thr Pro Glu Val Thr Cys Val Val Val Asp Val
                740                 745                 750

Ser His Glu Asp Pro Glu Val Lys Phe Asn Trp Tyr Val Asp Gly Val
            755                 760                 765

Glu Val His Asn Ala Lys Thr Lys Pro Arg Glu Glu Gln Tyr Asn Ser
770                 775                 780

Thr Tyr Arg Val Val Ser Val Leu Thr Val Leu His Gln Asp Trp Leu
785                 790                 795                 800

Asn Gly Lys Glu Tyr Lys Cys Lys Val Ser Asn Lys Ala Leu Pro Ala
                805                 810                 815

Pro Ile Glu Lys Thr Ile Ser Lys Ala Lys Gly Gln Pro Arg Glu Pro
            820                 825                 830

Gln Val Tyr Thr Leu Pro Pro Ser Arg Asp Glu Leu Thr Lys Asn Gln
            835                 840                 845

Val Ser Leu Thr Cys Leu Val Lys Gly Phe Tyr Pro Ser Asp Ile Ala
850                 855                 860

Val Glu Trp Glu Ser Asn Gly Gln Pro Glu Asn Asn Tyr Lys Thr Thr
```

```
                865                 870                 875                 880
Pro Pro Val Leu Asp Ser Asp Gly Ser Phe Phe Leu Tyr Ser Lys Leu
                    885                 890                 895

Thr Val Asp Lys Ser Arg Trp Gln Gln Gly Asn Val Phe Ser Cys Ser
                    900                 905                 910

Val Met His Glu Ala Leu His Asn His Tyr Thr Gln Lys Ser Leu Ser
                    915                 920                 925

Leu Ser Pro Gly Lys
        930

<210> SEQ ID NO 61
<211> LENGTH: 214
<212> TYPE: PRT
<213> ORGANISM: Artificial Sequence
<220> FEATURE:
<223> OTHER INFORMATION: #13, #26 and #27 light chain

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 62
<211> LENGTH: 219
<212> TYPE: PRT
<213> ORGANISM: Artificial Sequence
<220> FEATURE:
<223> OTHER INFORMATION: #30 light chain

<400> SEQUENCE: 62

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 63
<211> LENGTH: 451
<212> TYPE: PRT
<213> ORGANISM: Artificial Sequence
<220> FEATURE:
<223> OTHER INFORMATION: #10 and #12 heavy chain 'holes'

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asp Ser Tyr
            20                  25                  30

Gly Val His Trp Val Arg Gln Ala Thr Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Val Val Thr Val
        180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Asp Glu Leu Thr Lys Asn Gln Val Ser
        355                 360                 365
Leu Ser Cys Ala Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 64
<211> LENGTH: 455
<212> TYPE: PRT
<213> ORGANISM: Artificial Sequence
<220> FEATURE:
<223> OTHER INFORMATION: #10 and #12 heavy chain 'knobs'

<400> SEQUENCE: 64

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ser Ala Ile Thr Trp Asn Ser Gly His Ile Asp Tyr Ala Asp Ser Val
    50                  55                  60
```

```
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Cys Arg Asp Glu Leu Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 65
<211> LENGTH: 219
<212> TYPE: PRT
```

<213> ORGANISM: Artificial Sequence
<220> FEATURE:
<223> OTHER INFORMATION: #10 and #12 light chain

<400> SEQUENCE: 65

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 66
<211> LENGTH: 212
<212> TYPE: PRT
<213> ORGANISM: Artificial Sequence
<220> FEATURE:
<223> OTHER INFORMATION: #10 'light' chain ('crossed')

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Ser Ser Ala Ser Thr
            100                 105                 110
```

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Leu Gly Thr Gln Thr Tyr Ile Cys
            180                 185                 190

Asn Val Asn His Lys Pro Ser Asn Thr Lys Val Asp Lys Lys Val Glu
            195                 200                 205

Pro Lys Ser Cys
    210

<210> SEQ ID NO 67
<211> LENGTH: 697
<212> TYPE: PRT
<213> ORGANISM: Artificial Sequence
<220> FEATURE:
<223> OTHER INFORMATION: #12 heavy chain scFab 'knobs'

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gly Gly Gly Ser Gly Gly Gly Ser Gly
225                 230                 235                 240

Gly Gly Gly Ser Gly Gly Glu Val Gln Leu Val Glu Ser Gly Gly
                245                 250                 255

```
Leu Val Gln Pro Gly Arg Ser Leu Arg Leu Ser Cys Ala Ala Ser Gly
            260                 265                 270

Phe Thr Phe Asp Asp Tyr Ala Met His Trp Val Arg Gln Ala Pro Gly
        275                 280                 285

Lys Gly Leu Glu Trp Val Ser Ala Ile Thr Trp Asn Ser Gly His Ile
    290                 295                 300

Asp Tyr Ala Asp Ser Val Glu Gly Arg Phe Thr Ile Ser Arg Asp Asn
305                 310                 315                 320

Ala Lys Asn Ser Leu Tyr Leu Gln Met Asn Ser Leu Arg Ala Glu Asp
                325                 330                 335

Thr Ala Val Tyr Tyr Cys Ala Lys Val Ser Tyr Leu Ser Thr Ala Ser
            340                 345                 350

Ser Leu Asp Tyr Trp Gly Gln Gly Thr Leu Val Thr Val Ser Ser Ala
        355                 360                 365

Ser Thr Lys Gly Pro Ser Val Phe Pro Leu Ala Pro Ser Ser Lys Ser
    370                 375                 380

Thr Ser Gly Gly Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
            420                 425                 430

Ser Ser Val Val Thr Val Pro Ser Ser Ser Leu Gly Thr Gln Thr Tyr
        435                 440                 445

Ile Cys Asn Val Asn His Lys Pro Ser Asn Thr Lys Val Asp Lys Lys
    450                 455                 460

Val Glu Pro Lys Ser Cys Asp Lys Thr His Thr Cys Pro Pro Cys Pro
465                 470                 475                 480

Ala Pro Glu Leu Leu Gly Gly Pro Ser Val Phe Leu Phe Pro Pro Lys
                485                 490                 495

Pro Lys Asp Thr Leu Met Ile Ser Arg Thr Pro Glu Val Thr Cys Val
            500                 505                 510

Val Val Asp Val Ser His Glu Asp Pro Glu Val Lys Phe Asn Trp Tyr
        515                 520                 525

Val Asp Gly Val Glu Val His Asn Ala Lys Thr Lys Pro Arg Glu Glu
    530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Ala Leu Pro Ala Pro Ile Glu Lys Thr Ile Ser Lys Ala Lys Gly Gln
            580                 585                 590

Pro Arg Glu Pro Gln Val Tyr Thr Leu Pro Pro Cys Arg Asp Glu Leu
        595                 600                 605

Thr Lys Asn Gln Val Ser Leu Trp Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Lys Leu Thr Val Asp Lys Ser Arg Trp Gln Gln Gly Asn Val
            660                 665                 670

Phe Ser Cys Ser Val Met His Glu Ala Leu His Asn His Tyr Thr Gln
```

```
                    675                 680                 685

Lys Ser Leu Ser Leu Ser Pro Gly Lys
    690                 695

<210> SEQ ID NO 68
<211> LENGTH: 451
<212> TYPE: PRT
<213> ORGANISM: Artificial Sequence
<220> FEATURE:
<223> OTHER INFORMATION: #22 heavy chain 'holes'

<400> SEQUENCE: 68

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
                340             345             350
Cys Thr Leu Pro Pro Ser Arg Asp Glu Leu Thr Lys Asn Gln Val Ser
            355             360             365

Leu Ser Cys Ala Val Lys Gly Phe Tyr Pro Ser Asp Ile Ala Val Glu
        370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Val Ser Lys Leu Thr Val
                405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
        435             440             445

Pro Gly Lys
    450

<210> SEQ ID NO 69
<211> LENGTH: 455
<212> TYPE: PRT
<213> ORGANISM: Artificial Sequence
<220> FEATURE:
<223> OTHER INFORMATION: #22 heavy chain 'knobs'

<400> SEQUENCE: 69

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Ser Leu Asp Ser Tyr
            20                  25                  30

Gly Val His Trp Val Arg Gln Ala Pro Gly Lys Gly Leu Glu Trp Val
        35                  40                  45

Ser Val Ile Trp Ser Asp Gly Thr Thr Thr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr His Tyr Arg Leu Tyr Tyr Tyr Ala Met Asp Tyr Trp Gly
            100                 105                 110

Gln Gly Thr Thr Val Thr Val Ser Ser Ala Ser Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
```

```
                        245                 250                 255
Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Cys Arg Asp Glu Leu Thr Lys
        355                 360                 365

Asn Gln Val Ser Leu Trp Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 70
<211> LENGTH: 214
<212> TYPE: PRT
<213> ORGANISM: Artificial Sequence
<220> FEATURE:
<223> OTHER INFORMATION: #22 light chain

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
            145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 71
<211> LENGTH: 217
<212> TYPE: PRT
<213> ORGANISM: Artificial Sequence
<220> FEATURE:
<223> OTHER INFORMATION: #22 'light' chain ('crossed')

<400> SEQUENCE: 71

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Phe His Trp Tyr Leu Gln Lys Pro Gly Gln Ser
                35                  40                  45

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys
            210                 215

<210> SEQ ID NO 72
<211> LENGTH: 155
<212> TYPE: PRT
<213> ORGANISM: Homo sapiens

<400> SEQUENCE: 72

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30
```

```
Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
     50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
                115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 73
<211> LENGTH: 155
<212> TYPE: PRT
<213> ORGANISM: Macaca fascicularis

<400> SEQUENCE: 73

Met Thr Pro Gly Lys Thr Ser Leu Val Leu Leu Leu Leu Leu Leu Ser
  1               5                  10                  15

Leu Glu Ala Ile Val Lys Ala Gly Ile Ala Ile Pro Arg Asn Ser Gly
             20                  25                  30

Cys Pro Asn Ser Glu Asp Lys Asn Phe Pro Arg Thr Val Met Val Asn
            35                  40                  45

Leu Asn Ile His Asn Arg Asn Thr Ser Thr Asn Pro Lys Arg Ser Ser
     50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Val Lys Ala Asp Gly Asn Val Asp Tyr His Met Asn Ser
                100                 105                 110

Val Pro Ile Gln Gln Glu Ile Leu Val Leu Arg Arg Glu Pro Arg His
                115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 74
<211> LENGTH: 233
<212> TYPE: PRT
<213> ORGANISM: Homo sapiens

<400> SEQUENCE: 74

Met Ser Thr Glu Ser Met Ile Arg Asp Val Glu Leu Ala Glu Glu Ala
  1               5                  10                  15

Leu Pro Lys Lys Thr Gly Gly Pro Gln Gly Ser Arg Arg Cys Leu Phe
             20                  25                  30

Leu Ser Leu Phe Ser Phe Leu Ile Val Ala Gly Ala Thr Thr Leu Phe
             35                  40                  45
```

```
Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 75
<211> LENGTH: 937
<212> TYPE: PRT
<213> ORGANISM: Artificial Sequence
<220> FEATURE:
<223> OTHER INFORMATION: #13 heavy chain variant lacking Lys938

<400> SEQUENCE: 75

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
                 20                  25                  30

Asn Gly Asp Thr Tyr Phe His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Thr
                 85                  90                  95

Thr His Ala Pro Phe Thr Phe Gly Cys Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

-continued

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Gly Gly Gly Ser Gly
225                 230                 235                 240

Gly Gly Gly Ser Gly Gly Gly Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Ser Leu Asp Ser Tyr Gly Val His Trp Val
            275                 280                 285

Arg Gln Ala Thr Gly Lys Cys Leu Glu Trp Val Ser Val Ile Trp Ser
            290                 295                 300

Asp Gly Thr Thr Thr Tyr Asn Ser Ala Leu Lys Ser Arg Phe Thr Ile
305                 310                 315                 320

Ser Arg Glu Asn Ala Lys Asn Ser Leu Tyr Leu Gln Met Asn Ser Leu
            325                 330                 335

Arg Ala Gly Asp Thr Ala Val Tyr Tyr Cys Ala Arg Asp Thr His Tyr
            340                 345                 350

Arg Leu Tyr Tyr Tyr Ala Met Asp Tyr Trp Gly Gln Gly Thr Thr Val
            355                 360                 365

Thr Val Ser Ser Ala Ser Thr Lys Gly Pro Ser Val Phe Pro Leu Ala
            370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
            405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
            435                 440                 445

Gly Thr Gln Thr Tyr Ile Cys Asn Val Asn His Lys Pro Ser Asn Thr
            450                 455                 460

Lys Val Asp Lys Lys Val Glu Pro Lys Ser Cys Gly Gly Gly Ser Gly
465                 470                 475                 480

Gly Gly Ser Gly Gly Gly Ser Glu Val Gln Leu Val Glu Ser Gly Gly
                485                 490                 495

Gly Leu Val Gln Pro Gly Arg Ser Leu Arg Leu Ser Cys Ala Ala Ser
            500                 505                 510

Gly Phe Thr Phe Asp Asp Tyr Ala Met His Trp Val Arg Gln Ala Pro
            515                 520                 525

Gly Lys Gly Leu Glu Trp Val Ser Ala Ile Thr Trp Asn Ser Gly His
            530                 535                 540

Ile Asp Tyr Ala Asp Ser Val Glu Gly Arg Phe Thr Ile Ser Arg Asp
545                 550                 555                 560

Asn Ala Lys Asn Ser Leu Tyr Leu Gln Met Asn Ser Leu Arg Ala Glu
            565                 570                 575

Asp Thr Ala Val Tyr Tyr Cys Ala Lys Val Ser Tyr Leu Ser Thr Ala
            580                 585                 590

Ser Ser Leu Asp Tyr Trp Gly Gln Gly Thr Leu Val Thr Val Ser Ser
            595                 600                 605

Ala Ser Thr Lys Gly Pro Ser Val Phe Pro Leu Ala Pro Ser Ser Lys
610                 615                 620

Ser Thr Ser Gly Gly Thr Ala Ala Leu Gly Cys Leu Val Lys Asp Tyr
625                 630                 635                 640

Phe Pro Glu Pro Val Thr Val Ser Trp Asn Ser Gly Ala Leu Thr Ser
            645                 650                 655

Gly Val His Thr Phe Pro Ala Val Leu Gln Ser Ser Gly Leu Tyr Ser
                660                 665                 670

Leu Ser Ser Val Val Thr Val Pro Ser Ser Ser Leu Gly Thr Gln Thr
            675                 680                 685

Tyr Ile Cys Asn Val Asn His Lys Pro Ser Asn Thr Lys Val Asp Lys
690                 695                 700

Lys Val Glu Pro Lys Ser Cys Asp Lys Thr His Thr Cys Pro Pro Cys
705                 710                 715                 720

Pro Ala Pro Glu Leu Leu Gly Gly Pro Ser Val Phe Leu Phe Pro Pro
                725                 730                 735

Lys Pro Lys Asp Thr Leu Met Ile Ser Arg Thr Pro Glu Val Thr Cys
            740                 745                 750

Val Val Val Asp Val Ser His Glu Asp Pro Glu Val Lys Phe Asn Trp
            755                 760                 765

Tyr Val Asp Gly Val Glu Val His Asn Ala Lys Thr Lys Pro Arg Glu
770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815

Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
            835                 840                 845

Leu Thr Lys Asn Gln Val Ser Leu Thr Cys Leu Val Lys Gly Phe Tyr
850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
            915                 920                 925

Gln Lys Ser Leu Ser Leu Ser Pro Gly
930                 935

<210> SEQ ID NO 76
<211> LENGTH: 938
<212> TYPE: PRT
<213> ORGANISM: Artificial Sequence
<220> FEATURE:
<223> OTHER INFORMATION: #26 heavy chain variant

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Phe His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Cys Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Gly Gly Gly Gly Ser Gly
225                 230                 235                 240

Gly Gly Ser Gly Gly Gly Ser Gly Gly Glu Val Gln Leu Val
            245                 250                 255

Glu Ser Gly Gly Gly Leu Val Gln Pro Gly Gly Ser Leu Arg Leu Ser
                260                 265                 270

Cys Ala Ala Ser Gly Phe Ser Leu Asp Ser Tyr Gly Val His Trp Val
            275                 280                 285

Arg Gln Ala Pro Gly Lys Cys Leu Glu Trp Val Ser Val Ile Trp Ser
        290                 295                 300

Asp Gly Thr Thr Thr Tyr Asn Ser Ala Leu Lys Ser Arg Phe Thr Ile
305                 310                 315                 320

Ser Arg Asp Asn Ser Lys Asn Thr Leu Tyr Leu Gln Met Asn Ser Leu
                325                 330                 335

Arg Ala Glu Asp Thr Ala Val Tyr Tyr Cys Ala Arg Asp Thr His Tyr
            340                 345                 350

Arg Leu Tyr Tyr Tyr Ala Met Asp Tyr Trp Gly Gln Gly Thr Thr Val
        355                 360                 365

Thr Val Ser Ser Ala Ser Thr Lys Gly Pro Ser Val Phe Pro Leu Ala
        370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu

```
                435                 440                 445
Gly Thr Gln Thr Tyr Ile Cys Asn Val Asn His Lys Pro Ser Asn Thr
450                 455                 460
Lys Val Asp Lys Lys Val Glu Pro Lys Ser Cys Gly Gly Ser Gly
465                 470                 475                 480
Gly Gly Ser Gly Gly Ser Glu Val Gln Leu Val Glu Ser Gly Gly
                485                 490                 495
Gly Leu Val Gln Pro Gly Arg Ser Leu Arg Leu Ser Cys Ala Ala Ser
                500                 505                 510
Gly Phe Thr Phe Asp Asp Tyr Ala Met His Trp Val Arg Gln Ala Pro
            515                 520                 525
Gly Lys Gly Leu Glu Trp Val Ser Ala Ile Thr Trp Asn Ser Gly His
            530                 535                 540
Ile Asp Tyr Ala Asp Ser Val Glu Gly Arg Phe Thr Ile Ser Arg Asp
545                 550                 555                 560
Asn Ala Lys Asn Ser Leu Tyr Leu Gln Met Asn Ser Leu Arg Ala Glu
                565                 570                 575
Asp Thr Ala Val Tyr Tyr Cys Ala Lys Val Ser Tyr Leu Ser Thr Ala
                580                 585                 590
Ser Ser Leu Asp Tyr Trp Gly Gln Gly Thr Leu Val Thr Val Ser Ser
            595                 600                 605
Ala Ser Thr Lys Gly Pro Ser Val Phe Pro Leu Ala Pro Ser Ser Lys
610                 615                 620
Ser Thr Ser Gly Gly Thr Ala Ala Leu Gly Cys Leu Val Lys Asp Tyr
625                 630                 635                 640
Phe Pro Glu Pro Val Thr Val Ser Trp Asn Ser Gly Ala Leu Thr Ser
                645                 650                 655
Gly Val His Thr Phe Pro Ala Val Leu Gln Ser Ser Gly Leu Tyr Ser
            660                 665                 670
Leu Ser Ser Val Val Thr Val Pro Ser Ser Ser Leu Gly Thr Gln Thr
            675                 680                 685
Tyr Ile Cys Asn Val Asn His Lys Pro Ser Asn Thr Lys Val Asp Lys
            690                 695                 700
Lys Val Glu Pro Lys Ser Cys Asp Lys Thr His Thr Cys Pro Pro Cys
705                 710                 715                 720
Pro Ala Pro Glu Leu Leu Gly Gly Pro Ser Val Phe Leu Phe Pro Pro
                725                 730                 735
Lys Pro Lys Asp Thr Leu Met Ile Ser Arg Thr Pro Glu Val Thr Cys
                740                 745                 750
Val Val Val Asp Val Ser His Glu Asp Pro Glu Val Lys Phe Asn Trp
            755                 760                 765
Tyr Val Asp Gly Val Glu Val His Asn Ala Lys Thr Lys Pro Arg Glu
            770                 775                 780
Glu Gln Tyr Asn Ser Thr Tyr Arg Val Val Ser Val Leu Thr Val Leu
785                 790                 795                 800
His Gln Asp Trp Leu Asn Gly Lys Glu Tyr Lys Cys Lys Val Ser Asn
                805                 810                 815
Lys Ala Leu Pro Ala Pro Ile Glu Lys Thr Ile Ser Lys Ala Lys Gly
                820                 825                 830
Gln Pro Arg Glu Pro Gln Val Tyr Thr Leu Pro Pro Ser Arg Asp Glu
            835                 840                 845
Leu Thr Lys Asn Gln Val Ser Leu Thr Cys Leu Val Lys Gly Phe Tyr
850                 855                 860
```

```
Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
        915                 920                 925

Gln Lys Ser Leu Ser Leu Ser Pro Gly Lys
    930                 935

<210> SEQ ID NO 77
<211> LENGTH: 937
<212> TYPE: PRT
<213> ORGANISM: Artificial Sequence
<220> FEATURE:
<223> OTHER INFORMATION: #27 heavy chain variant

<400> SEQUENCE: 77

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gly Gly Gly Gly Ser Gly
225                 230                 235                 240

Gly Gly Gly Ser Gly Gly Gly Ser Gly Gly Glu Val Gln Leu Val
            245                 250                 255

Glu Ser Gly Gly Gly Leu Val Gln Pro Gly Gly Ser Leu Arg Leu Ser
        260                 265                 270

Cys Ala Ala Ser Gly Phe Ser Leu Asp Ser Tyr Gly Val His Trp Val
    275                 280                 285
```

```
Arg Gln Ala Pro Gly Lys Gly Leu Glu Trp Val Ser Val Ile Trp Ser
        290                 295                 300
Asp Gly Thr Thr Thr Tyr Asn Ser Ala Leu Lys Ser Arg Phe Thr Ile
305                 310                 315                 320
Ser Arg Asp Asn Ser Lys Asn Thr Leu Tyr Leu Gln Met Asn Ser Leu
                325                 330                 335
Arg Ala Glu Asp Thr Ala Val Tyr Tyr Cys Ala Arg Asp Thr His Tyr
            340                 345                 350
Arg Leu Tyr Tyr Tyr Ala Met Asp Tyr Trp Gly Gln Gly Thr Thr Val
        355                 360                 365
Thr Val Ser Ser Ala Ser Thr Lys Gly Pro Ser Val Phe Pro Leu Ala
370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
                405                 410                 415
Ala Leu Thr Ser Gly Val His Thr Phe Pro Ala Val Leu Gln Ser Ser
            420                 425                 430
Gly Leu Tyr Ser Leu Ser Ser Val Val Thr Val Pro Ser Ser Ser Leu
        435                 440                 445
Gly Thr Gln Thr Tyr Ile Cys Asn Val Asn His Lys Pro Ser Asn Thr
450                 455                 460
Lys Val Asp Lys Lys Val Glu Pro Lys Ser Cys Gly Gly Gly Ser Gly
465                 470                 475                 480
Gly Gly Ser Gly Gly Gly Ser Glu Val Gln Leu Val Glu Ser Gly Gly
                485                 490                 495
Gly Leu Val Gln Pro Gly Arg Ser Leu Arg Leu Ser Cys Ala Ala Ser
            500                 505                 510
Gly Phe Thr Phe Asp Asp Tyr Ala Met His Trp Val Arg Gln Ala Pro
        515                 520                 525
Gly Lys Gly Leu Glu Trp Val Ser Ala Ile Thr Trp Asn Ser Gly His
530                 535                 540
Ile Asp Tyr Ala Asp Ser Val Glu Gly Arg Phe Thr Ile Ser Arg Asp
545                 550                 555                 560
Asn Ala Lys Asn Ser Leu Tyr Leu Gln Met Asn Ser Leu Arg Ala Glu
                565                 570                 575
Asp Thr Ala Val Tyr Tyr Cys Ala Lys Val Ser Tyr Leu Ser Thr Ala
            580                 585                 590
Ser Ser Leu Asp Tyr Trp Gly Gln Gly Thr Leu Val Thr Val Ser Ser
        595                 600                 605
Ala Ser Thr Lys Gly Pro Ser Val Phe Pro Leu Ala Pro Ser Ser Lys
610                 615                 620
Ser Thr Ser Gly Gly Thr Ala Ala Leu Gly Cys Leu Val Lys Asp Tyr
625                 630                 635                 640
Phe Pro Glu Pro Val Thr Val Ser Trp Asn Ser Gly Ala Leu Thr Ser
                645                 650                 655
Gly Val His Thr Phe Pro Ala Val Leu Gln Ser Ser Gly Leu Tyr Ser
            660                 665                 670
Leu Ser Ser Val Val Thr Val Pro Ser Ser Ser Leu Gly Thr Gln Thr
        675                 680                 685
Tyr Ile Cys Asn Val Asn His Lys Pro Ser Asn Thr Lys Val Asp Lys
690                 695                 700
```

Lys Val Glu Pro Lys Ser Cys Asp Lys Thr His Thr Cys Pro Pro Cys
705                 710                 715                 720

Pro Ala Pro Glu Leu Leu Gly Gly Pro Ser Val Phe Leu Phe Pro Pro
                725                 730                 735

Lys Pro Lys Asp Thr Leu Met Ile Ser Arg Thr Pro Glu Val Thr Cys
            740                 745                 750

Val Val Val Asp Val Ser His Glu Asp Pro Glu Val Lys Phe Asn Trp
        755                 760                 765

Tyr Val Asp Gly Val Glu Val His Asn Ala Lys Thr Lys Pro Arg Glu
    770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815

Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
        835                 840                 845

Leu Thr Lys Asn Gln Val Ser Leu Thr Cys Leu Val Lys Gly Phe Tyr
    850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
        915                 920                 925

Gln Lys Ser Leu Ser Leu Ser Pro Gly
    930                 935

<210> SEQ ID NO 78
<211> LENGTH: 932
<212> TYPE: PRT
<213> ORGANISM: Artificial Sequence
<220> FEATURE:
<223> OTHER INFORMATION: #30 heavy chain variant

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Gly Gly Gly Ser Gly Gly Gly Ser Gly
225                 230                 235                 240

Gly Gly Ser Gly Gly Glu Val Gln Leu Val Glu Ser Gly Gly
                245                 250                 255

Leu Val Gln Pro Gly Arg Ser Leu Arg Leu Ser Cys Ala Ala Ser Gly
            260                 265                 270

Phe Thr Phe Asp Asp Tyr Ala Met His Trp Val Arg Gln Ala Pro Gly
        275                 280                 285

Lys Gly Leu Glu Trp Val Ser Ala Ile Thr Trp Asn Ser Gly His Ile
    290                 295                 300

Asp Tyr Ala Asp Ser Val Glu Gly Arg Phe Thr Ile Ser Arg Asp Asn
305                 310                 315                 320

Ala Lys Asn Ser Leu Tyr Leu Gln Met Asn Ser Leu Arg Ala Glu Asp
                325                 330                 335

Thr Ala Val Tyr Tyr Cys Ala Lys Val Ser Tyr Leu Ser Thr Ala Ser
            340                 345                 350

Ser Leu Asp Tyr Trp Gly Gln Gly Thr Leu Val Thr Val Ser Ser Ala
        355                 360                 365

Ser Thr Lys Gly Pro Ser Val Phe Pro Leu Ala Pro Ser Ser Lys Ser
    370                 375                 380

Thr Ser Gly Gly Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
            420                 425                 430

Ser Ser Val Val Thr Val Pro Ser Ser Ser Leu Gly Thr Gln Thr Tyr
        435                 440                 445

Ile Cys Asn Val Asn His Lys Pro Ser Asn Thr Lys Val Asp Lys Lys
    450                 455                 460

Val Glu Pro Lys Ser Cys Gly Gly Gly Ser Gly Gly Gly Ser Gly Gly
465                 470                 475                 480

Gly Ser Glu Val Gln Leu Val Glu Ser Gly Gly Gly Leu Val Gln Pro
                485                 490                 495

Gly Gly Ser Leu Arg Leu Ser Cys Ala Ala Ser Gly Phe Ser Leu Asp
            500                 505                 510

Ser Tyr Gly Val His Trp Val Arg Gln Ala Pro Gly Lys Gly Leu Glu
        515                 520                 525

Trp Val Ser Val Ile Trp Ser Asp Gly Thr Thr Thr Tyr Asn Ser Ala
    530                 535                 540

Leu Lys Ser Arg Phe Thr Ile Ser Arg Asp Asn Ser Lys Asn Thr Leu
```

```
            545                 550                 555                 560
Tyr Leu Gln Met Asn Ser Leu Arg Ala Glu Asp Thr Ala Val Tyr Tyr
                565                 570                 575
Cys Ala Arg Asp Thr His Tyr Arg Leu Tyr Tyr Ala Met Asp Tyr
            580                 585                 590
Trp Gly Gln Gly Thr Thr Val Thr Val Ser Ser Ala Ser Thr Lys Gly
                595                 600                 605
Pro Ser Val Phe Pro Leu Ala Pro Ser Ser Lys Ser Thr Ser Gly Gly
            610                 615                 620
Thr Ala Ala Leu Gly Cys Leu Val Lys Asp Tyr Phe Pro Glu Pro Val
625                 630                 635                 640
Thr Val Ser Trp Asn Ser Gly Ala Leu Thr Ser Gly Val His Thr Phe
                645                 650                 655
Pro Ala Val Leu Gln Ser Ser Gly Leu Tyr Ser Leu Ser Ser Val Val
                660                 665                 670
Thr Val Pro Ser Ser Ser Leu Gly Thr Gln Thr Tyr Ile Cys Asn Val
            675                 680                 685
Asn His Lys Pro Ser Asn Thr Lys Val Asp Lys Lys Val Glu Pro Lys
            690                 695                 700
Ser Cys Asp Lys Thr His Thr Cys Pro Pro Cys Pro Ala Pro Glu Leu
705                 710                 715                 720
Leu Gly Gly Pro Ser Val Phe Leu Phe Pro Pro Lys Pro Lys Asp Thr
                725                 730                 735
Leu Met Ile Ser Arg Thr Pro Glu Val Thr Cys Val Val Val Asp Val
                740                 745                 750
Ser His Glu Asp Pro Glu Val Lys Phe Asn Trp Tyr Val Asp Gly Val
            755                 760                 765
Glu Val His Asn Ala Lys Thr Lys Pro Arg Glu Glu Gln Tyr Asn Ser
            770                 775                 780
Thr Tyr Arg Val Val Ser Val Leu Thr Val Leu His Gln Asp Trp Leu
785                 790                 795                 800
Asn Gly Lys Glu Tyr Lys Cys Lys Val Ser Asn Lys Ala Leu Pro Ala
                805                 810                 815
Pro Ile Glu Lys Thr Ile Ser Lys Ala Lys Gly Gln Pro Arg Glu Pro
                820                 825                 830
Gln Val Tyr Thr Leu Pro Pro Ser Arg Asp Glu Leu Thr Lys Asn Gln
            835                 840                 845
Val Ser Leu Thr Cys Leu Val Lys Gly Phe Tyr Pro Ser Asp Ile Ala
850                 855                 860
Val Glu Trp Glu Ser Asn Gly Gln Pro Glu Asn Asn Tyr Lys Thr Thr
865                 870                 875                 880
Pro Pro Val Leu Asp Ser Asp Gly Ser Phe Phe Leu Tyr Ser Lys Leu
                885                 890                 895
Thr Val Asp Lys Ser Arg Trp Gln Gln Gly Asn Val Phe Ser Cys Ser
            900                 905                 910
Val Met His Glu Ala Leu His Asn His Tyr Thr Gln Lys Ser Leu Ser
            915                 920                 925
Leu Ser Pro Gly
    930

<210> SEQ ID NO 79
<211> LENGTH: 936
<212> TYPE: PRT
<213> ORGANISM: Artificial Sequence
```

<220> FEATURE:
<223> OTHER INFORMATION: #13 heavy chain variant

<400> SEQUENCE: 79

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Ala Pro Phe Thr Phe Gly Cys Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gly Gly Gly Gly Ser Gly
225                 230                 235                 240

Gly Gly Gly Ser Gly Gly Gly Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Ser Leu Asp Ser Tyr Gly Val His Trp Val
        275                 280                 285

Arg Gln Ala Thr Gly Lys Cys Leu Glu Trp Val Ser Val Ile Trp Ser
    290                 295                 300

Asp Gly Thr Thr Thr Tyr Asn Ser Ala Leu Lys Ser Arg Phe Thr Ile
305                 310                 315                 320

Ser Arg Glu Asn Ala Lys Asn Ser Leu Tyr Leu Gln Met Asn Ser Leu
                325                 330                 335

Arg Ala Gly Asp Thr Ala Val Tyr Tyr Cys Ala Arg Asp Thr His Tyr
            340                 345                 350

Arg Leu Tyr Tyr Tyr Ala Met Asp Tyr Trp Gly Gln Gly Thr Thr Val
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400
```

```
Val Lys Asp Tyr Phe Pro Glu Pro Val Thr Val Ser Trp Asn Ser Gly
            405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
            435                 440                 445

Gly Thr Gln Thr Tyr Ile Cys Asn Val Asn His Lys Pro Ser Asn Thr
            450                 455                 460

Lys Val Asp Lys Lys Val Glu Pro Lys Ser Cys Gly Gly Ser Gly
465                 470                 475                 480

Gly Gly Ser Gly Gly Ser Glu Val Gln Leu Val Glu Ser Gly Gly
                485                 490                 495

Gly Leu Val Gln Pro Gly Arg Ser Leu Arg Leu Ser Cys Ala Ala Ser
            500                 505                 510

Gly Phe Thr Phe Asp Asp Tyr Ala Met His Trp Val Arg Gln Ala Pro
            515                 520                 525

Gly Lys Gly Leu Glu Trp Val Ser Ala Ile Thr Trp Asn Ser Gly His
            530                 535                 540

Ile Asp Tyr Ala Asp Ser Val Glu Gly Arg Phe Thr Ile Ser Arg Asp
545                 550                 555                 560

Asn Ala Lys Asn Ser Leu Tyr Leu Gln Met Asn Ser Leu Arg Ala Glu
                565                 570                 575

Asp Thr Ala Val Tyr Tyr Cys Ala Lys Val Ser Tyr Leu Ser Thr Ala
                580                 585                 590

Ser Ser Leu Asp Tyr Trp Gly Gln Gly Thr Leu Val Thr Val Ser Ser
            595                 600                 605

Ala Ser Thr Lys Gly Pro Ser Val Phe Pro Leu Ala Pro Ser Ser Lys
            610                 615                 620

Ser Thr Ser Gly Gly Thr Ala Ala Leu Gly Cys Leu Val Lys Asp Tyr
625                 630                 635                 640

Phe Pro Glu Pro Val Thr Val Ser Trp Asn Ser Gly Ala Leu Thr Ser
                645                 650                 655

Gly Val His Thr Phe Pro Ala Val Leu Gln Ser Ser Gly Leu Tyr Ser
                660                 665                 670

Leu Ser Ser Val Val Thr Val Pro Ser Ser Ser Leu Gly Thr Gln Thr
            675                 680                 685

Tyr Ile Cys Asn Val Asn His Lys Pro Ser Asn Thr Lys Val Asp Lys
            690                 695                 700

Lys Val Glu Pro Lys Ser Cys Asp Lys Thr His Thr Cys Pro Pro Cys
705                 710                 715                 720

Pro Ala Pro Glu Leu Leu Gly Gly Pro Ser Val Phe Leu Phe Pro Pro
                725                 730                 735

Lys Pro Lys Asp Thr Leu Met Ile Ser Arg Thr Pro Glu Val Thr Cys
                740                 745                 750

Val Val Val Asp Val Ser His Glu Asp Pro Glu Val Lys Phe Asn Trp
            755                 760                 765

Tyr Val Asp Gly Val Glu Val His Asn Ala Lys Thr Lys Pro Arg Glu
            770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815
```

```
Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
        835                 840                 845

Leu Thr Lys Asn Gln Val Ser Leu Thr Cys Leu Val Lys Gly Phe Tyr
    850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
        915                 920                 925

Gln Lys Ser Leu Ser Leu Ser Pro
    930                 935

<210> SEQ ID NO 80
<211> LENGTH: 936
<212> TYPE: PRT
<213> ORGANISM: Artificial Sequence
<220> FEATURE:
<223> OTHER INFORMATION: #26 heavy chain variant

<400> SEQUENCE: 80

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
            85                  90                  95

Thr His Ala Pro Phe Thr Phe Gly Cys Gly Thr Lys Leu Glu Ile Lys
        100                 105                 110

Arg Thr Val Ala Ala Pro Ser Val Phe Ile Phe Pro Pro Ser Asp Glu
    115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Gly Gly Gly Gly Ser Gly
225                 230                 235                 240
```

```
Gly Gly Gly Ser Gly Gly Gly Ser Gly Glu Val Gln Leu Val
                245             250             255
Glu Ser Gly Gly Gly Leu Val Gln Pro Gly Gly Ser Leu Arg Leu Ser
            260                 265                 270
Cys Ala Ala Ser Gly Phe Ser Leu Asp Ser Tyr Gly Val His Trp Val
        275                 280                 285
Arg Gln Ala Pro Gly Lys Cys Leu Glu Trp Val Ser Val Ile Trp Ser
    290                 295                 300
Asp Gly Thr Thr Thr Tyr Asn Ser Ala Leu Lys Ser Arg Phe Thr Ile
305                 310                 315                 320
Ser Arg Asp Asn Ser Lys Asn Thr Leu Tyr Leu Gln Met Asn Ser Leu
                325                 330                 335
Arg Ala Glu Asp Thr Ala Val Tyr Tyr Cys Ala Arg Asp Thr His Tyr
            340                 345                 350
Arg Leu Tyr Tyr Tyr Ala Met Asp Tyr Trp Gly Gln Gly Thr Thr Val
        355                 360                 365
Thr Val Ser Ser Ala Ser Thr Lys Gly Pro Ser Val Phe Pro Leu Ala
    370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
                405                 410                 415
Ala Leu Thr Ser Gly Val His Thr Phe Pro Ala Val Leu Gln Ser Ser
            420                 425                 430
Gly Leu Tyr Ser Leu Ser Ser Val Val Thr Val Pro Ser Ser Ser Leu
        435                 440                 445
Gly Thr Gln Thr Tyr Ile Cys Asn Val Asn His Lys Pro Ser Asn Thr
    450                 455                 460
Lys Val Asp Lys Lys Val Glu Pro Lys Ser Cys Gly Gly Gly Ser Gly
465                 470                 475                 480
Gly Gly Ser Gly Gly Gly Ser Glu Val Gln Leu Val Glu Ser Gly Gly
                485                 490                 495
Gly Leu Val Gln Pro Gly Arg Ser Leu Arg Leu Ser Cys Ala Ala Ser
            500                 505                 510
Gly Phe Thr Phe Asp Asp Tyr Ala Met His Trp Val Arg Gln Ala Pro
        515                 520                 525
Gly Lys Gly Leu Glu Trp Val Ser Ala Ile Thr Trp Asn Ser Gly His
    530                 535                 540
Ile Asp Tyr Ala Asp Ser Val Glu Gly Arg Phe Thr Ile Ser Arg Asp
545                 550                 555                 560
Asn Ala Lys Asn Ser Leu Tyr Leu Gln Met Asn Ser Leu Arg Ala Glu
                565                 570                 575
Asp Thr Ala Val Tyr Tyr Cys Ala Lys Val Ser Tyr Leu Ser Thr Ala
            580                 585                 590
Ser Ser Leu Asp Tyr Trp Gly Gln Gly Thr Leu Val Thr Val Ser Ser
        595                 600                 605
Ala Ser Thr Lys Gly Pro Ser Val Phe Pro Leu Ala Pro Ser Ser Lys
    610                 615                 620
Ser Thr Ser Gly Gly Thr Ala Ala Leu Gly Cys Leu Val Lys Asp Tyr
625                 630                 635                 640
Phe Pro Glu Pro Val Thr Val Ser Trp Asn Ser Gly Ala Leu Thr Ser
                645                 650                 655
Gly Val His Thr Phe Pro Ala Val Leu Gln Ser Ser Gly Leu Tyr Ser
```

```
                        660                 665                 670
Leu Ser Ser Val Val Thr Val Pro Ser Ser Leu Gly Thr Gln Thr
            675                 680                 685

Tyr Ile Cys Asn Val Asn His Lys Pro Ser Asn Thr Lys Val Asp Lys
690                 695                 700

Lys Val Glu Pro Lys Ser Cys Asp Lys Thr His Thr Cys Pro Pro Cys
705                 710                 715                 720

Pro Ala Pro Glu Leu Leu Gly Gly Pro Ser Val Phe Leu Phe Pro Pro
                725                 730                 735

Lys Pro Lys Asp Thr Leu Met Ile Ser Arg Thr Pro Glu Val Thr Cys
            740                 745                 750

Val Val Val Asp Val Ser His Glu Asp Pro Glu Val Lys Phe Asn Trp
        755                 760                 765

Tyr Val Asp Gly Val Glu Val His Asn Ala Lys Thr Lys Pro Arg Glu
770                 775                 780

Glu Gln Tyr Asn Ser Thr Tyr Arg Val Val Ser Val Leu Thr Val Leu
785                 790                 795                 800

His Gln Asp Trp Leu Asn Gly Lys Glu Tyr Lys Cys Lys Val Ser Asn
                805                 810                 815

Lys Ala Leu Pro Ala Pro Ile Glu Lys Thr Ile Ser Lys Ala Lys Gly
            820                 825                 830

Gln Pro Arg Glu Pro Gln Val Tyr Thr Leu Pro Pro Ser Arg Asp Glu
        835                 840                 845

Leu Thr Lys Asn Gln Val Ser Leu Thr Cys Leu Val Lys Gly Phe Tyr
850                 855                 860

Pro Ser Asp Ile Ala Val Glu Trp Glu Ser Asn Gly Gln Pro Glu Asn
865                 870                 875                 880

Asn Tyr Lys Thr Thr Pro Pro Val Leu Asp Ser Asp Gly Ser Phe Phe
                885                 890                 895

Leu Tyr Ser Lys Leu Thr Val Asp Lys Ser Arg Trp Gln Gln Gly Asn
            900                 905                 910

Val Phe Ser Cys Ser Val Met His Glu Ala Leu His Asn His Tyr Thr
        915                 920                 925

Gln Lys Ser Leu Ser Leu Ser Pro
    930                 935

<210> SEQ ID NO 81
<211> LENGTH: 936
<212> TYPE: PRT
<213> ORGANISM: Artificial Sequence
<220> FEATURE:
<223> OTHER INFORMATION: #27 heavy chain variant

<400> SEQUENCE: 81

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asp Thr Tyr Phe His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
```

```
                    85                  90                  95
Thr His Ala Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Gly Gly Gly Gly Ser Gly
225                 230                 235                 240

Gly Gly Gly Ser Gly Gly Gly Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Ser Leu Asp Ser Tyr Gly Val His Trp Val
            275                 280                 285

Arg Gln Ala Pro Gly Lys Gly Leu Glu Trp Val Ser Val Ile Trp Ser
            290                 295                 300

Asp Gly Thr Thr Thr Tyr Asn Ser Ala Leu Lys Ser Arg Phe Thr Ile
305                 310                 315                 320

Ser Arg Asp Asn Ser Lys Asn Thr Leu Tyr Leu Gln Met Asn Ser Leu
                325                 330                 335

Arg Ala Glu Asp Thr Ala Val Tyr Tyr Cys Ala Arg Asp Thr His Tyr
            340                 345                 350

Arg Leu Tyr Tyr Tyr Ala Met Asp Tyr Trp Gly Gln Gly Thr Thr Val
            355                 360                 365

Thr Val Ser Ser Ala Ser Thr Lys Gly Pro Ser Val Phe Pro Leu Ala
370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
            435                 440                 445

Gly Thr Gln Thr Tyr Ile Cys Asn Val Asn His Lys Pro Ser Asn Thr
            450                 455                 460

Lys Val Asp Lys Lys Val Glu Pro Lys Ser Cys Gly Gly Gly Gly Ser
465                 470                 475                 480

Gly Gly Ser Gly Gly Gly Ser Glu Val Gln Leu Val Glu Ser Gly Gly
                485                 490                 495

Gly Leu Val Gln Pro Gly Arg Ser Leu Arg Leu Ser Cys Ala Ala Ser
            500                 505                 510
```

-continued

```
Gly Phe Thr Phe Asp Asp Tyr Ala Met His Trp Val Arg Gln Ala Pro
            515                 520                 525
Gly Lys Gly Leu Glu Trp Val Ser Ala Ile Thr Trp Asn Ser Gly His
        530                 535                 540
Ile Asp Tyr Ala Asp Ser Val Glu Gly Arg Phe Thr Ile Ser Arg Asp
545                 550                 555                 560
Asn Ala Lys Asn Ser Leu Tyr Leu Gln Met Asn Ser Leu Arg Ala Glu
                565                 570                 575
Asp Thr Ala Val Tyr Tyr Cys Ala Lys Val Ser Tyr Leu Ser Thr Ala
            580                 585                 590
Ser Ser Leu Asp Tyr Trp Gly Gln Gly Thr Leu Val Thr Val Ser Ser
        595                 600                 605
Ala Ser Thr Lys Gly Pro Ser Val Phe Pro Leu Ala Pro Ser Ser Lys
    610                 615                 620
Ser Thr Ser Gly Gly Thr Ala Ala Leu Gly Cys Leu Val Lys Asp Tyr
625                 630                 635                 640
Phe Pro Glu Pro Val Thr Val Ser Trp Asn Ser Gly Ala Leu Thr Ser
                645                 650                 655
Gly Val His Thr Phe Pro Ala Val Leu Gln Ser Ser Gly Leu Tyr Ser
            660                 665                 670
Leu Ser Ser Val Val Thr Val Pro Ser Ser Ser Leu Gly Thr Gln Thr
        675                 680                 685
Tyr Ile Cys Asn Val Asn His Lys Pro Ser Asn Thr Lys Val Asp Lys
    690                 695                 700
Lys Val Glu Pro Lys Ser Cys Asp Lys Thr His Thr Cys Pro Pro Cys
705                 710                 715                 720
Pro Ala Pro Glu Leu Leu Gly Gly Pro Ser Val Phe Leu Phe Pro Pro
                725                 730                 735
Lys Pro Lys Asp Thr Leu Met Ile Ser Arg Thr Pro Glu Val Thr Cys
            740                 745                 750
Val Val Val Asp Val Ser His Glu Asp Pro Glu Val Lys Phe Asn Trp
        755                 760                 765
Tyr Val Asp Gly Val Glu Val His Asn Ala Lys Thr Lys Pro Arg Glu
    770                 775                 780
Glu Gln Tyr Asn Ser Thr Tyr Arg Val Val Ser Val Leu Thr Val Leu
785                 790                 795                 800
His Gln Asp Trp Leu Asn Gly Lys Glu Tyr Lys Cys Lys Val Ser Asn
                805                 810                 815
Lys Ala Leu Pro Ala Pro Ile Glu Lys Thr Ile Ser Lys Ala Lys Gly
            820                 825                 830
Gln Pro Arg Glu Pro Gln Val Tyr Thr Leu Pro Pro Ser Arg Asp Glu
        835                 840                 845
Leu Thr Lys Asn Gln Val Ser Leu Thr Cys Leu Val Lys Gly Phe Tyr
    850                 855                 860
Pro Ser Asp Ile Ala Val Glu Trp Glu Ser Asn Gly Gln Pro Glu Asn
865                 870                 875                 880
Asn Tyr Lys Thr Thr Pro Pro Val Leu Asp Ser Asp Gly Ser Phe Phe
                885                 890                 895
Leu Tyr Ser Lys Leu Thr Val Asp Lys Ser Arg Trp Gln Gln Gly Asn
            900                 905                 910
Val Phe Ser Cys Ser Val Met His Glu Ala Leu His Asn His Tyr Thr
        915                 920                 925
```

```
            Gln Lys Ser Leu Ser Leu Ser Pro
                930                 935

<210> SEQ ID NO 82
<211> LENGTH: 931
<212> TYPE: PRT
<213> ORGANISM: Artificial Sequence
<220> FEATURE:
<223> OTHER INFORMATION: #30 heavy chain variant

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gly Gly Gly Ser Gly Gly Gly Ser Gly
225                 230                 235                 240

Gly Gly Gly Ser Gly Gly Glu Val Gln Leu Val Glu Ser Gly Gly Gly
                245                 250                 255

Leu Val Gln Pro Gly Arg Ser Leu Arg Leu Ser Cys Ala Ala Ser Gly
            260                 265                 270

Phe Thr Phe Asp Asp Tyr Ala Met His Trp Val Arg Gln Ala Pro Gly
        275                 280                 285

Lys Gly Leu Glu Trp Val Ser Ala Ile Thr Trp Asn Ser Gly His Ile
    290                 295                 300

Asp Tyr Ala Asp Ser Val Glu Gly Arg Phe Thr Ile Ser Arg Asp Asn
305                 310                 315                 320

Ala Lys Asn Ser Leu Tyr Leu Gln Met Asn Ser Leu Arg Ala Glu Asp
                325                 330                 335

Thr Ala Val Tyr Tyr Cys Ala Lys Val Ser Tyr Leu Ser Thr Ala Ser
            340                 345                 350
```

```
Ser Leu Asp Tyr Trp Gly Gln Gly Thr Leu Val Thr Val Ser Ser Ala
            355                 360                 365

Ser Thr Lys Gly Pro Ser Val Phe Pro Leu Ala Pro Ser Ser Lys Ser
370                 375                 380

Thr Ser Gly Gly Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
                420                 425                 430

Ser Ser Val Val Thr Val Pro Ser Ser Ser Leu Gly Thr Gln Thr Tyr
            435                 440                 445

Ile Cys Asn Val Asn His Lys Pro Ser Asn Thr Lys Val Asp Lys Lys
450                 455                 460

Val Glu Pro Lys Ser Cys Gly Gly Gly Ser Gly Gly Gly Ser Gly Gly
465                 470                 475                 480

Gly Ser Glu Val Gln Leu Val Glu Ser Gly Gly Gly Leu Val Gln Pro
                485                 490                 495

Gly Gly Ser Leu Arg Leu Ser Cys Ala Ala Ser Gly Phe Ser Leu Asp
            500                 505                 510

Ser Tyr Gly Val His Trp Val Arg Gln Ala Pro Gly Lys Gly Leu Glu
            515                 520                 525

Trp Val Ser Val Ile Trp Ser Asp Gly Thr Thr Tyr Asn Ser Ala
            530                 535                 540

Leu Lys Ser Arg Phe Thr Ile Ser Arg Asp Asn Ser Lys Asn Thr Leu
545                 550                 555                 560

Tyr Leu Gln Met Asn Ser Leu Arg Ala Glu Asp Thr Ala Val Tyr Tyr
                565                 570                 575

Cys Ala Arg Asp Thr His Tyr Arg Leu Tyr Tyr Ala Met Asp Tyr
                580                 585                 590

Trp Gly Gln Gly Thr Thr Val Thr Val Ser Ser Ala Ser Thr Lys Gly
            595                 600                 605

Pro Ser Val Phe Pro Leu Ala Pro Ser Ser Lys Ser Thr Ser Gly Gly
            610                 615                 620

Thr Ala Ala Leu Gly Cys Leu Val Lys Asp Tyr Phe Pro Glu Pro Val
625                 630                 635                 640

Thr Val Ser Trp Asn Ser Gly Ala Leu Thr Ser Gly Val His Thr Phe
                645                 650                 655

Pro Ala Val Leu Gln Ser Ser Gly Leu Tyr Ser Leu Ser Ser Val Val
                660                 665                 670

Thr Val Pro Ser Ser Ser Leu Gly Thr Gln Thr Tyr Ile Cys Asn Val
            675                 680                 685

Asn His Lys Pro Ser Asn Thr Lys Val Asp Lys Lys Val Glu Pro Lys
            690                 695                 700

Ser Cys Asp Lys Thr His Thr Cys Pro Pro Cys Pro Ala Pro Glu Leu
705                 710                 715                 720

Leu Gly Gly Pro Ser Val Phe Leu Phe Pro Pro Lys Pro Lys Asp Thr
                725                 730                 735

Leu Met Ile Ser Arg Thr Pro Glu Val Thr Cys Val Val Val Asp Val
                740                 745                 750

Ser His Glu Asp Pro Glu Val Lys Phe Asn Trp Tyr Val Asp Gly Val
            755                 760                 765

Glu Val His Asn Ala Lys Thr Lys Pro Arg Glu Glu Gln Tyr Asn Ser
```

```
              770              775            780
Thr Tyr Arg Val Val Ser Val Leu Thr Val Leu His Gln Asp Trp Leu
785             790             795             800

Asn Gly Lys Glu Tyr Lys Cys Lys Val Ser Asn Lys Ala Leu Pro Ala
            805             810             815

Pro Ile Glu Lys Thr Ile Ser Lys Ala Lys Gly Gln Pro Arg Glu Pro
            820             825             830

Gln Val Tyr Thr Leu Pro Pro Ser Arg Asp Glu Leu Thr Lys Asn Gln
            835             840             845

Val Ser Leu Thr Cys Leu Val Lys Gly Phe Tyr Pro Ser Asp Ile Ala
850             855             860

Val Glu Trp Glu Ser Asn Gly Gln Pro Glu Asn Asn Tyr Lys Thr Thr
865             870             875             880

Pro Pro Val Leu Asp Ser Asp Gly Ser Phe Phe Leu Tyr Ser Lys Leu
            885             890             895

Thr Val Asp Lys Ser Arg Trp Gln Gln Gly Asn Val Phe Ser Cys Ser
            900             905             910

Val Met His Glu Ala Leu His Asn His Tyr Thr Gln Lys Ser Leu Ser
            915             920             925

Leu Ser Pro
930
```